United States Patent
Chen et al.

(10) Patent No.: US 10,626,135 B2
(45) Date of Patent: Apr. 21, 2020

(54) CRYSTAL FORMS OF SODIUM-GLUCOSE CO-TRANSPORTER INHIBITOR, PROCESSES FOR PREPARATION AND USE THEREOF

(71) Applicant: CRYSTAL PHARMACEUTICAL (SUZHOU) CO., LTD., Suzhou, Jiangsu (CN)

(72) Inventors: Minhua Chen, Jiangsu (CN); Yanfeng Zhang, Jiangsu (CN); Po Zou, Jiangsu (CN); Kai Liu, Jiangsu (CN); Xiaoyu Zhang, Jiangsu (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 16/304,280

(22) PCT Filed: May 25, 2017

(86) PCT No.: PCT/CN2017/085813
§ 371 (c)(1),
(2) Date: Nov. 24, 2018

(87) PCT Pub. No.: WO2017/202351
PCT Pub. Date: Nov. 30, 2017

(65) Prior Publication Data
US 2019/0169219 A1      Jun. 6, 2019

(30) Foreign Application Priority Data

May 25, 2016   (CN) .......................... 2016 1 0355235

(51) Int. Cl.
| C07H 15/14 | (2006.01) |
| C07H 1/06 | (2006.01) |
| A61K 31/7028 | (2006.01) |
| A61P 3/10 | (2006.01) |

(52) U.S. Cl.
CPC ......... *C07H 15/14* (2013.01); *A61K 31/7028* (2013.01); *C07H 1/06* (2013.01); *A61P 3/10* (2018.01); *C07B 2200/13* (2013.01)

(58) Field of Classification Search
None
See application file for complete search history.

(56) References Cited

U.S. PATENT DOCUMENTS

| 8,217,156 B2 | 7/2012 | De Paul et al. |
| 2011/0077212 A1 | 3/2011 | Seed et al. |

FOREIGN PATENT DOCUMENTS

| WO | 2009/014970 A1 | 1/2009 |
| WO | 2010/009197 A1 | 1/2010 |
| WO | 2011/109333 A1 | 9/2011 |
| WO | 2012/094293 A1 | 7/2012 |

OTHER PUBLICATIONS

CN 102112483. A, published Jun. 2011, machine translation.*
International Search Report and Written Opinion for Application No. PCT/CN2017/085713, dated Aug. 31, 2017, 13 pages.

* cited by examiner

*Primary Examiner* — Layla D Berry
(74) *Attorney, Agent, or Firm* — McCarter & English, LLP; Steven G. Davis; Wei Song

(57) ABSTRACT

The present disclosure relates to novel crystalline forms of a sodium-glucose co-transporter inhibitor drug (Sotagliflozin), processes for preparation and use thereof. The present disclosure also relates to pharmaceutical composition comprises novel crystalline forms of Sotagliflozin and use of novel crystalline forms and pharmaceutical composition of Sotagliflozin for preparing drugs for treating diseases. The crystalline forms provided by the present disclosure have advantages of good stability, relatively low hygroscopicity, suitability for process development and post-treatment, simple processes for preparation, low cost, and has significant value for future drug optimization and development.

5 Claims, 28 Drawing Sheets

CRYSTAL FORMS OF SODIUM-GLUCOSE CO-TRANSPORTER INHIBITOR, PROCESSES FOR PREPARATION AND USE THEREOF

TECHNICAL FIELD

The present disclosure relates to the technical field of pharmaceutical crystal. In particular, it relates to novel crystalline forms of a sodium-glucose co-transporter inhibitor, processes for preparation and use thereof.

BACKGROUND

Sotagliflozin is an investigational new oral dual inhibitor of sodium-glucose cotransporters 1 and 2 (SGLT-1 and SGLT-2) which is developed by Lexicon and currently in Phase 3 clinical trial. It could be a potential treatment option for diabetics. Sotagliflozin has been shown encouraging results in exploratory (Phase 2) studies, including reduction of blood sugar, improvement in glycaemic variability, and reduced meal-time insulin dose compared with placebo in type 1 diabetics. Phase 2 studies exploring treatment in people with type 2 diabetes, including those with renal impairment, showed lowering of blood sugar, weight loss and blood pressure improvements. The chemical name of Sotagliflozin is (2S,3R,4R,5S,6R)-2-(4-chloro-3-(4-ethoxybenzyl)phenyl)-6-(methylthio)tetrahydro-2H-pyran-3,4,5-triol, and the structure is shown as formula (I):

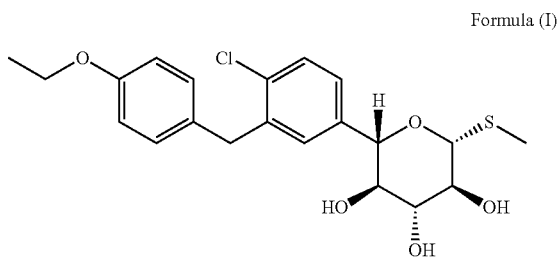 [SMILES: CCOc1ccc(Cc2cc([C@@H]3O[C@H](SC)[C@@H](O)[C@H](O)[C@H]3O)ccc2Cl)cc1]

Formula (I)

CN101343296B disclosed the preparation of Sotagliflozin, while no crystalline information thereof was disclosed. CN102112483A (which is incorporated herein by reference) disclosed anhydrous crystalline Form 1 and crystalline Form 2 (herein after briefly named as existing crystalline Form 1 and existing crystalline Form 2). The inventors of the present disclosure have found it difficult to repetitively prepare the existing crystalline Form 1. Although it's easier to repetitively prepare the existing crystalline Form 2 compared with Form 1, crystalline Form 2 is not stable under high water activity. Meanwhile, it is also found that the existing crystalline Form 2 has poor stability after grinding, and crystal transformation is easy to occur in the formulation preparation process. The existing crystalline Form 2 also has drawbacks such as wide particle size distribution, uneven particle size distribution and the like, which make it not beneficial to the post-treatment of drug development.

Novel crystalline forms (including anhydrates, hydrates and solvates) of the active pharmaceutical ingredients may provide more solid forms in the formulation, and may also offer processing advantages and better physicochemical properties. The processing advantages include processability, purification ability or serving as intermediate crystal forms to facilitate solid state transformation to desired forms. The better physicochemical properties include bioavailability and stability. For certain pharmaceutical compounds, the novel crystalline forms can also help to improve drugs' performance.

Therefore, there is still a need to develop novel crystalline forms which are superior in one or more aspects compared with existing crystalline Form 1 and Form 2, so that these novel crystalline forms can meet strict requirements of industrial formulation production, and crystal properties or drug properties for future drug application.

SUMMARY

The main objective of the present disclosure is to provide novel crystalline forms of Sotagliflozin, processes for preparation and use thereof.

The present disclosure is to provide multiple novel crystalline forms, named as crystalline Form I, crystalline Form II, crystalline Form III, crystalline Form V, crystalline Form VI, crystalline Form VII and crystalline Form VIII. According to the above objective, the first scheme adopted by the present disclosure is to provide crystalline Form I of Sotagliflozin. Using Cu-Kα radiation, the X-ray powder diffraction pattern of crystalline Form I shows diffraction peaks at 2theta values of 3.6°±0.2°, 12.7°±0.2° and 14.1°±0.2°.

Furthermore, the X-ray powder diffraction pattern of crystalline Form I of the present disclosure shows one or more diffraction peaks at 2theta values of 15.6°±0.2°, 17.1°±0.2°, 18.7°±0.2°, 9.0°±0.2°, 21.0°±0.2° and 25.7°±0.2°.

According to a preferred aspect of the present disclosure, the X-ray powder diffraction pattern of crystalline Form I shows one or two or three diffraction peaks at 2theta values of 15.6°±0.2°, 17.1°±0.2° and 18.7°±0.2°. More preferably, the X-ray powder diffraction pattern of crystalline Form I shows diffraction peaks at 2theta values of 15.6°±0.2°, 17.1°±0.2° and 18.7°±0.2°.

According to another preferred aspect of the present disclosure, the X-ray powder diffraction pattern of crystalline Form I shows one or two or three diffraction peaks at 2theta values of 9.0°±0.2°, 21.0°±0.2° and 25.7°±0.2°. More preferably, the X-ray powder diffraction pattern of crystalline Form I shows diffraction peaks at 2theta values of 9.0°±0.2°, 21.0°±0.2° and 25.7°±0.2°.

In a specific and preferred embodiment of the present disclosure, the X-ray powder diffraction pattern of crystalline Form I shows diffraction peaks at 2theta values of 3.6°±0.2°, 9.0°±0.2°, 12.7°±0.2°, 14.1°±0.2°, 15.6°±0.2°, 17.1°±0.2°, 18.7°±0.2°, 21.0°±0.2° and 25.7°±0.2°.

In another specific and preferred embodiment of the present disclosure, the X-ray powder diffraction pattern of crystalline Form I shows diffraction peaks at 2theta values of 3.6°±0.2°, 9.0°±0.2°, 12.7°±0.2°, 14.1°±0.2°, 15.6°±0.2°, 17.1°±0.2°, 18.7°±0.2°, 21.0°±0.2° and 25.7°±0.2°.

In a preferred embodiment, the X-ray powder diffraction pattern of Form I is substantially as depicted in FIG. 1.

In a preferred embodiment, the crystalline Form I of the present disclosure is a hydrate.

In a preferred embodiment, when performing a DSC analysis, crystalline Form I in the present disclosure begins to lose water when heated to about 69° C. The DSC curve of Form I is depicted in FIG. 2.

In a preferred embodiment, when performing a TGA analysis, crystalline Form I in the present disclosure shows about 3.3% weight loss when heated to 115° C. The TGA curve of Form I is depicted in FIG. 3.

In a specific embodiment, $^1$H NMR spectrum data of crystalline Form I in the present disclosure are shown as follows: $^1$H NMR (400 MHz, CDCl$_3$) δ 7.38 (d, J=8.2 Hz, 1H), 7.21 (dd, J=8.2, 2.1 Hz, 1H), 7.16 (d, J=2.0 Hz, 1H), 7.09 (d, J=8.7 Hz, 2H), 6.86-6.76 (m, 2H), 4.37 (d, J=9.6 Hz, 1H), 4.18 (d, J=9.4 Hz, 1H), 4.10-3.96 (m, 4H), 3.68 (td, J=8.8, 2.3 Hz, 1H), 3.58-3.46 (m, 2H), 2.79 (d, J=2.3 Hz, 1H), 2.51 (d, J=1.9 Hz, 1H), 2.18 (s, 3H), 1.40 (t, J=7.0 Hz, 3H). The $^1$H NMR spectrum is depicted in FIG. 4.

The present disclosure is further to provide processes to prepare crystalline Form I, which are selected from the following methods:

Method 1: Dissolving a solid of Sotagliflozin into an alcohol, ketone or cyclic ether to obtain a Sotagliflozin solution, slowly adding water dropwise into the solution or adding the solution dropwise into water to obtain a solid precipitation, then stirring the mixture at room temperature for 1-72 hours, filtering and drying to obtain a white solid. The white solid is the crystalline Form I of the present disclosure; or Method 2: Adding a solid of Sotagliflozin into water to prepare a suspension, stirring at room temperature for 5-15 days, filtering and drying to obtain the crystalline Form I of the present disclosure.

According to a specific and preferred aspect of the present disclosure, the alcohol, ketone and cyclic ether described in method 1 are preferably methanol, acetone and tetrahydrofuran respectively.

According to the present disclosure, said stirring time in method 1 is preferably 6-72 hours, more preferably 12-72 hours and specifically can be about 24 hours.

According to the present disclosure, said stirring time in method 2 is preferably 6-15 days, more preferably 7-12 days, and further preferably 8 days.

The second scheme adopted by the present disclosure is to provide a crystalline Form II of Sotagliflozin. Using Cu-Kα radiation, the X-ray powder diffraction pattern of crystalline Form II shows diffraction peaks at 2theta values of 3.7°±0.2°, 4.5°±0.2° and 14.6°±0.2°.

Furthermore, the X-ray powder diffraction pattern of crystalline Form II of the present disclosure shows one or more diffraction peaks at 2theta values of 13.4°±0.2°, 18.1°±0.2°, 6.2°±0.2°, 22.0°±0.2°, 10.6°±0.2° and 15.9°±0.2°.

According to a preferred aspect of the present disclosure, the X-ray powder diffraction pattern of crystalline Form II shows one or two or three diffraction peaks at 2theta values of 13.4°±0.2°, 18.1°±0.2° and 6.2°±0.2°. More preferably, the X-ray powder diffraction pattern of crystalline Form II shows diffraction peaks at 2theta values of 13.4°±0.2°, 18.1°±0.2° and 6.2°±0.2°.

According to another preferred aspect of the present disclosure, the X-ray powder diffraction pattern of crystalline Form II shows one or two or three diffraction peaks at 2theta values of 22.0°±0.2°, 10.6°±0.2° and 15.9°±0.2°. More preferably, the X-ray powder diffraction pattern of crystalline Form II shows diffraction peaks at 2theta values of 22.0°±0.2°, 10.6°±0.2° and 15.9°±0.2°.

According to a preferred embodiment of the present disclosure, the X-ray powder diffraction pattern of crystalline Form II shows diffraction peaks at 2theta values of 3.7°±0.2°, 4.5°±0.2°, 6.2°±0.2°, 10.6°±0.2°, 13.4°±0.2°, 14.6°±0.2°, 15.9°±0.2°, 18.1°±0.2° and 22.0°±0.2°.

In a preferred embodiment, the X-ray powder diffraction pattern of Form II is substantially as depicted in FIG. 5.

In a specific embodiment, the crystalline Form II of the present disclosure is a hydrate.

In a preferred embodiment, when performing a DSC analysis, crystalline Form II in the present disclosure begins to lose water when heated to about 62° C. The DSC curve of Form II is depicted in FIG. 6.

In a preferred embodiment, when performing a TGA analysis, crystalline Form II in the present disclosure shows about 5.7% weight loss when heated to 112° C. The TGA curve of Form II is depicted in FIG. 7.

In a specific embodiment, $^1$H NMR spectrum data of crystalline Form II in the present disclosure are shown as follows: $^1$H NMR (400 MHz, CDCl$_3$) δ 7.38 (d, J=8.2 Hz, 1H), 7.21 (dd, J=8.2, 2.1 Hz, 1H), 7.16 (d, J=2.0 Hz, 1H), 7.09 (d, J=8.6 Hz, 2H), 6.85-6.78 (m, 2H), 4.37 (d, J=9.6 Hz, 1H), 4.18 (d, J=9.4 Hz, 1H), 4.11-3.96 (m, 4H), 3.68 (td, J=8.9, 2.3 Hz, 1H), 3.52 (tdd, J=12.1, 9.3, 2.5 Hz, 2H), 2.79 (d, J=2.3 Hz, 1H), 2.51 (d, J=1.9 Hz, 1H), 2.18 (s, 3H), 1.40 (t, J=7.0 Hz, 3H). The $^1$H NMR spectrum is depicted in FIG. 8.

The present disclosure is further to provide processes to prepare crystalline Form II, which are selected from the following methods:

Method 1: Dissolving a solid of Sotagliflozin into an alkyl nitrile to obtain a Sotagliflozin solution, slowly adding water dropwise into the solution or adding the solution dropwise into water to obtain a solid precipitation, then stirring the mixture at room temperature for 1-72 hours, filtering and drying to obtain a white solid. The white solid is namely the crystalline Form II of the present disclosure; or Method 2: Dissolving a solid of Sotagliflozin into a cyclic ether or ester to obtain a Sotagliflozin solution, adding n-heptane dropwise into the solution or adding the solution dropwise into n-heptane to obtain a solid precipitation, then stirring the mixture at room temperature for 1-72 hours, filtering and drying to obtain a white solid. The white solid is the crystalline Form II of the present disclosure; or Method 3: Dissolving a solid of Sotagliflozin into a ketone to obtain a Sotagliflozin solution, adding toluene dropwise into the solution or adding the solution dropwise into toluene to obtain a solid precipitation, then stirring the mixture at room temperature for 1-72 hours, filtering and drying to obtain a white solid. The white solid is the crystalline Form II of the present disclosure; or Method 4: Suspending a solid of Sotagliflozin (preferably the existing crystalline Form 2) into a mixed solvent of a ketone and water or a mixed solvent of an alkyl nitrile and water, then stirring at the temperature of 50-75° C. for 5-20 days, filtering and drying to obtain the crystalline Form II of the present disclosure.

In the processes for preparing crystalline Form II in the present disclosure:

Said alkyl nitrile in method 1 is preferably acetonitrile; said stirring time in method 1 is preferably 6-72 hours, more preferably 6-36 hours, further preferably 12-36 hours, and further more preferably 24-30 hours;

Said cyclic ether and ester in method 2 are preferably tetrahydrofuran and ethyl acetate respectively; said stirring time in method 2 is preferably 6-72 hours, more preferably 6-36 hours, further preferably for 12-36 hours, and further more preferably 24-30 hours;

Said ketone in method 3 is preferably acetone; said stirring time in method 3 is preferably 6-72 hours, more preferably 6-36 hours, further preferably 12-36 hours, and further more preferably 24-30 hours;

Said mixed solvent of ketone and water in method 4 is preferably a mixed solvent of acetone and water, and the volume ratio of ketone and water is 1/2-1/10, preferably 1/3-1/8, and more preferably 1/4-1/6; said mixed solvent of alkyl nitrile and water in method 4 is a mixed solvent of acetonitrile and water, and the volume ratio of nitrile and water is 1/2-1/10, preferably 1/3-1/8, and more preferably 1/4-1/6; said stirring time in method 4 is preferably 8-18 days, more preferably 10-15 days, and specifically 14 days.

The third scheme adopted by the present disclosure is to provide a crystalline Form III of Sotagliflozin. Using Cu-Kα radiation, the X-ray powder diffraction pattern of crystalline Form III shows diffraction peaks at 2theta values of 4.3°±0.2°, 14.6°±0.2° and 19.6°±0.2°.

Furthermore, the X-ray powder diffraction pattern of crystalline Form III of the present disclosure shows one or more diffraction peaks at 2theta values of 4.9°±0.2°, 15.3°±0.2°, 17.5°±0.2°, 12.8°±0.2°, 25.0°±0.2° and 26.4°±0.2°.

According to a preferred aspect of the present disclosure, the X-ray powder diffraction pattern of crystalline Form III shows one or two or three diffraction peaks at 2theta values of 4.9°±0.2°, 15.3°±0.2° and 17.5°±0.2°. More preferably, the X-ray powder diffraction pattern of crystalline Form III shows diffraction peaks at 2theta values of 4.9°±0.2°, 15.3°±0.2° and 17.5°±0.2°.

According to another preferred aspect of the present disclosure, the X-ray powder diffraction pattern of crystalline Form III shows one or two or three diffraction peaks at 2theta values of 12.8°±0.2°, 25.0°±0.2° and 26.4°±0.2°. More preferably, the X-ray powder diffraction pattern of crystalline Form III shows diffraction peaks at 2theta values of 12.8°±0.2°, 25.0°±0.2° and 26.4°±0.2°.

In a preferred embodiment, the X-ray powder diffraction pattern of crystalline Form III of the present disclosure shows diffraction peaks at 2theta values of 4.3°±0.2°, 4.9°±0.2°, 12.8°±0.2°, 14.6°±0.2°, 15.3°±0.2°, 17.5°±0.2°, 25.0°±0.2°, 19.6°±0.2° and 26.4°±0.2°.

In a preferred embodiment, the X-ray powder diffraction pattern of Form III is substantially as depicted in FIG. 9.

In a specific embodiment, the crystalline Form III of the present disclosure is an anhydrate.

In a preferred embodiment, when performing a DSC analysis, crystalline Form III begins to melt when heated to about 131° C. The DSC curve of Form III is depicted in FIG. 10.

In a preferred embodiment, when performing a TGA analysis, crystalline Form III shows about 1.3% weight loss when heated to 125° C. The TGA curve of Form III is depicted in FIG. 11.

In a specific embodiment, $^1$H NMR spectrum data of crystalline Form III in the present disclosure are shown as following: $^1$H NMR (400 MHz, DMSO) δ 7.38 (d, J=8.2 Hz, 1H), 7.26 (d, J=1.9 Hz, 1H), 7.20 (dd, J=8.3, 2.0 Hz, 1H), 7.10 (d, J=8.6 Hz, 2H), 6.83 (d, J=8.6 Hz, 2H), 5.26 (d, J=5.7 Hz, 1H), 5.17 (d, J=4.8 Hz, 1H), 4.98 (d, J=5.7 Hz, 1H), 4.34 (d, J=9.4 Hz, 1H), 4.09 (d, J=9.4 Hz, 1H), 4.03-3.92 (m, 4H), 3.26 (td, J=8.6, 4.9 Hz, 1H), 3.22-3.10 (m, 2H), 2.03 (s, 3H), 1.30 (t, J=7.0 Hz, 3H). The $^1$H NMR spectrum is depicted in FIG. 12.

The present disclosure is further to provide processes to prepare crystalline Form III, which are selected from the following methods:

Method 1: Dissolving a solid of Sotagliflozin into a halogenated alkane, and slowly evaporating at room temperature to obtain a white solid; or Method 2: Dissolving a solid of Sotagliflozin in a mixed solvent of a halogenated alkane and alkane, and slowly evaporating at room temperature to obtain a white solid.

In the processes for preparing crystalline Form III, said halogenated alkane in method 1 is preferably chloroform; the halogenated alkane and the alkane in method 2 are preferably chloroform and n-heptane respectively, and the volume ratio of the halogenated alkane and alkane is 1/1-10/1, more preferably 3/1-6/1, and specifically 4/1.

The fourth scheme adopted by the present disclosure is to provide a crystalline Form V of Sotagliflozin. Using Cu-Kα radiation, the X-ray powder diffraction pattern of crystalline Form V shows diffraction peaks at 2theta values of 5.4°±0.2°, 9.9°±0.2° and 19.7°±0.2°.

Furthermore, the X-ray powder diffraction pattern of crystalline Form V of the present disclosure shows one or more diffraction peaks at 2theta values of 12.8°±0.2°, 13.6°±0.2°, 15.1°±0.2°, 6.5°±0.2°, 18.2°±0.2° and 20.4°±0.2°.

According to a preferred aspect of the present disclosure, the X-ray powder diffraction pattern of crystalline Form V shows one or two or three diffraction peaks at 2theta values of 12.8°±0.2°, 13.6°±0.2° and 15.1°±0.2°. Preferably, the X-ray powder diffraction pattern of crystalline Form V shows diffraction peaks at 2theta values of 12.8°±0.2°, 13.6°±0.2° and 15.1°±0.2°.

According to another preferred aspect of the present disclosure, the X-ray powder diffraction pattern of crystalline Form V shows one or two or three diffraction peaks at 2theta values of 6.5°±0.2°, 18.2°±0.2° and 20.4°±0.2°. More preferably, the X-ray powder diffraction pattern of crystalline Form V shows diffraction peaks at 2theta values of 6.5°±0.2°, 18.2°±0.2° and 20.4°±0.2°.

In a preferred embodiment, the X-ray powder diffraction pattern of crystalline Form V of the present disclosure shows diffraction peaks at 2theta values of 5.4°±0.2°, 6.5°±0.2°, 9.9°±0.2°, 12.8°±0.2°, 13.6°±0.2°, 15.1°±0.2°, 18.2°±0.2°, 19.7°±0.2° and 20.4°±0.2°.

In a preferred embodiment, the X-ray powder diffraction pattern of crystalline Form V of the present disclosure is substantially as depicted in FIG. 13.

In a specific embodiment, the crystalline Form V of the present disclosure is a hydrate.

In a preferred embodiment, when performing a DSC analysis, crystalline Form V of the present disclosure begins to lose water when heated to about 30° C. The DSC curve of Form V is depicted in FIG. 14.

In a preferred embodiment, when performing a TGA analysis, crystalline Form V shows about 12.7% weight loss when heated to 115° C. The TGA curve of crystalline Form V is depicted in FIG. 15.

In a specific embodiment, $^1$H NMR spectrum data of crystalline Form V in the present disclosure are shown as following: $^1$H NMR (400 MHz, CDCl$_3$) δ 7.38 (d, J=8.2 Hz, 1H), 7.21 (dd, J=8.2, 2.1 Hz, 1H), 7.16 (d, J=2.0 Hz, 1H), 7.09 (d, J=8.6 Hz, 2H), 6.82 (d, J=8.6 Hz, 2H), 4.37 (d, J=9.6 Hz, 1H), 4.18 (d, J=9.4 Hz, 1H), 4.11-3.95 (m, 4H), 3.72-3.65 (m, 1H), 3.52 (ddd, J=21.5, 9.3, 2.4 Hz, 2H), 2.81 (d, J=2.3 Hz, 1H), 2.52 (d, J=1.9 Hz, 1H), 2.18 (s, 3H), 1.40 (t, J=7.0 Hz, 3H). The $^1$H NMR spectrum is depicted in FIG. 16.

The present disclosure is further to provide a process to prepare crystalline Form V, which comprise: dissolving a solid of Sotagliflozin into a mixed solvent of an alcohol and water heated to 40-70° C. to obtain a clear solution, and transferring the obtained clear solution to a cool environment with the temperature of 0-10° C., stirring for 12-96 hours, filtering and drying to obtain a white solid.

In the process for preparing crystalline Form V, the temperature of heated mixed solvent is preferably 50-60° C.; the temperature of cool environment is preferably about 5° C.; the alcohol is preferably methanol; the volume ratio of alcohol (methanol) and water is preferably 2/1-2/3, more preferably 1/1; in the cooling environment, the stirring time is preferably 36-96 hours, more preferably 48-96 hours, and most preferably 72-84 hours.

The fifth scheme adopted by the present disclosure is to provide a crystalline Form VI of Sotagliflozin. Using Cu-Kα radiation, the X-ray powder diffraction pattern of crystalline Form VI shows diffraction peaks at 2theta values of 4.8°±0.2°, 9.5°±0.2° and 14.5°±0.2°.

Furthermore, the X-ray powder diffraction pattern of crystalline Form VI of the present disclosure shows one or more diffraction peaks at 2theta values of 11.1°±0.2°, 19.1°±0.2°, 21.5°±0.2°, 7.7°±0.2°, 20.0°±0.2° and 25.4°±0.2°.

According to a preferred aspect of the present disclosure, the X-ray powder diffraction pattern of crystalline Form VI shows one or two or three diffraction peaks at 2theta values of 11.1°±0.2°, 19.1°±0.2° and 21.5°±0.2°. More preferably, the X-ray powder diffraction pattern of crystalline Form VI shows diffraction peaks at 2theta values of 11.1°±0.2°, 19.1°±0.2° and 21.5°±0.2°.

According to another preferred aspect of the present disclosure, the X-ray powder diffraction pattern of crystalline Form VI shows one or two or three diffraction peaks at 2theta values of 7.7°±0.2°, 20.0°±0.2° and 25.4°±0.2°. More preferably, the X-ray powder diffraction pattern of crystalline Form VI shows diffraction peaks at 2theta values of 7.7°±0.2°, 20.0°±0.2° and 25.4°±0.2°.

In a preferred embodiment, the X-ray powder diffraction pattern of crystalline Form VI of the present disclosure shows diffraction peaks at 2theta values of 4.8°±0.2°, 7.7°±0.2°, 9.5°±0.2°, 11.1°±0.2°, 14.5°±0.2°, 19.1°±0.2°, 20.0°±0.2°, 21.5°±0.2° and 25.4°±0.2°.

In a preferred embodiment, the X-ray powder diffraction pattern of crystalline Form VI of the present disclosure is substantially as depicted in FIG. 17.

In a specific embodiment, the crystalline Form VI of the present disclosure is a hydrate.

In a preferred embodiment, when performing a DSC analysis, crystalline Form VI of the present disclosure begins to lose water when heated to about 80° C. The DSC curve of Form VI is depicted in FIG. 18.

In a preferred embodiment, when performing a TGA analysis, crystalline Form VI shows about 3.6% weight loss when heated to 116° C. The TGA curve of crystalline Form VI is depicted in FIG. 19.

In a specific embodiment, $^1$H NMR spectrum data of crystalline Form VI in the present disclosure are shown as following: $^1$H NMR (400 MHz, CDCl$_3$) δ 7.38 (d, J=8.2 Hz, 1H), 7.21 (dd, J=8.2, 2.1 Hz, 1H), 7.17 (d, J=2.0 Hz, 1H), 7.09 (d, J=8.7 Hz, 2H), 6.85-6.79 (m, 2H), 4.37 (d, J=9.6 Hz, 1H), 4.18 (d, J=9.4 Hz, 1H), 4.11-3.96 (m, 4H), 3.68 (t, J=9.0 Hz, 1H), 3.58-3.46 (m, 2H), 2.83 (s, 1H), 2.53 (d, J=1.6 Hz, 1H), 2.18 (s, 3H), 1.40 (t, J=7.0 Hz, 3H). The $^1$H NMR spectrum is depicted in FIG. 20.

The present disclosure is further to provide a process to prepare crystalline Form VI, which comprise: suspending a solid of Sotagliflozin into water, stirring the suspension at the temperature of 35-65° C. for 24-96 hours, filtering and drying to obtain the crystalline Form VI.

In the process for preparing crystalline Form VI, the suspension was stirred preferably at the temperature of 45-55° C., more preferably at about 50° C.; the stirring time is preferably 36-84 hours, more preferably 48 to 84 hours, and most preferably about 72 hours.

The sixth scheme adopted by the present disclosure is to provide a crystalline Form VII of Sotagliflozin. Using Cu-Kα radiation, the X-ray powder diffraction pattern of crystalline Form VII shows diffraction peaks at 2theta values of 10.5°±0.2°, 13.8°±0.2° and 15.8°±0.2°.

Furthermore, the X-ray powder diffraction pattern of crystalline Form VII of the present disclosure shows one or more diffraction peaks at 2theta values of 16.7°±0.2°, 20.3°±0.2°, 22.6°±0.2°, 6.7°±0.2°, 18.5°±0.2° and 19.1°±0.2°.

According to a preferred aspect of the present disclosure, the X-ray powder diffraction pattern of crystalline Form VII shows one or two or three diffraction peaks at 2theta values of 16.7°±0.2°, 20.3°±0.2° and 22.6°±0.2°. More preferably, the X-ray powder diffraction pattern of crystalline Form VII shows diffraction peaks at 2theta values of 16.7°±0.2°, 20.3°±0.2° and 22.6°±0.2°.

According to another preferred aspect of the present disclosure, the X-ray powder diffraction pattern of crystalline Form VII shows one or two or three diffraction peaks at 2theta values of 6.7°±0.2°, 18.5°±0.2° and 19.1°±0.2°. More preferably, the X-ray powder diffraction pattern of crystalline Form VII shows diffraction peaks at 2theta values of 6.7°±0.2°, 18.5°±0.2° and 19.1°±0.2°.

In a preferred embodiment, the X-ray powder diffraction pattern of crystalline Form VII of the present disclosure shows diffraction peaks at 2theta values of 6.7°±0.2°, 10.5°±0.2°, 13.8°±0.2°, 15.8°±0.2°, 16.7°±0.2°, 18.5°±0.2°, 19.1°±0.2°, 20.3°±0.2° and 22.6°±0.2°.

In a preferred embodiment, the X-ray powder diffraction pattern of crystalline Form VII of the present disclosure is substantially as depicted in FIG. 21.

In a preferred embodiment, when performing a DSC analysis, crystalline Form VII of the present disclosure begins to melt when heated to about 120° C. The DSC curve of Form VII is depicted in FIG. 22.

In a preferred embodiment, when performing a TGA analysis, crystalline Form VII shows about 1.9% weight loss when heated to 114° C. The TGA curve of crystalline Form VII is depicted in FIG. 23.

In a specific embodiment, $^1$H NMR spectrum data of crystalline Form VII in the present disclosure are shown as following: $^1$H NMR (400 MHz, CDCl$_3$) δ 7.38 (d, J=8.2 Hz, 1H), 7.21 (dd, J=8.2, 2.1 Hz, 1H), 7.16 (d, J=2.1 Hz, 1H), 7.09 (d, J=8.7 Hz, 2H), 6.85-6.79 (m, 2H), 4.37 (d, J=9.6 Hz, 1H), 4.18 (d, J=9.4 Hz, 1H), 4.10-3.97 (m, 4H), 3.71-3.64 (m, 1H), 3.58-3.45 (m, 2H), 2.81 (d, J=2.2 Hz, 1H), 2.53 (d, J=1.9 Hz, 1H), 2.18 (s, 3H), 1.40 (t, J=7.0 Hz, 3H). The $^1$H NMR spectrum is depicted in FIG. 24.

The present disclosure is further to provide a process to prepare crystalline Form VII, which comprise the following steps: heating the crystalline Form II of Sotagliflozin to 90-100° C. with a heating rate of 5-10° C./min, and keeping for 0.5-5 minutes at the temperature of 90-100° C. to obtain a white solid.

In a specific embodiment, crystalline Form II was heated to 90° C. with a heating rate of 10° C./min, and kept at 90° C. for 0.5 min to obtain a white solid, which was crystalline Form VII of the present disclosure.

The seventh scheme adopted by the present disclosure is to provide a crystalline Form VIII of Sotagliflozin. Using Cu-Kα radiation, the X-ray powder diffraction pattern of crystalline Form VIII shows diffraction peaks at 2theta values of 6.2°±0.2°, 10.9°±0.2° and 17.7°±0.2°.

Furthermore, the X-ray powder diffraction pattern of crystalline Form VIII of the present disclosure shows one or more diffraction peaks at 2theta values of 6.2°±0.2°, 10.4°±0.2°, 10.9°±0.2°, 14.9°±0.2°, 15.7°±0.2°, 17.7°±0.2°, 18.8°±0.2°, 20.9°±0.2° and 24.1°±0.2°.

According to a preferred aspect of the present disclosure, the X-ray powder diffraction pattern of crystalline Form VIII shows one or two or three diffraction peaks at 2theta values of 14.9°±0.2°, 15.7°±0.2° and 20.9°±0.2°. More preferably, the X-ray powder diffraction pattern of crystalline Form VIII shows diffraction peaks at 2theta values of 14.9°±0.2°, 15.7°±0.2° and 20.9°±0.2°.

According to another preferred aspect of the present disclosure, the X-ray powder diffraction pattern of crystalline Form VIII shows one or two or three diffraction peaks at 2theta values of 10.4°±0.2°, 18.8°±0.2° and 24.1°±0.2°. More preferably, the X-ray powder diffraction pattern of crystalline Form VII shows diffraction peaks at 2theta values of 10.4°±0.2°, 18.8°±0.2° and 24.1°±0.2°.

In a preferred embodiment, the X-ray powder diffraction pattern of crystalline Form VIII of the present disclosure shows diffraction peaks at 2theta values of 6.2°±0.2°, 10.4°±0.2°, 10.9°±0.2°, 14.9°±0.2°, 15.7°±0.2°, 17.7°±0.2°, 18.8°±0.2°, 20.9°±0.2° and 24.1°±0.2°.

In a preferred embodiment, the X-ray powder diffraction pattern of crystalline Form VIII of the present disclosure is substantially as depicted in FIG. 25.

In a preferred embodiment, when performing a DSC analysis, crystalline Form VIII of the present disclosure begins to lose solvent when heated to about 91° C. The DSC curve of Form VIII is depicted in FIG. 26.

The present disclosure is further to provide a process to prepare crystalline Form VIII, which comprise: heating the crystalline Form V solid to the temperature of 60-80° C., and keeping at the temperature for more than 2 minutes, wherein the obtained solid is the crystalline Form VIII of the present disclosure. Preferably, the heating rate is 10° C./min, and the heating temperature is about 65° C.

Crystalline Form I, crystalline Form II, crystalline Form III, crystalline Form V, crystalline Form VI, crystalline Form VII and crystalline Form VIII of Sotagliflozin have the following beneficial properties:

① Good stability;
② Simple process for preparation and good repeatability when scaling up;
③ Good crystallinity;

Additionally, compared with the existing crystalline From 2, crystalline Form I and Form II are more stable in high water activity environment. Compared with the existing crystalline From 2, crystalline Form I and Form VI have better mechanical stability, and is more suitable for drug production and storage. Moreover, the existing crystalline Form 2 has the disadvantages of broad particle size distribution, agglomeration phenomena, and needle-like shape. While crystalline Form I, Form V, Form VII, and Form VIII have uniform particle size distribution, which helps to simplify the post-treatment of production process and improve quality control. Compared with the existing crystalline Form 2, crystalline Form II, Form III, Form VII and Form VIII have higher solubility, which facilitate drug absorption.

The present disclosure is to provide crystalline Form I, Form II, Form III, Form V, Form VI, Form VII and Form VIII to overcome the deficiencies of prior art. These novel crystalline forms have at least one of following advantages: high solubility, simple process for preparation, low toxicity solvent used in the process, good crystallinity, optimal particle morphology, low hygroscopicity, better flowability and stability.

In the present disclosure, "crystal" or "crystalline form" refers to the crystal or the crystal form being identified by the X-ray diffraction pattern shown herein. The person skilled in the art are able to understand that physical and chemical properties discussed herein can be characterized and the experimental errors depend on the conditions of instruments, the sample preparations and the purity of samples. In particular, those skilled in the art generally know that the X-ray diffraction pattern usually may change with the change of the experimental conditions. It is necessary to point out that, the relative intensity of the X-ray diffraction pattern is likely to change with the change of the experimental conditions; therefore, the sequence of peak intensity cannot be regarded as the only or the determining factor. Moreover, the experimental error of the peak positions is 5% or less, so such error should be considered and generally the allowed error is ±0.2°. In addition, due to the effect of the experimental factors including sample height, positions may have an overall shifting; generally, certain shifting is allowed. Hence, those skilled in the art may understand that, it is unnecessary that the X-ray diffraction pattern of a crystal form in the present disclosure should be exactly the same with X-ray diffraction patterns of the example shown herein. Any crystal forms whose X-ray diffraction patterns have the same or similar characteristic peaks should be within the scope of the present disclosure. Those skilled in the art can compare the patterns shown in the present disclosure with that of an unknown crystal form in order to identify whether these two groups of patterns reflect the same or different crystal forms.

"Crystalline form" and "polymorphic form" as well as other related terms in the present disclosure refer to a specific crystal form of solid compounds. The differences in the physical and chemical properties of the polymorphic forms may include stability during storage, compressibility, density, dissolution rate, etc. In extreme cases, the difference in solubility or dissolution rate may result in drugs with low efficiency and toxicity.

The term "effective treatment amount" or "therapeutically effective amount" as used herein means that amount of an active compound that elicits the biological or medicinal response in a tissue, system, animal or human that is being sought by a researcher, veterinarian, medical doctor, or other clinician.

In some embodiments, novel crystalline forms of Sotagliflozin, including crystalline Form I, Form II, Form III, Form V, Form VI, Form VII and Form VIII in the present disclosure, are pure and substantially free of any other crystalline forms. In the present disclosure, when the term "substantially free" is used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the numerical value and the scope of the present disclosure should not be narrowly understood as a value or numerical value range itself. It should be understood by those skilled in the art that the specific numerical value can be varied or modified in specific technical environment without departing substantially from the spirit and principles of the disclosure, and the range of variation which can be expected by one of skilled in the art is represented by the term "about".

The crystalline Form I, Form II, Form III, Form V, Form VI, Form VII or Form VIII of Sotagliflozin provided in the present disclosure has favorable properties that are suitable for the above dosage form.

The present disclosure is further to provide the use of one or more of crystalline Form I, Form II, Form III, Form V, Form VI, Form VII and Form VIII of Sotagliflozin for preparing drugs inhibiting SGLT, especially SGLT-2.

The present disclosure is further to provide a pharmaceutical composition. Said pharmaceutical composition comprises a therapeutically effective amount of crystalline Form I, Form II, Form III, Form V, Form VI, Form VII, Form VIII of Sotagliflozin or any combinations thereof, and pharmaceutically acceptable carrier, diluent or excipient. Preferably, said pharmaceutical composition is used for the prevention and/or treatment of diabetes. Said pharmaceutical compositions may be prepared according to known methods in this field, and these methods are not described here.

DETAILED DESCRIPTION OF THE DISCLOSURE

Figure 1:
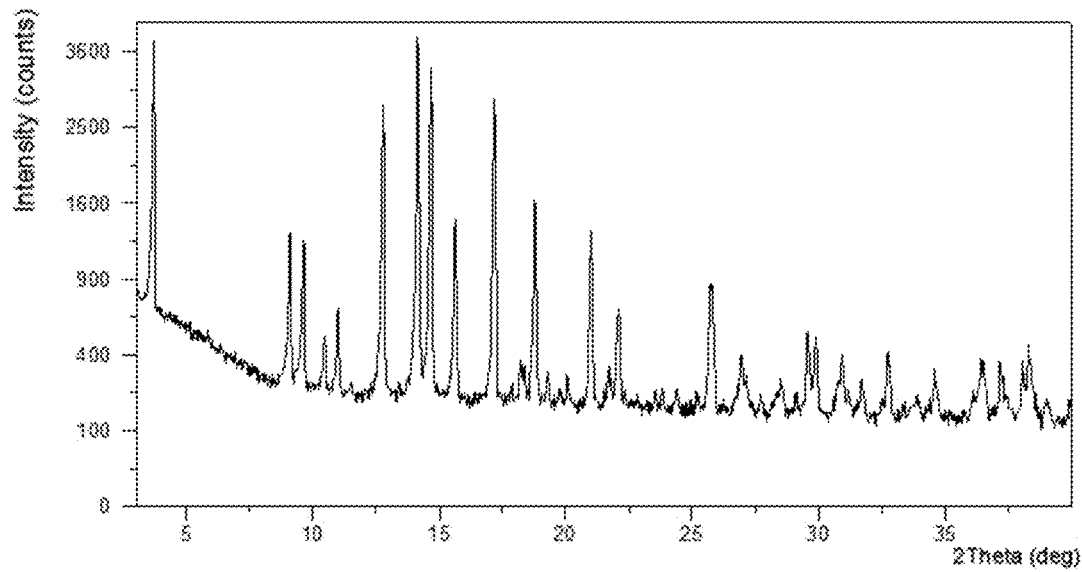
FIG. 1 shows an X-ray Powder Diffraction pattern of crystalline Form I in example 1.

The present disclosure is further illustrated by the following examples which describe the preparation and use of the crystalline forms of the disclosure in detail. It is obvious to those skilled in the art that many changes in the materials and methods can be accomplished without departing from the scope of the disclosure.

The abbreviations used in the present disclosure are explained as follows:
XRPD: X-ray Powder Diffraction
DSC: Differential Scanning calorimetry
TGA: Thermal Gravimetric Analysis
DVS: Dynamic Vapor Sorption
PSD: Particle Size Distribution
PLM: Polarized Light microscopy
$^1$H NMR: proton Nuclear Magnetic Resonance
MV: Average particle size based on volume
D10: The D10 describes the diameter where 10% of the distribution has a smaller particle size.
D50: The D50 describes the diameter where 50% of the distribution has a smaller particle size. The median is also called D50.
D90: The D90 describes the diameter where 90% of the distribution has a smaller particle size.

The instruments and methods used to collect data:

X-ray powder diffraction (XRPD) pattern in the present disclosure is acquired by a Panalytical Empyrean X-ray powder diffractometer. The parameters of the X-ray powder diffraction method of the present disclosure are as follows:
X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree The data of a differential scanning calorimetry (DSC) are acquired by a TA Instruments Q2000 MDSC, with Thermal Advantage as instrument control software and Universal Analysis as analysis software. Generally, 1~10 mg of sample is put into an aluminum crucible (unless otherwise specified, the aluminum crucible is covered). The temperature of sample was raised from room temperature to 300° C. with a heating rate of 10° C./min under the protection of dry nitrogen with a flow rate of 50 mL/min, while the TA software records the heat change of the sample during the heating process. In the present disclosure, melting point is reported based on DSC onset temperature.

The data of thermogravimetric analysis (TGA) are acquired by a TA Instruments Q5000 TGA, with Thermal Advantage as instrument control software and Universal Analysis as analysis software. Generally, 5~15 mg of sample is put into a platinum crucible. The temperature of sample was raised from room temperature to 300° C. with a heating rate of 10° C./min under the protection of dry nitrogen with a flow rate of 50 mL/min, while the TA software records the weight change of the sample during the heating process. The water content of the crystalline forms in the present disclosure is estimated and calculated according to the weight loss in TGA. As is known by those skilled in the art, weight loss in TGA is the reference of water content in crystalline forms, but does not necessarily represent the number of water molecules contained in crystalline forms.

Dynamic Vapor Sorption (DVS) is measured via a SMS (Surface Measurement Systems Ltd.) intrinsic DVS. Typical Parameters for DVS test are as follows:
Temperature: 25° C.
Gas and flow rate: N$_2$, 200 mL/min
dm/dt: 0.002%/min
Relative Humidity (RH) range: 20% RH-95% RH-0% RH-95% RH Proton Nuclear Magnetic Resonance ($^1$HNMR) spectrum data are collected from a Bruker Avance II DMX 400M HZ NMR spectrometer. 1-5 mg of sample was weighed, dissolved in 0.5 mL of deuterated dimethyl sulfoxide or deuterochloroform to obtain a solution with the concentration of 2-10 mg/mL.

The result of particle size distribution (PSD) in the present disclosure was acquired by laser particle size analyzer with S3500 model from Microtrac Company. The Microtrac S3500 is equipped with a SDC (Sample Delivery Controller) sampling system. This experiment uses a wet method and the dispersion medium is Isopar G. The method and parameters of the laser particle size analyzer are as follows:

| | |
|---|---|
| Size distribution: Volume distribution | Run time: 10 s |
| Dispersion medium: Isopar G | Particle coordinates: Standard |
| Run number: 3 | Disperse medium refractive index: 1.42 |
| Transparency: Transparent | Residual: Enabled |
| Particle refractive index: 1.5 | Flow rate: 60%* |
| Particle shape: Irregular | Filtration: Enabled |
| Ultrasonic power: 30 W | Ultrasonic time: 30 s |

*Flow rate 60% is 60% of 65 mL/s.

The HPLC method parameters for purity test in the present disclosure are as follows:

| | |
|---|---|
| HPLC | Agilent 1100 with DAD detector |
| Column | Waters Xbridge C$_{18}$, 150 × 4.6 mm, 5 μm |
| Mobile Phase | A: 0.1% TFA (trifluoroacetic acid) in H$_2$O |
| | B: 0.1% TFA (trifluoroacetic acid) in acetonitrile |

| | Time (min) | % B |
|---|---|---|
| Gradient | 0.0 | 30 |
| | 20.0 | 80 |
| | 25.0 | 80 |
| | 26.0 | 30 |
| | 32.0 | 30 |

| | |
|---|---|
| Time | 32.0 min |
| Flow rate | 1.0 mL/min |
| Injection Volume | 5 μL |
| Detection wavelength | 225 nm |
| Column Temperature | 40° C. |
| Diluent | ACN:H$_2$O = 1:1 |

The HPLC method parameters for solubility test in the present disclosure are as follows:

| | |
|---|---|
| HPLC | Agilent 1100 with DAD detector |
| Column | Waters XBridge C18 150 * 4.6 mm, 5 μm |
| Mobile Phase | H$_2$O:ACN:TFA = 45:55:0.1 |
| Time | 6.0 min |
| Flow rate | 1.0 mL/min |
| Injection Volume | 5 μL |
| Detection wavelength | UV at 230 nm, reference 500 nm |
| Column Temperature | 40° C. |
| Diluent | ACN:H$_2$O = 1:1 |

Unless otherwise specified, the following examples were conducted at room temperature.

Raw materials of Sotagliflozin used in the following examples are prepared by the method disclosed in CN101343296B or purchased from market, or prepared according to the method in the present invention.

EXAMPLE 1 PREPARATION OF FORM I OF SOTAGLIFLOZIN 456.4 mg of Sotagliflozin was added into a 20-mL glass vial followed by adding 2.0 mL of acetone to form a clear solution. The clear solution was slowly added into 18 mL of water under magnetic stirring, and white solid precipitated immediately. The sample was stirred at room temperature for 3 days, then filtered and dried to obtain a white solid.

The solid obtained in example 1 conformed to Form I. The XRPD data were listed in Table 1, and the XRPD pattern was substantially as depicted in FIG. 1.

TABLE 1

| 2theta (°) | d spacing | Intensity % |
|---|---|---|
| 3.64 | 24.25 | 84.09 |
| 9.04 | 9.78 | 28.39 |
| 9.58 | 9.23 | 25.55 |
| 10.41 | 8.49 | 7.12 |
| 10.95 | 8.08 | 12.55 |
| 12.73 | 6.95 | 70.82 |
| 14.11 | 6.28 | 100.00 |
| 14.62 | 6.06 | 83.36 |
| 15.58 | 5.69 | 3.73 |
| 17.13 | 5.18 | 72.62 |
| 18.16 | 4.88 | 5.03 |
| 18.74 | 4.74 | 40.78 |
| 19.25 | 4.61 | 3.29 |
| 20.02 | 4.44 | 3.16 |
| 20.95 | 4.24 | 31.08 |
| 21.64 | 4.11 | 4.12 |
| 22.03 | 4.03 | 14.09 |
| 23.66 | 3.76 | 0.56 |
| 24.33 | 3.66 | 1.27 |
| 25.65 | 3.47 | 18.25 |
| 26.89 | 3.32 | 6.76 |
| 28.48 | 3.13 | 3.18 |
| 29.10 | 3.07 | 2.16 |
| 29.51 | 3.03 | 10.36 |
| 29.84 | 2.99 | 9.77 |
| 30.88 | 2.90 | 6.85 |
| 31.65 | 2.83 | 3.84 |
| 32.70 | 2.74 | 7.68 |
| 34.55 | 2.60 | 5.43 |
| 36.45 | 2.47 | 6.05 |
| 37.13 | 2.42 | 6.77 |
| 38.02 | 2.37 | 5.82 |
| 38.26 | 2.35 | 8.16 |
| 38.97 | 2.31 | 1.82 |

EXAMPLE 2 PREPARATION OF FORM I OF SOTAGLIFLOZIN 41.4 mg of Sotagliflozin was added into a 5-mL glass vial followed by adding 0.2 mL of acetone to form a clear solution. White precipitation appeared after 2.0 mL of H$_2$O being slowly added under magnetic stirring. The sample was stirred for 24 hours, then filtered and dried to obtain a white solid.

Figure 2:
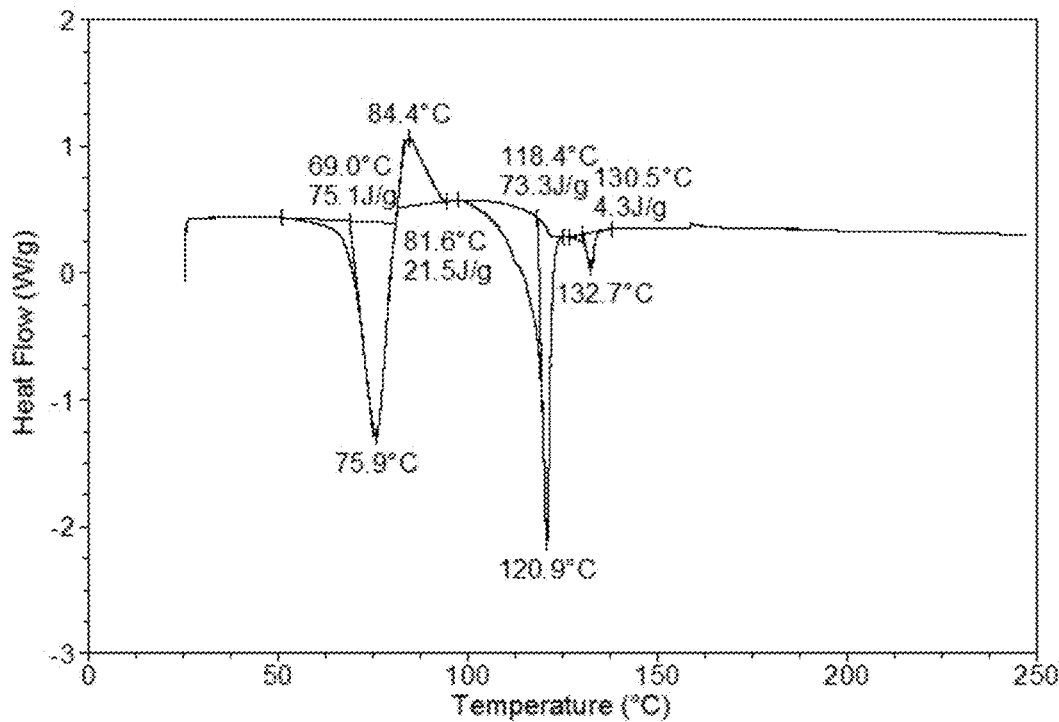
FIG. 2 shows a Differential Scanning calorimetry curve of crystalline Form I in example 2.
Figure 3:
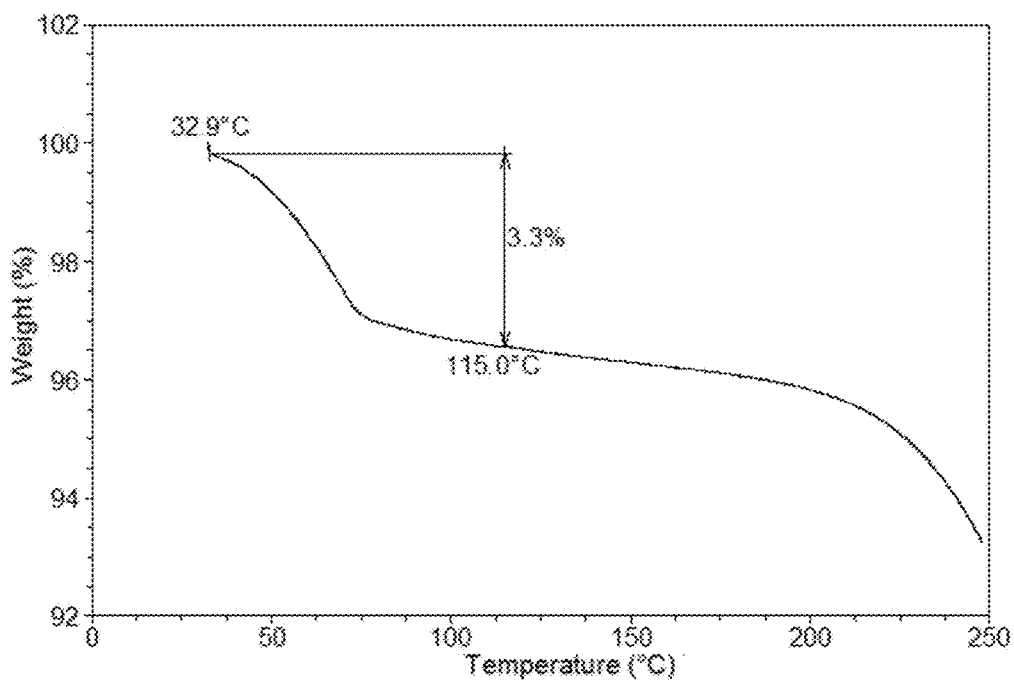
FIG. 3 shows a Thermal Gravimetric Analysis curve of crystalline Form I in example 2.
Figure 4:
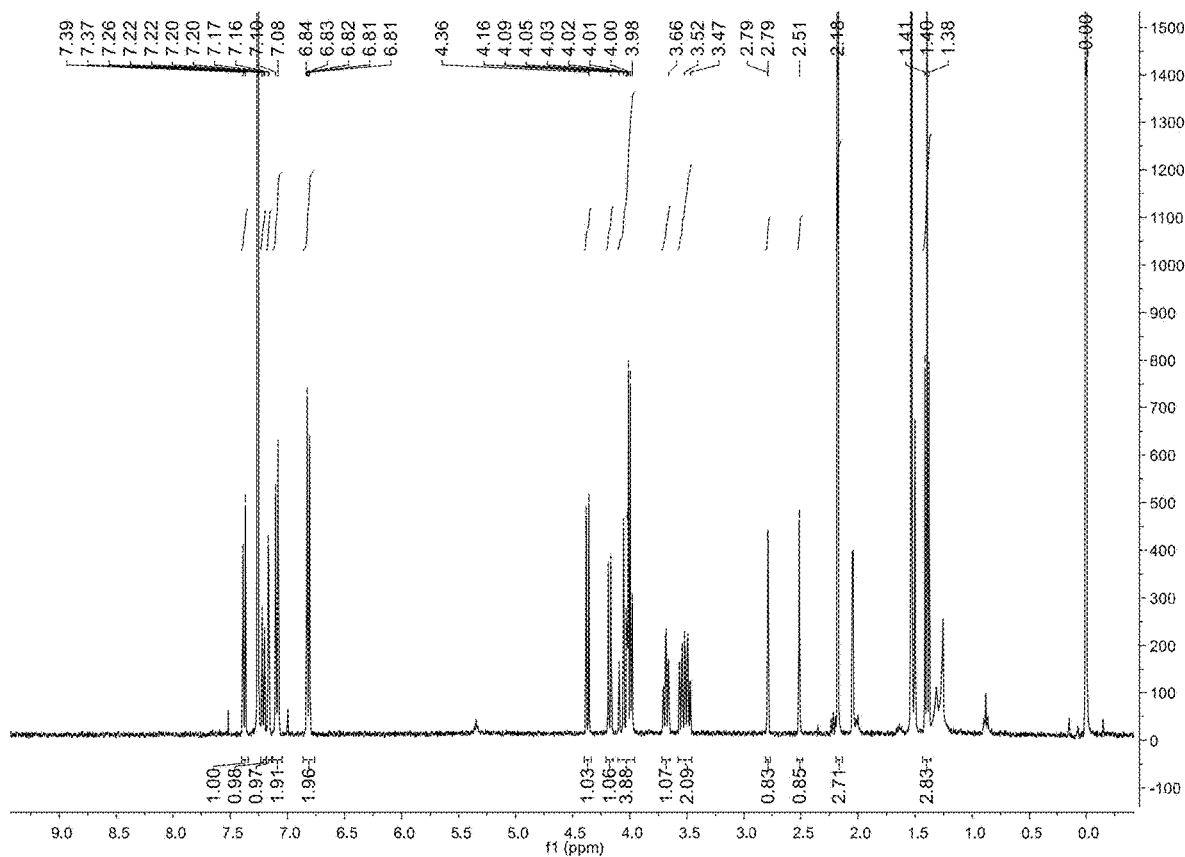
FIG. 4 shows a $^1$H NMR spectrum of crystalline Form I in example 2.
Figure 27:
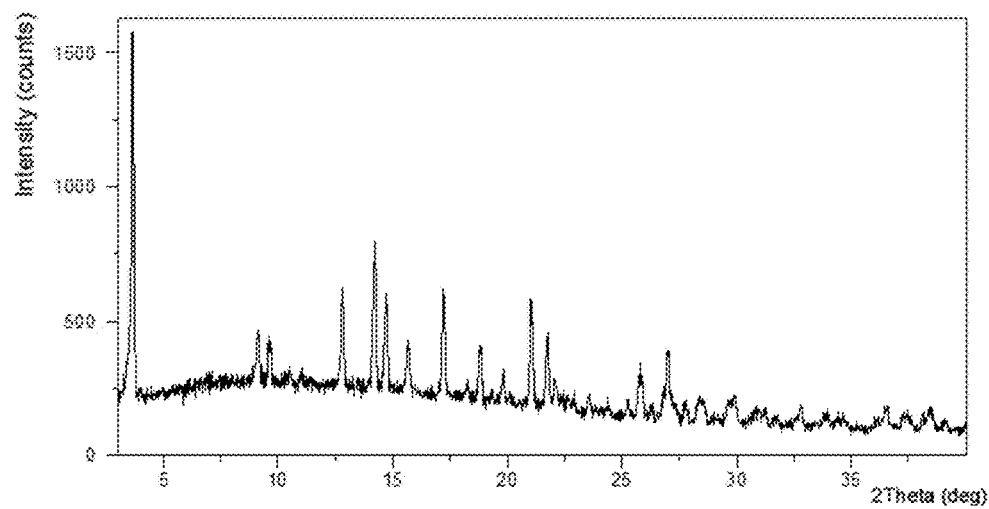
FIG. 27 shows an X-ray Powder Diffraction pattern of crystalline Form I in example 2.

The solid obtained in example 2 conformed to Form I. The XRPD data were listed in Table 2, and the XRPD pattern was substantially as depicted in FIG. 27. The DSC curve was displayed in FIG. 2. The TGA curve was displayed in FIG. 3. The $^1$H NMR spectrum was displayed in FIG. 4.

TABLE 2

| 2theta (°) | d spacing | Intensity % |
|---|---|---|
| 3.63 | 24.36 | 100.00 |
| 9.11 | 9.71 | 13.21 |
| 9.61 | 9.21 | 11.92 |
| 12.79 | 6.92 | 27.92 |
| 14.18 | 6.24 | 38.88 |
| 14.65 | 6.05 | 25.53 |
| 15.65 | 5.66 | 14.91 |
| 17.15 | 5.17 | 26.56 |
| 18.81 | 4.72 | 15.44 |
| 19.78 | 4.49 | 8.52 |
| 21.05 | 4.22 | 26.59 |
| 21.74 | 4.09 | 20.20 |
| 22.05 | 4.03 | 7.39 |
| 23.52 | 3.78 | 4.64 |
| 25.70 | 3.47 | 10.65 |
| 26.92 | 3.31 | 19.09 |
| 27.69 | 3.22 | 3.52 |
| 28.44 | 3.14 | 5.24 |
| 29.59 | 3.02 | 5.66 |
| 29.89 | 2.99 | 6.85 |
| 30.97 | 2.89 | 2.83 |
| 32.76 | 2.73 | 5.37 |
| 33.86 | 2.65 | 3.17 |
| 34.69 | 2.59 | 1.96 |
| 36.55 | 2.46 | 6.01 |
| 37.27 | 2.41 | 3.91 |
| 38.41 | 2.34 | 5.52 |
| 39.03 | 2.31 | 2.15 |

EXAMPLE 3 PREPARATION OF FORM I OF SOTAGLIFLOZIN 8.1 mg of Sotagliflozin was added into a 1.5-mL glass vial followed by adding 0.2 mL of MeOH to form a clear solution. White precipitation appeared after 1.5 mL of H$_2$O being slowly added under magnetic stirring. The sample was stirred at room temperature for 24 hours, then filtered and dried to obtain a white solid.

Figure 28:
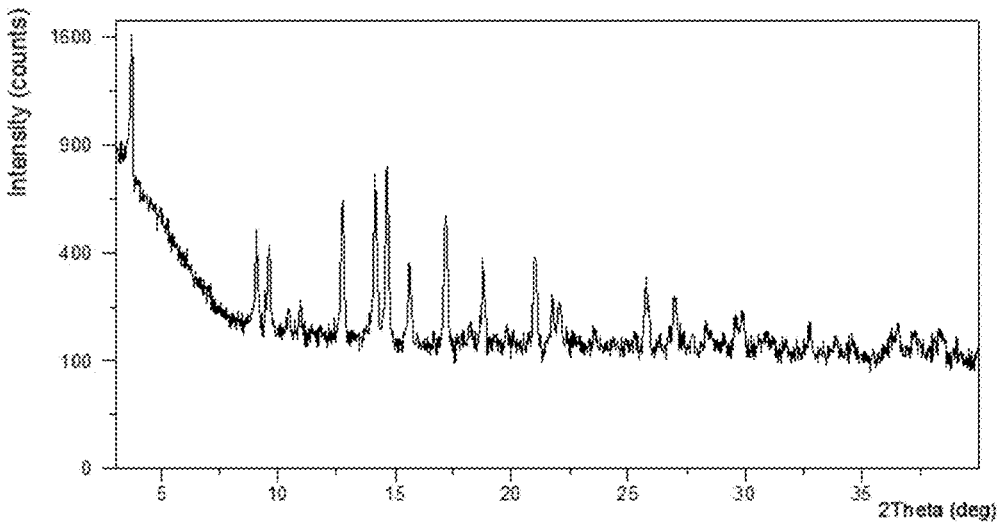
FIG. 28 shows an X-ray Powder Diffraction pattern of crystalline Form I in example 3.

The solid obtained in example 3 conformed to Form I. The XRPD data were listed in Table 3, and the XRPD pattern was substantially as depicted in FIG. 28.

TABLE 3

| 2theta (°) | d spacing | Intensity % |
|---|---|---|
| 3.67 | 24.10 | 100.00 |
| 9.02 | 9.80 | 26.87 |
| 9.57 | 9.24 | 23.03 |
| 10.92 | 8.10 | 6.98 |
| 12.72 | 6.96 | 43.51 |
| 14.09 | 6.28 | 57.44 |
| 14.61 | 6.06 | 58.67 |
| 15.58 | 5.69 | 21.55 |
| 17.12 | 5.18 | 38.86 |
| 18.73 | 4.74 | 23.59 |
| 20.95 | 4.24 | 24.07 |
| 21.70 | 4.10 | 12.42 |
| 22.04 | 4.03 | 9.06 |
| 25.70 | 3.47 | 14.94 |
| 26.92 | 3.31 | 10.69 |
| 28.38 | 3.14 | 3.43 |
| 29.52 | 3.03 | 5.47 |
| 29.87 | 2.99 | 6.66 |
| 36.43 | 2.47 | 5.71 |
| 37.27 | 2.41 | 4.55 |
| 38.34 | 2.35 | 5.39 |

EXAMPLE 4 PREPARATION OF FORM I OF SOTAGLIFLOZIN 8.5 mg of Sotagliflozin was added into a 1.5-mL glass vial followed by adding 0.075 mL of acetone to form a clear solution. White precipitation appeared after 1.5 mL of H₂O being slowly added under magnetic stirring. The sample was stirred at room temperature for 24 hours, then filtered and dried to obtain a white solid.

Figure 29:
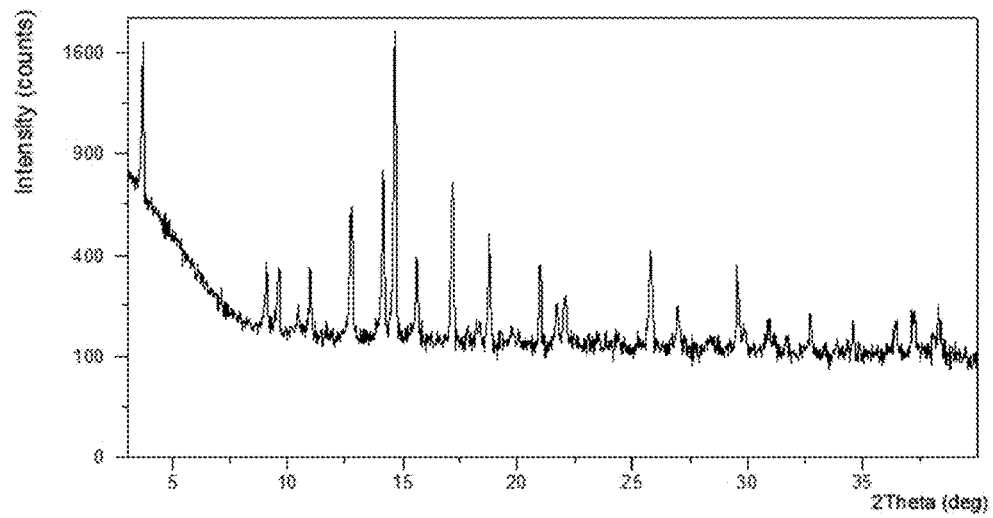
FIG. 29 shows an X-ray Powder Diffraction pattern of crystalline Form I in example 4.

The solid obtained in example 4 conformed to Form I. The XRPD data were listed in Table 4, and the XRPD pattern was substantially as depicted in FIG. 29.

TABLE 4

| 2theta (°) | d spacing | Intensity % |
|---|---|---|
| 3.65 | 24.23 | 75.50 |
| 9.04 | 9.78 | 12.93 |
| 9.57 | 9.24 | 12.57 |
| 10.95 | 8.08 | 13.52 |
| 12.73 | 6.95 | 30.67 |
| 14.11 | 6.28 | 42.82 |
| 14.62 | 6.06 | 100.00 |
| 15.58 | 5.69 | 16.35 |
| 17.14 | 5.17 | 38.31 |
| 18.26 | 4.86 | 2.40 |
| 18.74 | 4.74 | 23.10 |
| 20.96 | 4.24 | 14.57 |
| 21.66 | 4.10 | 6.82 |
| 22.02 | 4.04 | 7.60 |
| 25.70 | 3.46 | 18.95 |
| 26.91 | 3.31 | 6.91 |
| 29.53 | 3.03 | 14.41 |
| 30.92 | 2.89 | 3.19 |
| 32.72 | 2.74 | 6.04 |
| 34.57 | 2.59 | 4.03 |
| 36.46 | 2.46 | 4.48 |
| 37.18 | 2.42 | 6.04 |
| 38.31 | 2.35 | 5.73 |

EXAMPLE 5 PREPARATION OF FORM I OF SOTAGLIFLOZIN 8.0 mg of Sotagliflozin was added into a 1.5-mL glass vial followed by adding 0.075 mL of THF to form a clear solution. The clear solution was slowly added into 1.5 mL of water under magnetic stirring, and white solid precipitated immediately. The sample was stirred at room temperature for 24 hours, then filtered and dried to obtain a white solid.

Figure 30:
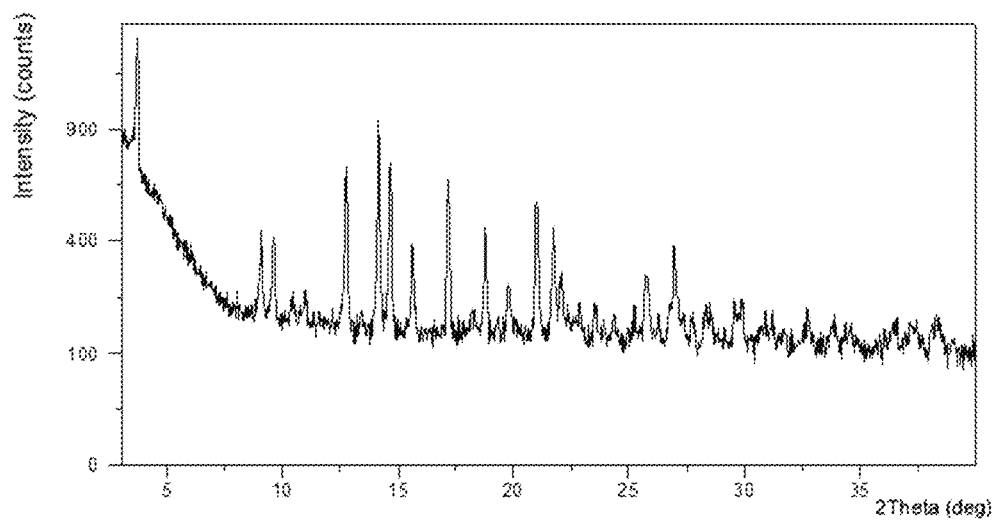
FIG. 30 shows an X-ray Powder Diffraction pattern of crystalline Form I in example 5.

The solid obtained in example 5 conformed to Form I. The XRPD data were listed in Table 5, and the XRPD pattern was substantially as depicted in FIG. 30.

TABLE 5

| 2theta (°) | d spacing | Intensity % |
|---|---|---|
| 3.66 | 24.16 | 100.00 |
| 9.04 | 9.78 | 24.71 |
| 9.58 | 9.24 | 24.22 |
| 10.41 | 8.50 | 5.08 |
| 10.95 | 8.08 | 6.91 |
| 12.73 | 6.96 | 59.25 |
| 14.11 | 6.28 | 81.65 |
| 14.62 | 6.06 | 63.19 |
| 15.58 | 5.69 | 25.79 |
| 17.13 | 5.18 | 50.02 |
| 18.75 | 4.73 | 31.86 |
| 19.74 | 4.50 | 13.54 |
| 20.95 | 4.24 | 44.43 |
| 21.70 | 4.10 | 3.39 |
| 22.04 | 4.03 | 17.63 |
| 23.50 | 3.79 | 6.17 |
| 25.65 | 3.47 | 16.01 |
| 26.92 | 3.31 | 27.49 |
| 27.71 | 3.22 | 5.51 |
| 28.36 | 3.15 | 6.31 |
| 29.50 | 3.03 | 10.12 |
| 29.85 | 2.99 | 10.54 |
| 32.69 | 2.74 | 6.26 |
| 33.84 | 2.65 | 5.00 |
| 36.52 | 2.46 | 4.75 |
| 37.25 | 2.41 | 5.16 |
| 38.24 | 2.35 | 5.55 |

EXAMPLE 6 PREPARATION OF FORM I OF SOTAGLIFLOZIN 10.4 mg of Sotagliflozin (the existing crystalline Form 2) was added into a 1.5-mL glass vial followed by adding 0.5 mL of H₂O to form a suspension. The suspension was stirred at room temperature for eight days, then filtered and dried to obtain a white solid.

Figure 31:
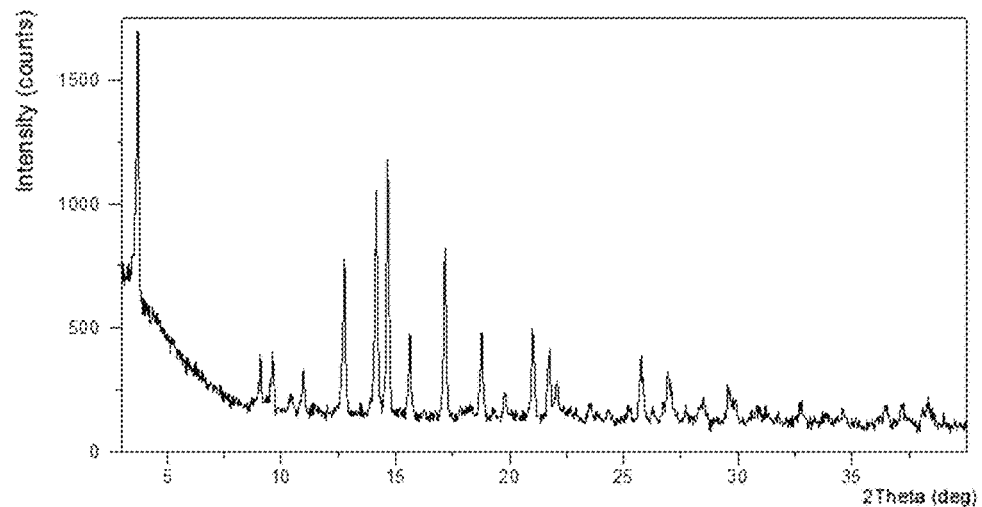
FIG. 31 shows an X-ray Powder Diffraction pattern of crystalline Form I in example 6.

The solid obtained in example 6 conformed to Form I. The XRPD data were listed in Table 6, and the XRPD pattern was substantially as depicted in FIG. 31.

TABLE 6

| 2theta (°) | d spacing | Intensity % |
|---|---|---|
| 3.66 | 24.16 | 100.00 |
| 9.04 | 9.78 | 17.51 |
| 9.58 | 9.23 | 17.83 |
| 10.39 | 8.51 | 4.94 |
| 10.93 | 8.10 | 14.52 |
| 12.73 | 6.95 | 50.78 |
| 14.10 | 6.28 | 74.17 |
| 14.61 | 6.06 | 81.09 |
| 15.59 | 5.69 | 26.51 |
| 17.13 | 5.18 | 54.75 |
| 18.73 | 4.74 | 28.86 |
| 19.74 | 4.50 | 7.45 |
| 20.97 | 4.24 | 29.78 |
| 21.69 | 4.10 | 20.67 |
| 22.03 | 4.04 | 10.90 |
| 23.50 | 3.79 | 4.90 |
| 25.70 | 3.47 | 21.77 |
| 26.87 | 3.32 | 16.11 |
| 28.46 | 3.14 | 7.14 |
| 29.50 | 3.03 | 10.43 |
| 30.76 | 2.91 | 4.27 |
| 32.73 | 2.74 | 6.95 |
| 34.52 | 2.60 | 3.69 |
| 36.46 | 2.46 | 6.10 |
| 37.16 | 2.42 | 7.14 |
| 38.21 | 2.36 | 6.20 |

EXAMPLE 7 PREPARATION OF FORM II OF SOTAGLIFLOZIN 39.5 mg of Sotagliflozin was added into a 20-mL glass vial followed by adding 0.8 mL of EtOAc to form a clear solution, and then 5.0 mL of n-heptane was slowly added under magnetic stirring. The sample was stirred for 24 hours, then filtered and dried to obtain a white solid.

Figure 5:
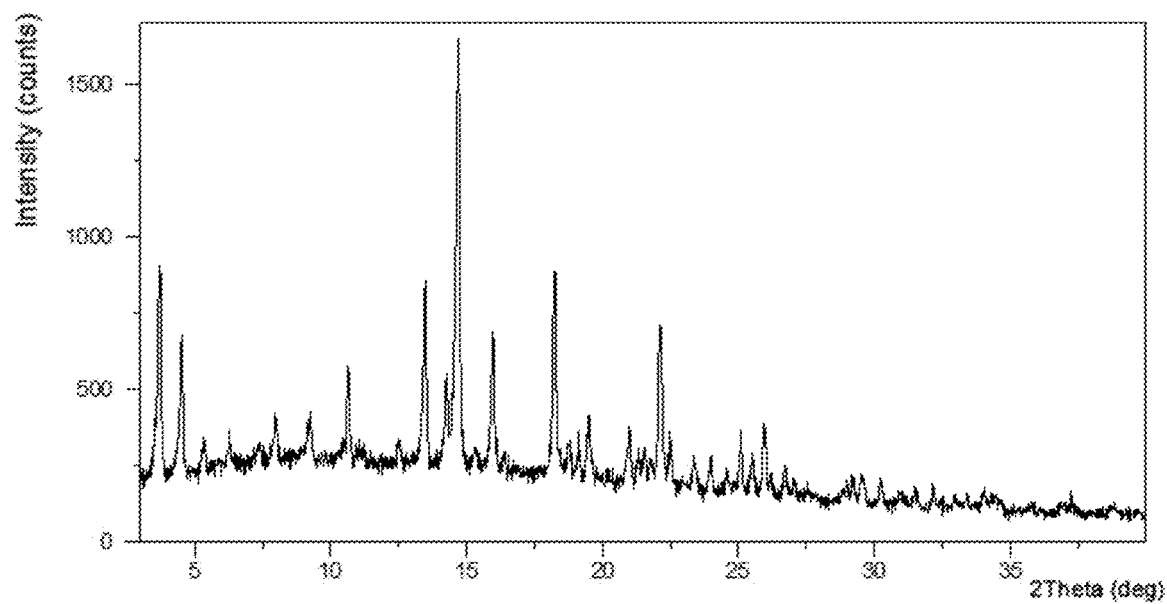
FIG. 5 shows an X-ray Powder Diffraction pattern of crystalline Form II in example 7.
Figure 6:
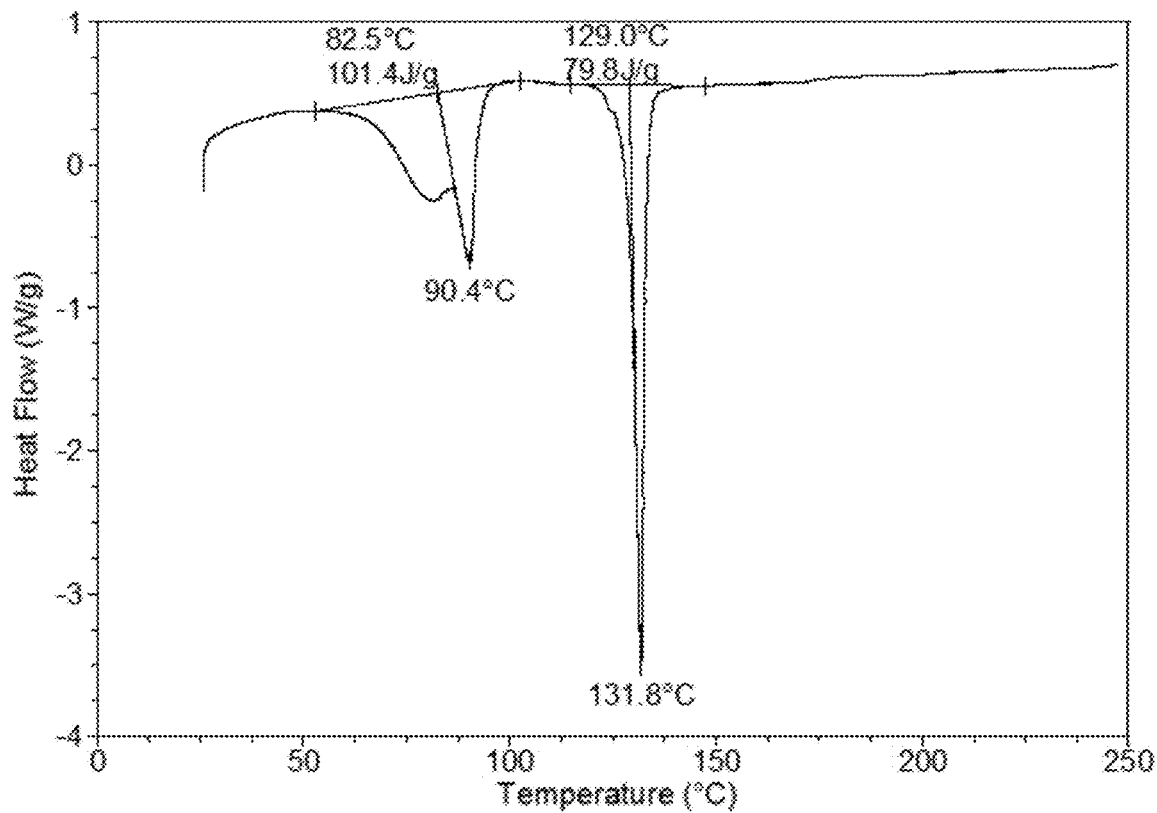
FIG. 6 shows a Differential Scanning calorimetry curve of crystalline Form II in example 7.
Figure 7:
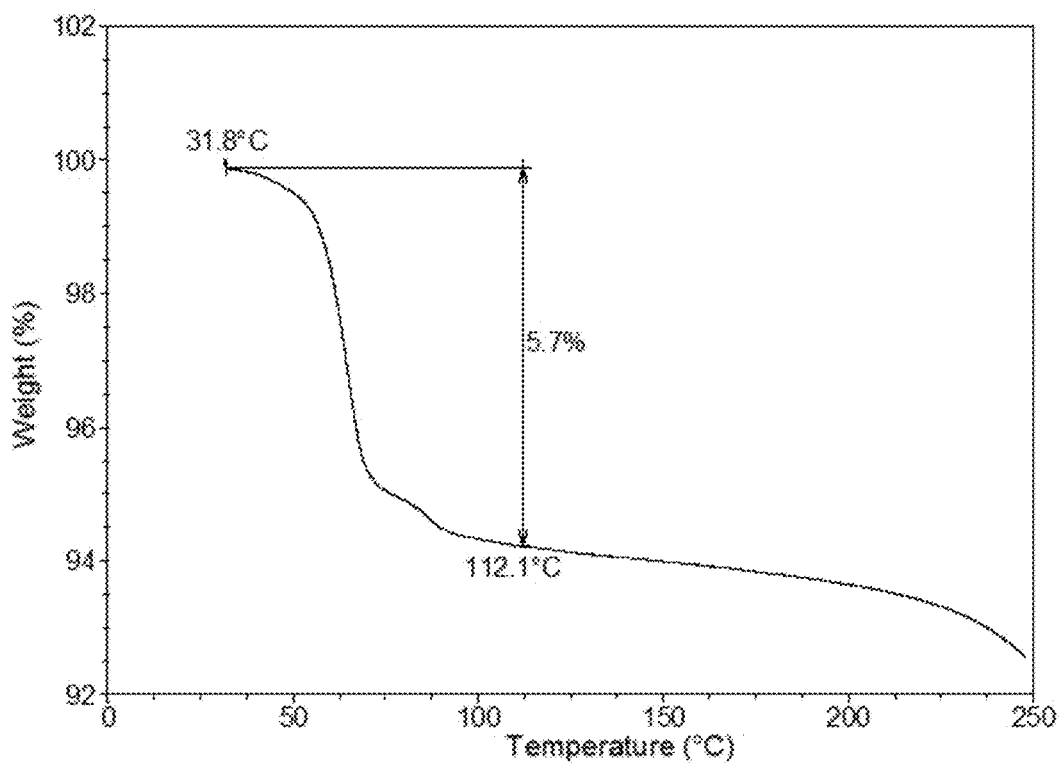
FIG. 7 shows a Thermal Gravimetric Analysis curve of crystalline Form II in example 7.
Figure 8:
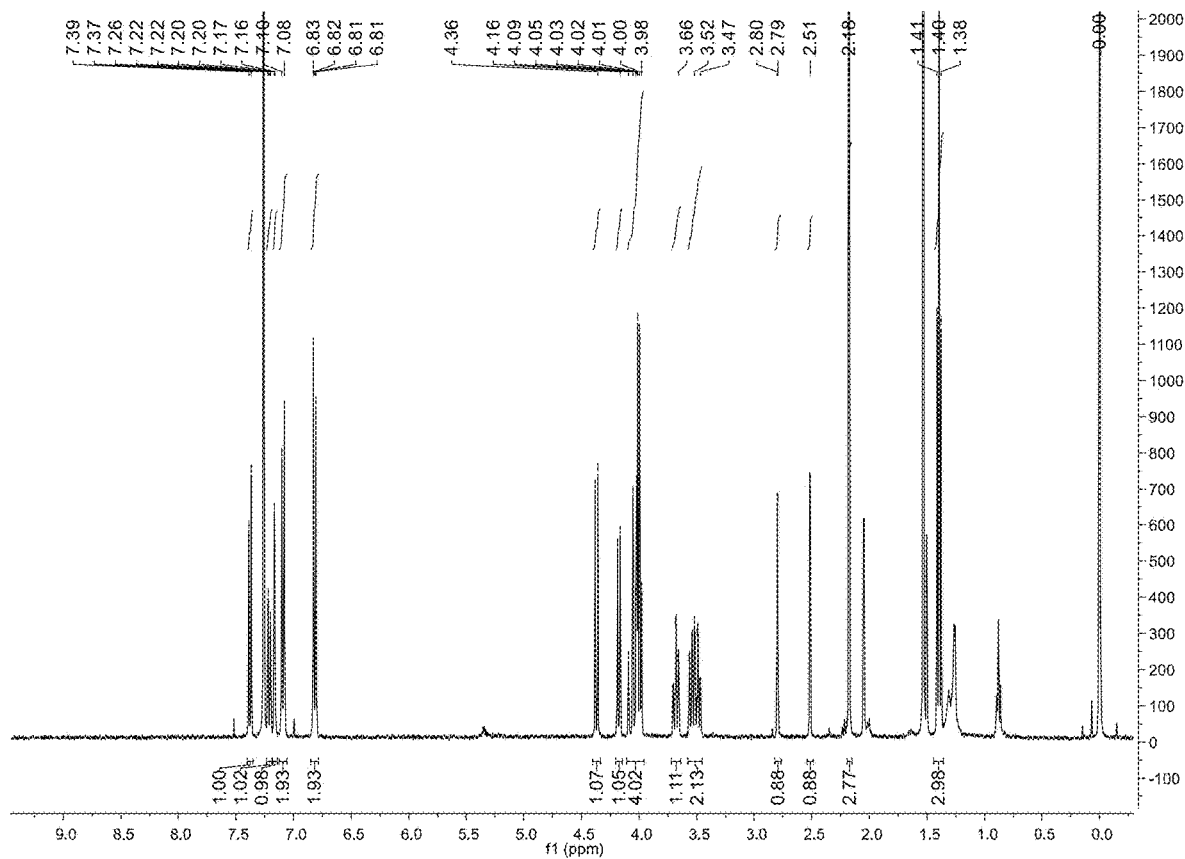
FIG. 8 shows a $^1$H NMR spectrum of crystalline Form II in example 7.

The solid obtained in example 7 conformed to Form II. The XRPD data were listed in Table 7, and the XRPD pattern was substantially as depicted in FIG. 5. The DSC curve was displayed in FIG. 6. The TGA curve was displayed in FIG. 7. The ¹H NMR spectrum was displayed in FIG. 8.

TABLE 7

| 2theta (°) | d spacing | Intensity % |
|---|---|---|
| 3.63 | 24.32 | 53.76 |
| 4.44 | 19.90 | 37.45 |
| 5.26 | 16.81 | 16.15 |
| 6.22 | 14.21 | 13.53 |
| 7.26 | 12.18 | 14.75 |
| 7.90 | 11.19 | 20.16 |
| 9.14 | 9.68 | 20.00 |
| 10.57 | 8.37 | 31.29 |
| 12.42 | 7.12 | 15.47 |
| 13.40 | 6.61 | 46.21 |
| 14.16 | 6.25 | 30.33 |
| 14.61 | 6.06 | 100.00 |
| 15.89 | 5.58 | 38.14 |
| 18.15 | 4.89 | 52.34 |
| 18.69 | 4.75 | 15.15 |
| 19.04 | 4.66 | 15.39 |
| 19.42 | 4.57 | 21.35 |
| 20.92 | 4.25 | 17.99 |
| 22.02 | 4.04 | 40.68 |
| 22.41 | 3.97 | 16.00 |
| 23.30 | 3.82 | 11.21 |
| 23.88 | 3.73 | 11.99 |
| 25.01 | 3.56 | 17.21 |
| 25.42 | 3.50 | 12.17 |
| 25.84 | 3.45 | 18.31 |
| 26.62 | 3.35 | 10.16 |
| 29.12 | 3.07 | 7.60 |
| 29.44 | 3.03 | 8.05 |
| 30.16 | 2.96 | 6.94 |
| 31.39 | 2.85 | 5.29 |
| 32.08 | 2.79 | 5.09 |
| 34.42 | 2.61 | 3.17 |
| 37.03 | 2.43 | 1.76 |

EXAMPLE 8 PREPARATION OF FORM II OF SOTAGLIFLOZIN 8.5 mg of Sotagliflozin was added into a 1.5-mL glass vial followed by adding 0.3 mL of ACN to form a clear solution. White precipitation appeared after 1.5 mL of H₂O being slowly added under magnetic stirring. The sample was stirred at room temperature for 24 hours, then filtered and dried to obtain a white solid.

Figure 32:
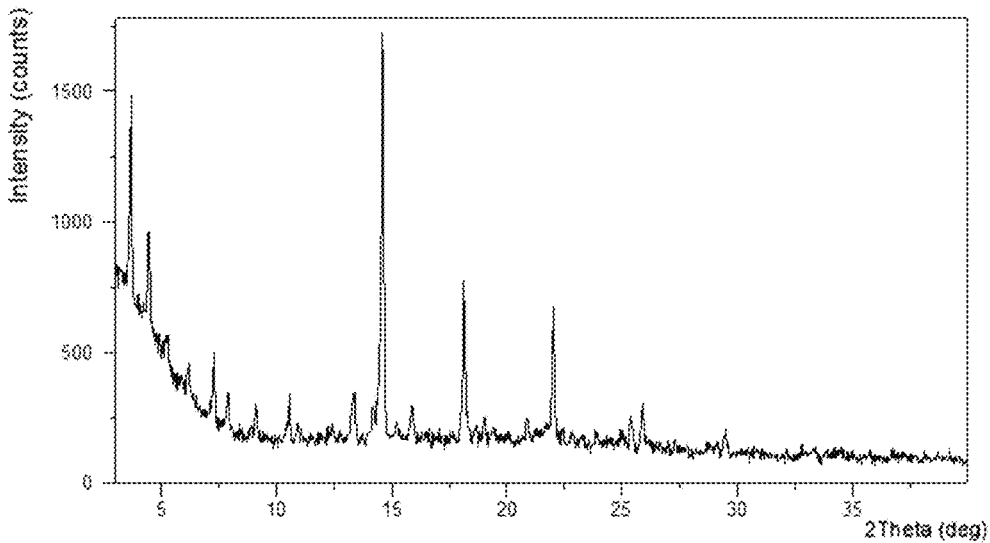
FIG. 32 shows an X-ray Powder Diffraction pattern of crystalline Form II in example 8.

The solid obtained in example 8 conformed to Form II. The XRPD data were listed in Table 8, and the XRPD pattern was substantially as depicted in FIG. 32.

TABLE 8

| 2theta (°) | d spacing | Intensity % |
|---|---|---|
| 3.67 | 24.05 | 79.75 |
| 4.47 | 19.78 | 51.83 |
| 5.29 | 16.71 | 27.66 |
| 6.19 | 14.29 | 18.29 |
| 7.30 | 12.11 | 23.28 |
| 7.92 | 11.17 | 13.55 |
| 9.13 | 9.69 | 10.12 |
| 10.58 | 8.36 | 13.10 |
| 13.37 | 6.62 | 13.13 |
| 14.17 | 6.25 | 10.22 |
| 14.61 | 6.06 | 100.00 |
| 15.89 | 5.58 | 9.98 |
| 18.13 | 4.89 | 39.54 |
| 19.05 | 4.66 | 7.84 |
| 20.91 | 4.25 | 6.52 |
| 22.03 | 4.03 | 34.58 |
| 23.91 | 3.72 | 4.26 |
| 24.99 | 3.56 | 3.97 |
| 25.40 | 3.51 | 7.21 |
| 25.88 | 3.44 | 10.78 |
| 29.48 | 3.03 | 5.47 |

EXAMPLE 9 PREPARATION OF FORM II OF SOTAGLIFLOZIN 8.4 mg of Sotagliflozin was added into a 1.5-mL glass vial followed by adding 0.075 mL of THF to form a clear solution. White precipitation appeared after 1.5 mL of n-heptane being slowly added under magnetic stirring. The sample was stirred at room temperature for 24 hours, then filtered and dried to obtain a white solid.

Figure 33:
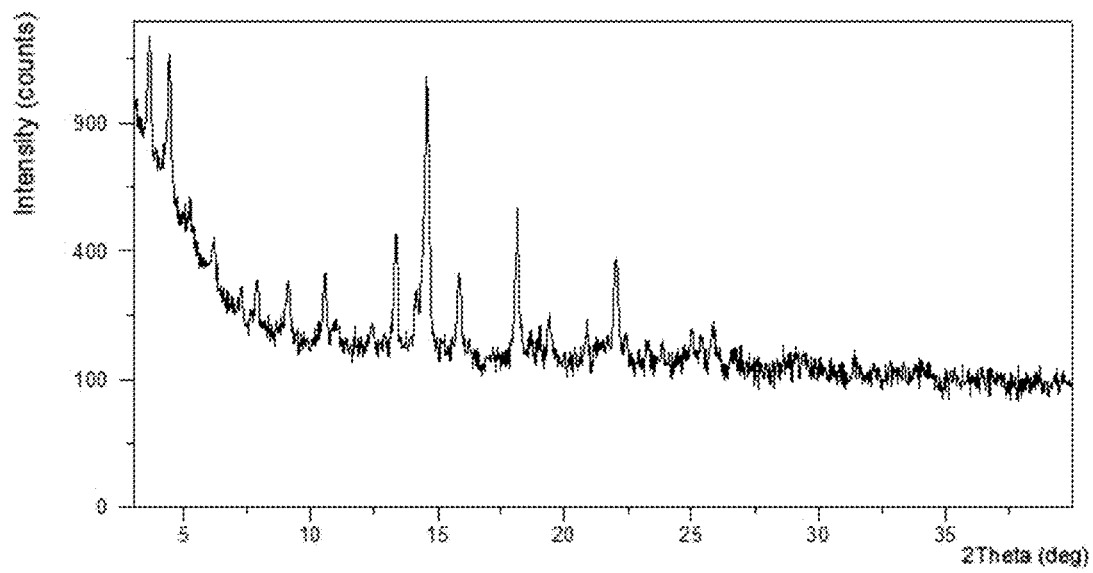
FIG. 33 shows an X-ray Powder Diffraction pattern of crystalline Form II in example 9.

The solid obtained in example 9 conformed to be Form II. The XRPD data were listed in Table 9, and the XRPD pattern was substantially as depicted in FIG. 33.

TABLE 9

| 2theta (°) | d spacing | Intensity % |
|---|---|---|
| 3.65 | 24.21 | 100.00 |
| 4.44 | 19.88 | 91.39 |
| 5.28 | 16.73 | 36.18 |
| 6.20 | 14.26 | 24.64 |
| 7.27 | 12.16 | 13.40 |
| 7.91 | 11.18 | 15.39 |
| 9.11 | 9.71 | 13.78 |
| 10.56 | 8.38 | 17.31 |
| 12.42 | 7.12 | 6.32 |
| 13.38 | 6.62 | 25.51 |
| 14.60 | 6.07 | 78.78 |
| 15.87 | 5.58 | 16.26 |
| 18.15 | 4.89 | 32.76 |
| 19.39 | 4.58 | 6.67 |
| 20.89 | 4.25 | 5.87 |
| 22.03 | 4.04 | 20.43 |
| 25.84 | 3.45 | 5.58 |
| 29.16 | 3.06 | 1.83 |
| 34.17 | 2.62 | 1.61 |

EXAMPLE 10 PREPARATION OF FORM II OF SOTAGLIFLOZIN 8.4 mg of Sotagliflozin was added into a 1.5-mL glass vial followed by adding 0.075 mL of acetone to form a clear solution, and then 1.5 mL of Toluene was slowly added under magnetic stirring. The sample was stirred for 24 hours, then filtered and dried to obtain a white solid.

Figure 34:
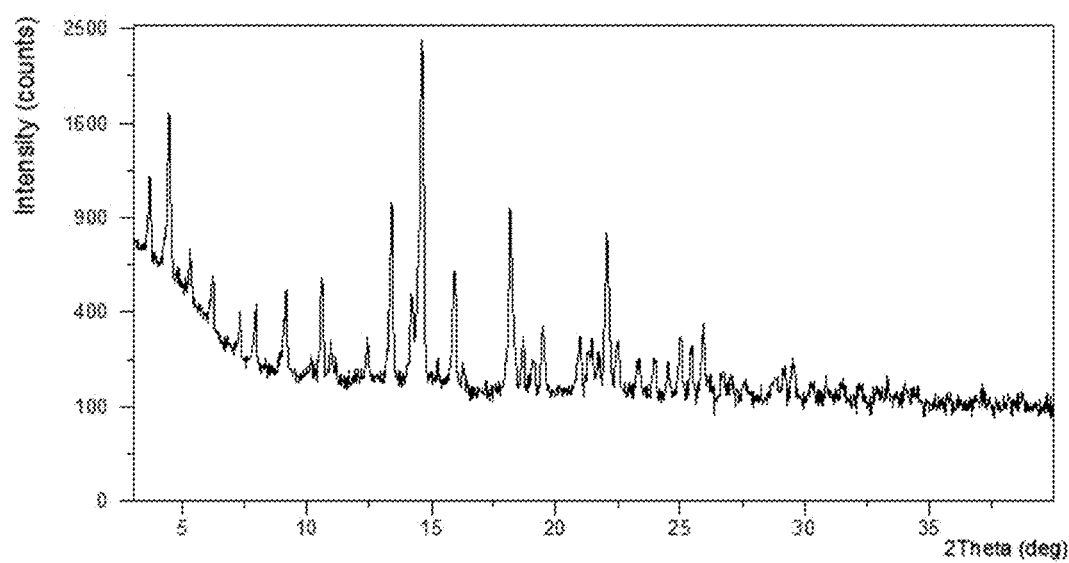
FIG. 34 shows an X-ray Powder Diffraction pattern of crystalline Form II in example 10.

The solid obtained in example 10 conformed to be Form II. The XRPD data were listed in Table 10, and the XRPD pattern was substantially as depicted in FIG. 34

TABLE 10

| 2theta (°) | d spacing | Intensity % |
|---|---|---|
| 3.65 | 24.20 | 47.15 |
| 4.43 | 19.93 | 71.37 |
| 5.28 | 16.74 | 26.67 |
| 6.18 | 14.30 | 20.56 |
| 7.28 | 12.14 | 12.33 |
| 7.91 | 11.17 | 14.46 |
| 9.13 | 9.68 | 17.08 |
| 10.58 | 8.36 | 20.02 |
| 10.93 | 8.09 | 8.25 |
| 12.40 | 7.14 | 8.83 |
| 13.39 | 6.62 | 40.04 |
| 14.19 | 6.24 | 15.74 |
| 14.60 | 6.07 | 100.00 |
| 15.90 | 5.57 | 22.02 |
| 18.15 | 4.89 | 38.85 |
| 18.64 | 4.76 | 7.78 |
| 19.46 | 4.56 | 9.65 |
| 20.95 | 4.24 | 8.48 |
| 21.38 | 4.16 | 6.51 |
| 22.03 | 4.03 | 29.40 |

TABLE 10-continued

| 2theta (°) | d spacing | Intensity % |
|---|---|---|
| 22.45 | 3.96 | 8.03 |
| 23.31 | 3.82 | 4.95 |
| 23.95 | 3.72 | 4.57 |
| 24.48 | 3.64 | 4.12 |
| 24.99 | 3.56 | 8.52 |
| 25.44 | 3.50 | 7.14 |
| 25.90 | 3.44 | 10.55 |
| 26.67 | 3.34 | 3.35 |
| 29.51 | 3.03 | 4.74 |

EXAMPLE 11 PREPARATION OF FORM II OF SOTAGLIFLOZIN 8.3 mg of Sotagliflozin (the existing anhydrous crystalline Form 2) was added into a 1.5-mL glass vial followed by adding 0.35 mL of ACN/H$_2$O (1:6, v/v). The sample was stirred at 70° C. for fourteen days, then filtered and dried to obtain a white solid.

Figure 35:
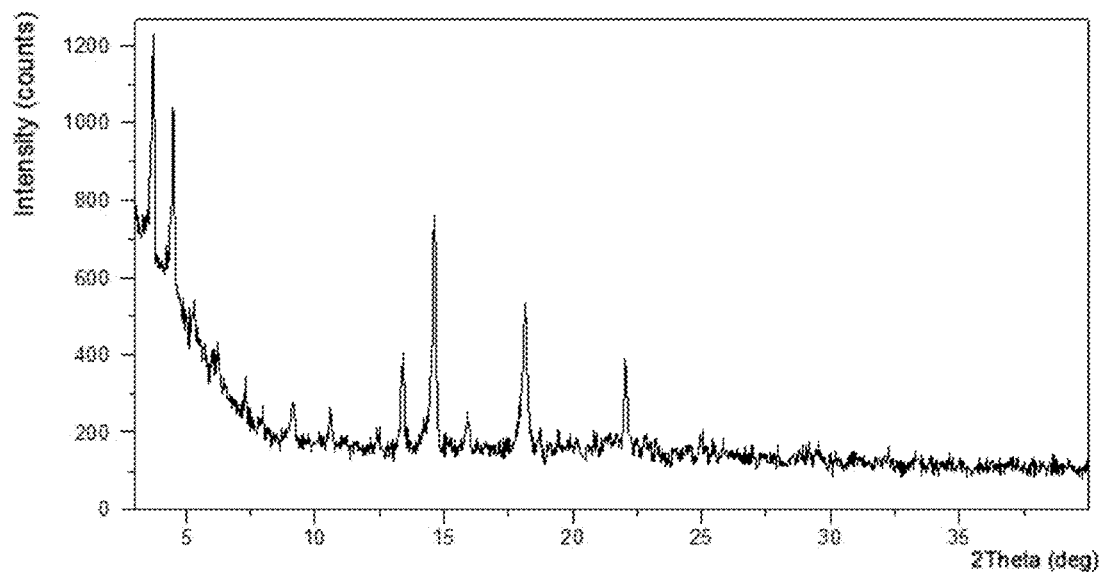
FIG. 35 shows an X-ray Powder Diffraction pattern of crystalline Form II in example 11.

The solid obtained in example 11 conformed to be Form II. The XRPD data were listed in Table 11, and the XRPD pattern was substantially as depicted in FIG. 35.

TABLE 11

| 2theta (°) | d spacing | Intensity % |
|---|---|---|
| 3.68 | 24.02 | 100.00 |
| 4.46 | 19.80 | 82.61 |
| 5.24 | 16.88 | 33.85 |
| 6.19 | 14.27 | 23.59 |
| 7.27 | 12.17 | 17.29 |
| 7.88 | 11.22 | 7.76 |
| 9.12 | 9.70 | 11.04 |
| 10.55 | 8.38 | 9.69 |
| 12.40 | 7.14 | 3.47 |
| 13.37 | 6.62 | 21.63 |
| 14.60 | 6.07 | 56.69 |
| 15.90 | 5.57 | 7.91 |
| 18.13 | 4.89 | 32.85 |
| 18.68 | 4.75 | 4.53 |
| 22.03 | 4.04 | 21.64 |
| 22.77 | 3.91 | 3.56 |
| 24.96 | 3.57 | 3.79 |
| 29.47 | 3.03 | 3.47 |
| 33.30 | 2.69 | 1.56 |
| 33.89 | 2.65 | 1.99 |

EXAMPLE 12 PREPARATION OF FORM II OF SOTAGLIFLOZIN 8.3 mg of Sotagliflozin (the existing crystalline Form 2) was added into a 1.5-mL glass vial followed by adding 0.35 mL of acetone/H$_2$O (1:6, v/v), and then the glass vial was capped. The sample was stirred at 70° C. for fourteen days, then filtered and dried to obtain a white solid.

Figure 36:
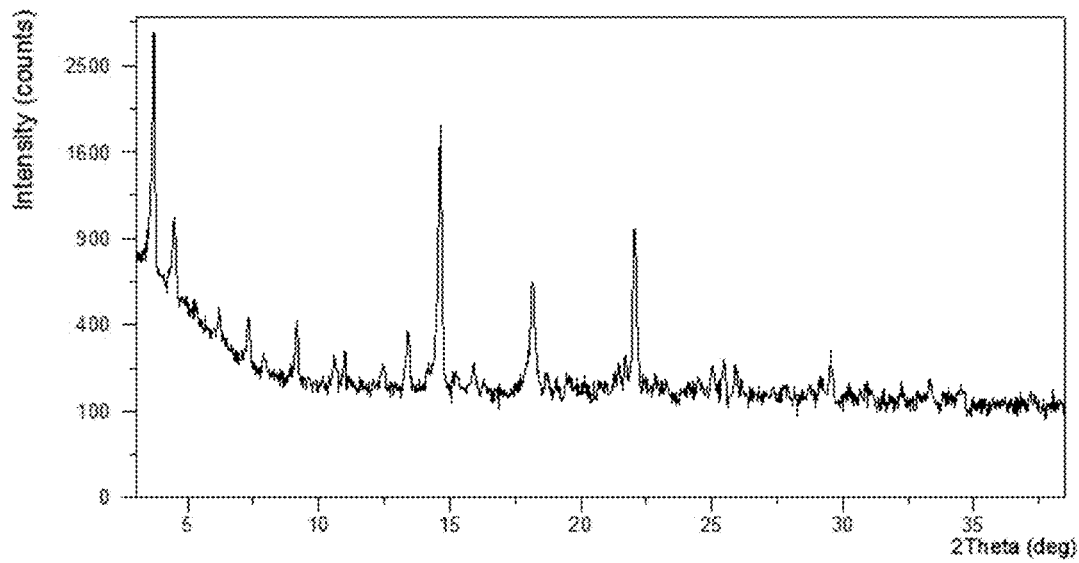
FIG. 36 shows an X-ray Powder Diffraction pattern of crystalline Form II in example 12.

The solid obtained in example 12 conformed to Form II. The XRPD data were listed in Table 12, and the XRPD pattern was substantially as depicted in FIG. 36.

TABLE 12

| 2theta (°) | d spacing | Intensity % |
|---|---|---|
| 3.67 | 24.07 | 100.00 |
| 4.45 | 19.87 | 33.61 |
| 6.16 | 14.35 | 11.16 |
| 7.27 | 12.15 | 10.97 |
| 9.12 | 9.70 | 9.69 |
| 10.57 | 8.37 | 4.22 |
| 10.96 | 8.07 | 5.43 |
| 12.44 | 7.11 | 3.09 |
| 13.38 | 6.62 | 8.40 |
| 14.61 | 6.06 | 59.97 |
| 15.19 | 5.83 | 2.45 |
| 15.89 | 5.58 | 3.27 |
| 18.13 | 4.89 | 16.88 |
| 18.67 | 4.75 | 2.45 |
| 19.46 | 4.56 | 1.69 |
| 21.68 | 4.10 | 4.95 |
| 22.02 | 4.04 | 30.32 |
| 25.00 | 3.56 | 3.33 |
| 25.42 | 3.50 | 3.67 |
| 25.86 | 3.45 | 2.82 |
| 29.50 | 3.03 | 5.79 |
| 30.95 | 2.89 | 1.11 |
| 32.22 | 2.78 | 1.35 |
| 33.31 | 2.69 | 2.29 |
| 34.55 | 2.60 | 1.23 |

EXAMPLE 13 PREPARATION OF FORM III OF SOTAGLIFLOZIN 39.2 mg of Sotagliflozin was added into a 3-mL glass vial followed by adding 1.0 mL of CHCl$_3$ to form a clear solution. The white solid was obtained after slow evaporation at room temperature.

Figure 9:
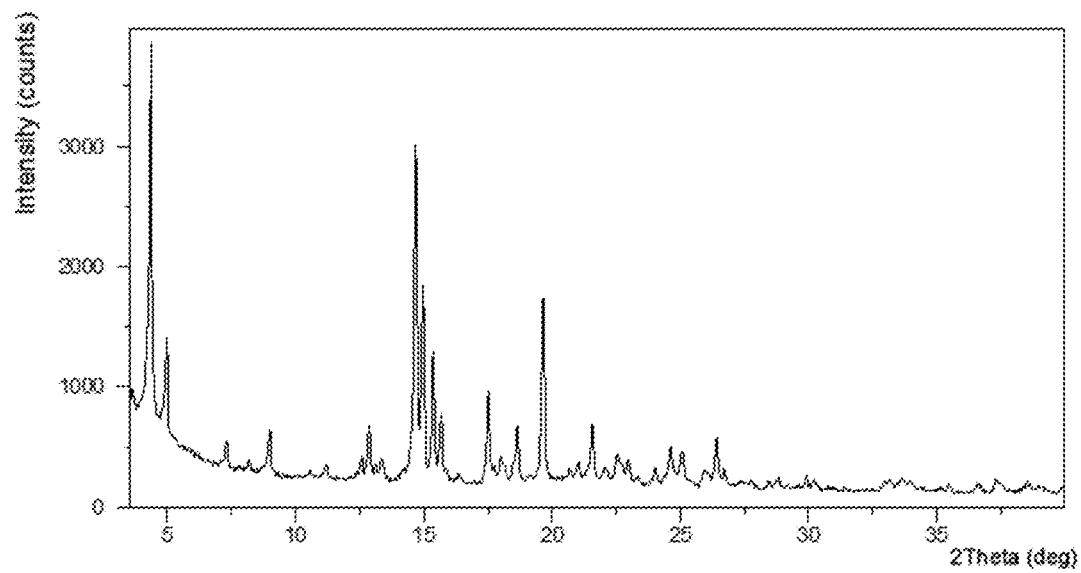
FIG. 9 shows an X-ray Powder Diffraction pattern of crystalline Form III in example 13.
Figure 10:
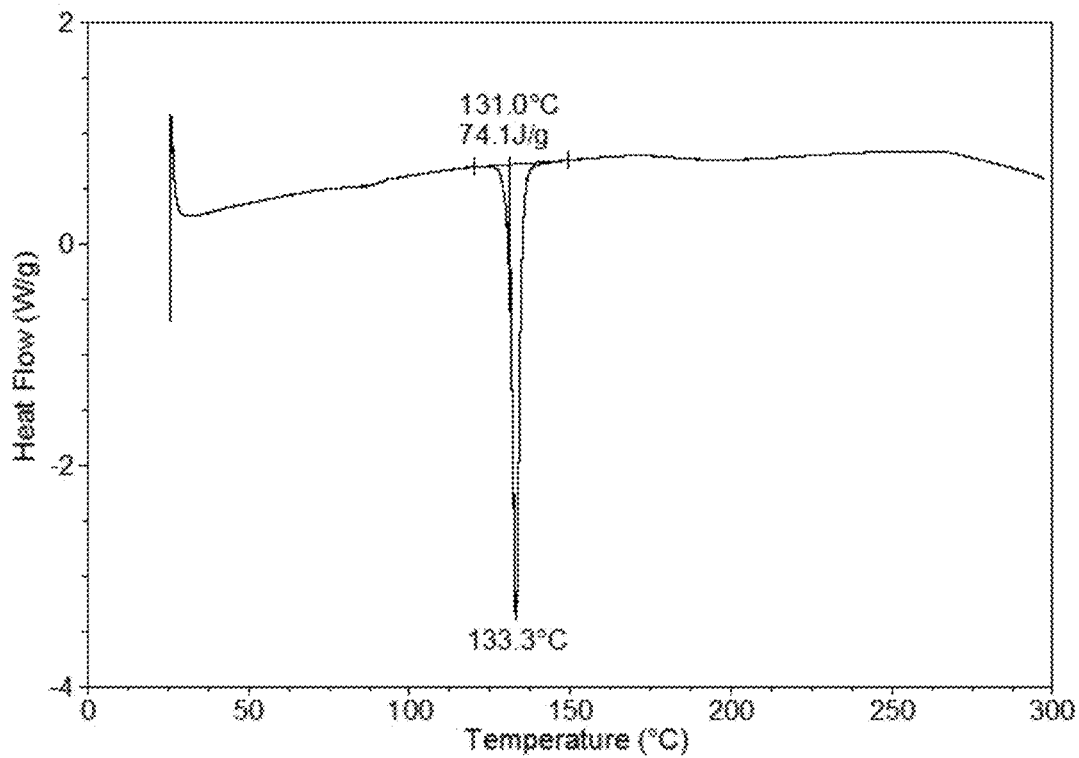
FIG. 10 shows a Differential Scanning calorimetry curve of crystalline Form III in example 13.
Figure 11:
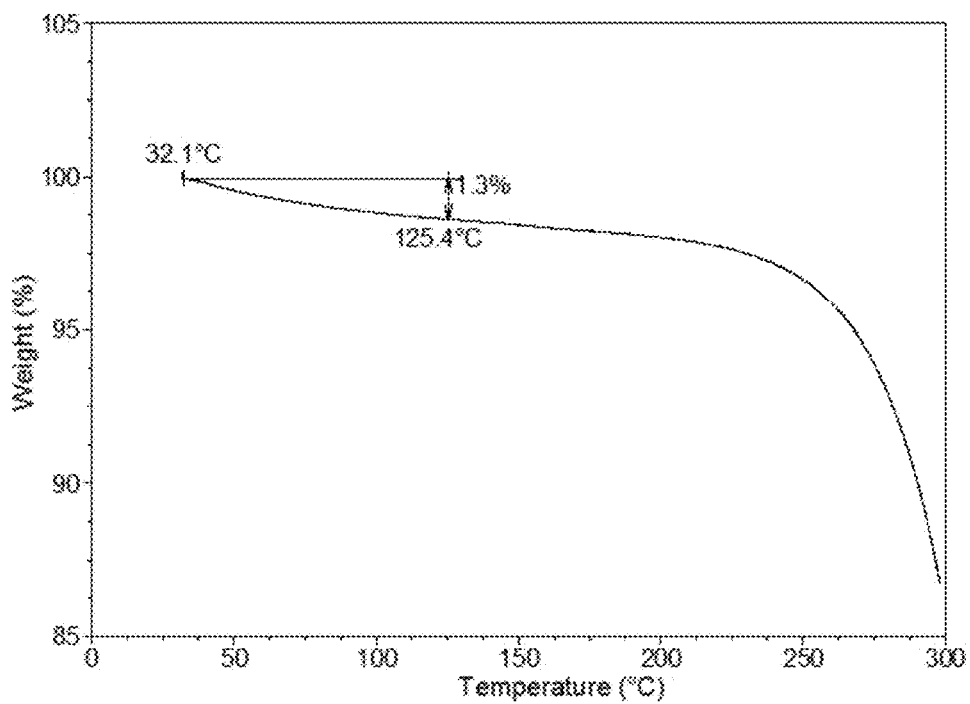
FIG. 11 shows a Thermal Gravimetric Analysis curve of crystalline Form III in example 13.
Figure 12:
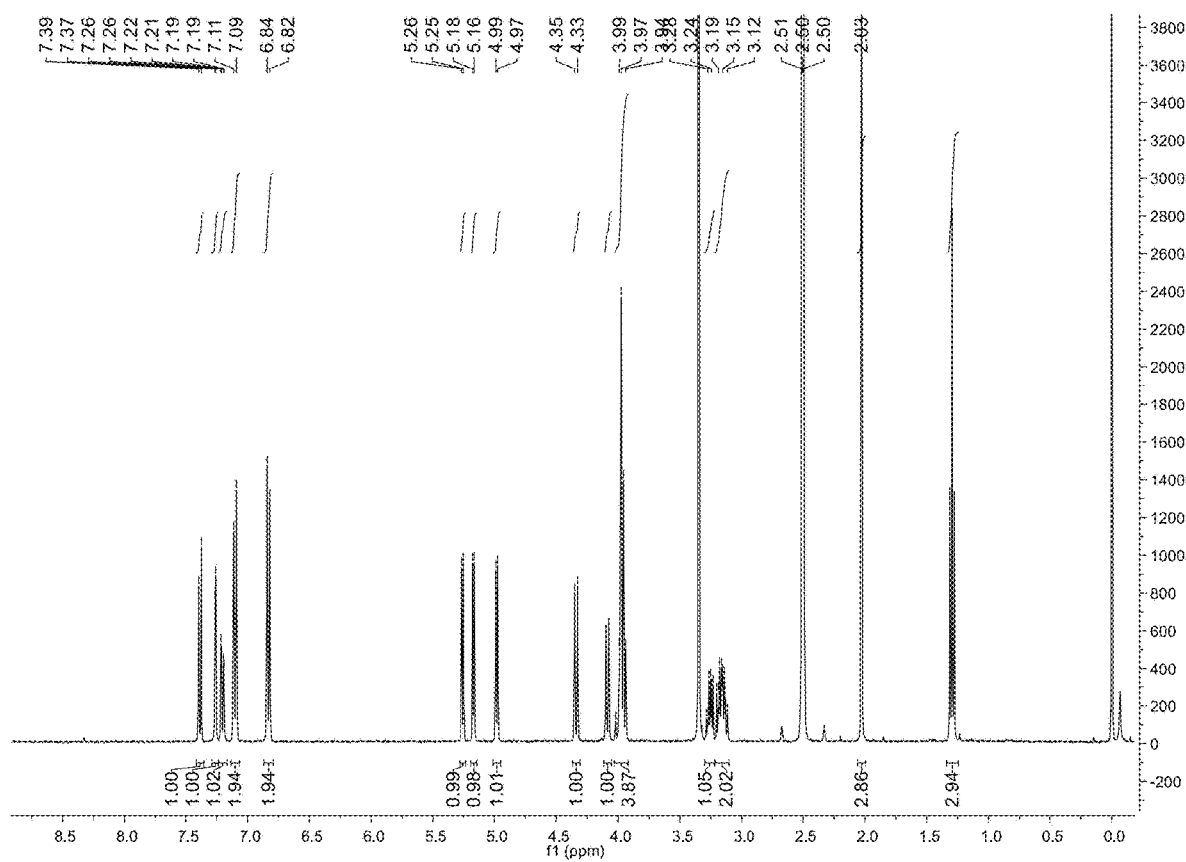
FIG. 12 shows a $^1$H NMR spectrum of crystalline Form III in example 13.

The solid obtained in example 13 conformed to Form III. The XRPD data were listed in Table 13, and the XRPD pattern was substantially as depicted in FIG. 9. The DSC curve was displayed in FIG. 10. The TGA curve was displayed in FIG. 11. The $^1$H NMR spectrum was displayed in FIG. 12.

TABLE 13

| 2theta (°) | d spacing | Intensity % |
|---|---|---|
| 3.62 | 24.42 | 23.29 |
| 4.33 | 20.39 | 100.00 |
| 4.95 | 17.87 | 32.99 |
| 7.29 | 12.12 | 11.62 |
| 8.15 | 10.85 | 6.78 |
| 8.96 | 9.87 | 13.75 |
| 11.17 | 7.92 | 6.23 |
| 12.53 | 7.06 | 8.09 |
| 12.84 | 6.89 | 14.94 |
| 13.31 | 6.65 | 7.65 |
| 14.65 | 6.05 | 75.97 |
| 14.93 | 5.93 | 44.75 |
| 15.32 | 5.78 | 30.60 |
| 15.64 | 5.67 | 17.28 |
| 16.35 | 5.42 | 4.06 |
| 17.47 | 5.08 | 22.73 |
| 17.96 | 4.94 | 7.73 |
| 18.61 | 4.77 | 15.04 |
| 19.60 | 4.53 | 42.47 |
| 20.97 | 4.24 | 6.70 |
| 21.53 | 4.13 | 15.24 |
| 22.01 | 4.04 | 5.30 |
| 22.48 | 3.95 | 8.56 |
| 22.93 | 3.88 | 7.08 |
| 23.97 | 3.71 | 5.64 |
| 24.57 | 3.62 | 10.61 |
| 25.01 | 3.56 | 9.38 |
| 25.89 | 3.44 | 4.87 |
| 26.35 | 3.38 | 11.83 |
| 26.65 | 3.34 | 5.17 |
| 28.38 | 3.15 | 2.37 |
| 28.74 | 3.11 | 3.28 |

TABLE 13-continued

| 2theta (°) | d spacing | Intensity % |
|---|---|---|
| 29.86 | 2.99 | 3.45 |
| 33.67 | 2.66 | 2.12 |
| 35.41 | 2.53 | 1.46 |
| 36.53 | 2.46 | 1.94 |
| 37.25 | 2.41 | 2.75 |
| 38.46 | 2.34 | 2.17 |
| 40.01 | 2.25 | 2.38 |

EXAMPLE 14 PREPARATION OF FORM III OF SOTAGLIFLOZIN 5.4 mg of Sotagliflozin was added into a 1.5-mL glass vial followed by adding 0.5 mL of $CHCl_3$/n-heptane (4:1, v/v) to form a clear solution. The white solid was obtained after slow evaporation at room temperature.

Figure 37:
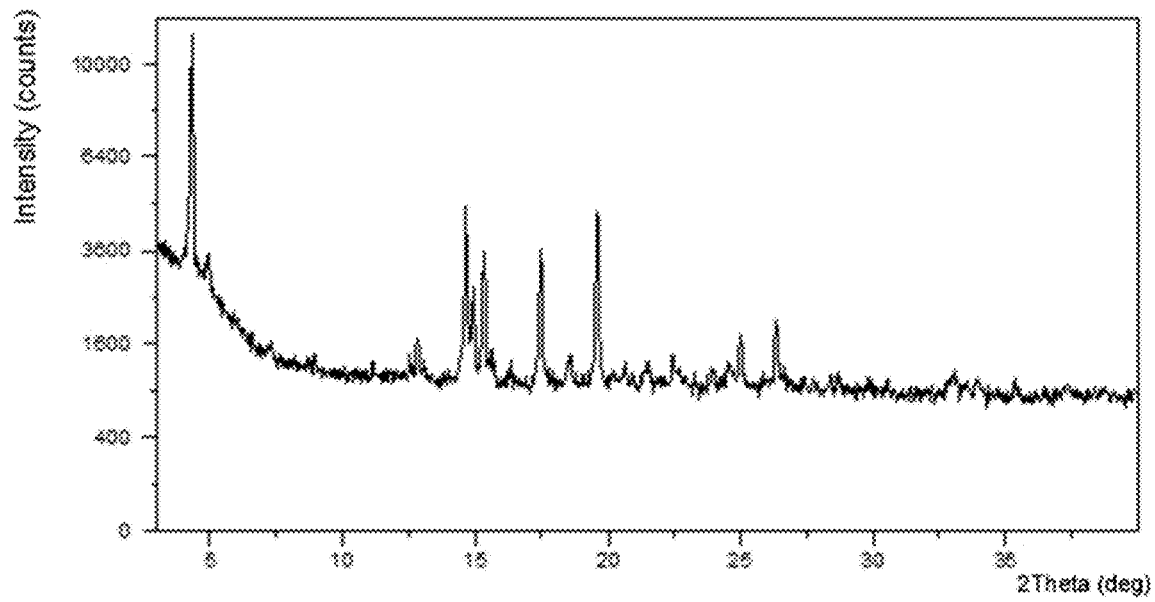
FIG. 37 shows an X-ray Powder Diffraction pattern of crystalline Form III in example 14.

The solid obtained in example 14 conformed to Form III. The XRPD data were listed in Table 14, and the XRPD pattern was substantially as depicted in FIG. 37.

TABLE 14

| 2theta (°) | d spacing | Intensity % |
|---|---|---|
| 4.33 | 20.40 | 100.00 |
| 4.95 | 17.86 | 12.22 |
| 12.83 | 6.90 | 7.66 |
| 14.65 | 6.05 | 47.35 |
| 14.93 | 5.94 | 19.25 |
| 15.33 | 5.78 | 31.70 |
| 16.35 | 5.42 | 2.64 |
| 17.47 | 5.08 | 32.43 |
| 18.61 | 4.77 | 5.76 |
| 19.61 | 4.53 | 46.30 |
| 20.71 | 4.29 | 1.99 |
| 21.51 | 4.13 | 3.87 |
| 22.45 | 3.96 | 5.19 |
| 24.00 | 3.71 | 3.10 |
| 25.02 | 3.56 | 9.91 |
| 26.36 | 3.38 | 14.22 |
| 28.38 | 3.14 | 2.38 |
| 33.11 | 2.71 | 2.85 |
| 33.94 | 2.64 | 2.53 |
| 35.38 | 2.54 | 2.11 |
| 37.32 | 2.41 | 1.75 |

EXAMPLE 15 PREPARATION OF FORM V OF SOTAGLIFLOZIN 44.3 mg of Sotagliflozin was added into a 5-mL glass vial followed by adding 4 mL of $MeOH/H_2O$ (1:1, v/v) to form a clear solution at 50° C. The clear solution was stirred at 5° C. for three days to obtain a white solid.

Figure 13:
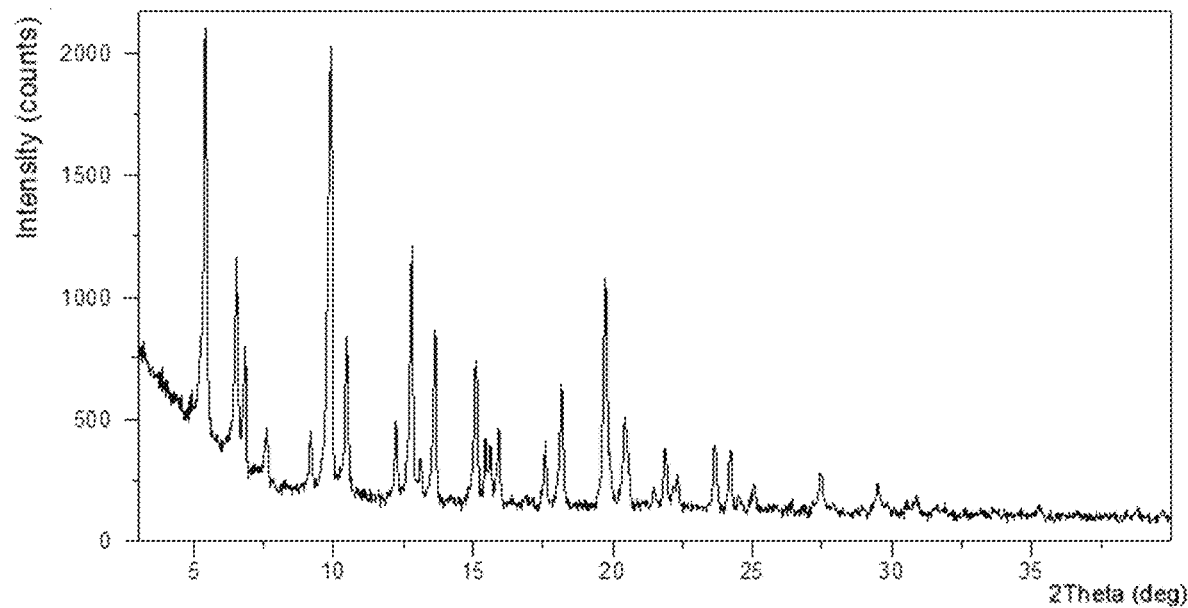
FIG. 13 shows an X-ray Powder Diffraction pattern of crystalline Form V in example 15.
Figure 14:
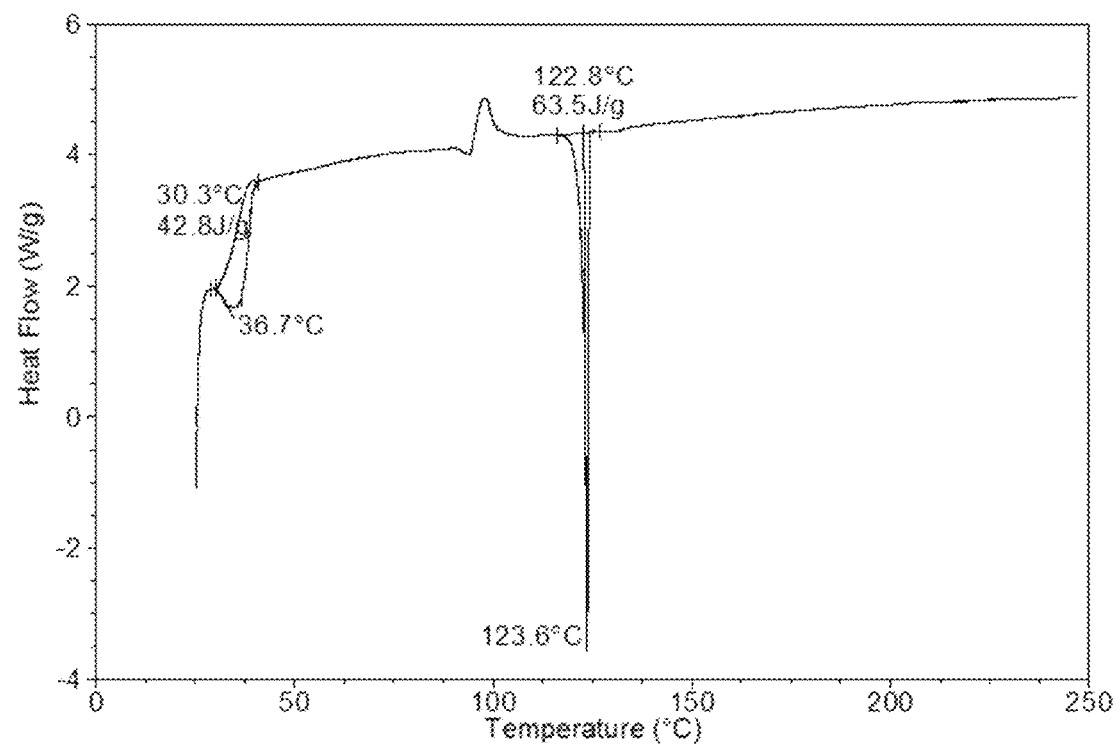
FIG. 14 shows a Differential Scanning calorimetry curve of crystalline Form V in example 15.
Figure 15:
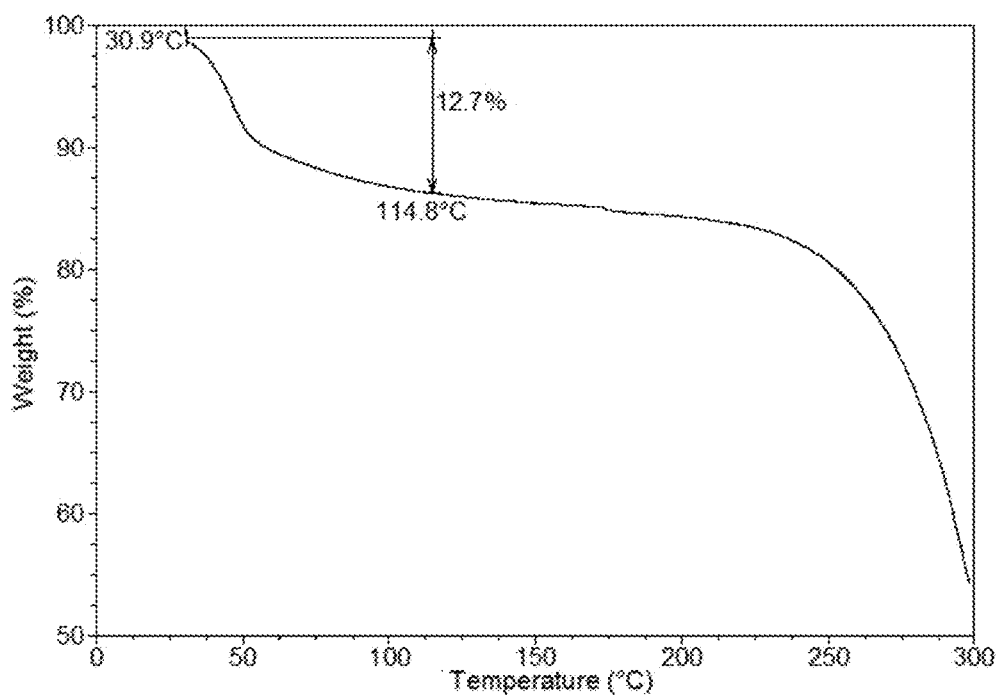
FIG. 15 shows a Thermal Gravimetric Analysis curve of crystalline Form Vin example 15.
Figure 16:
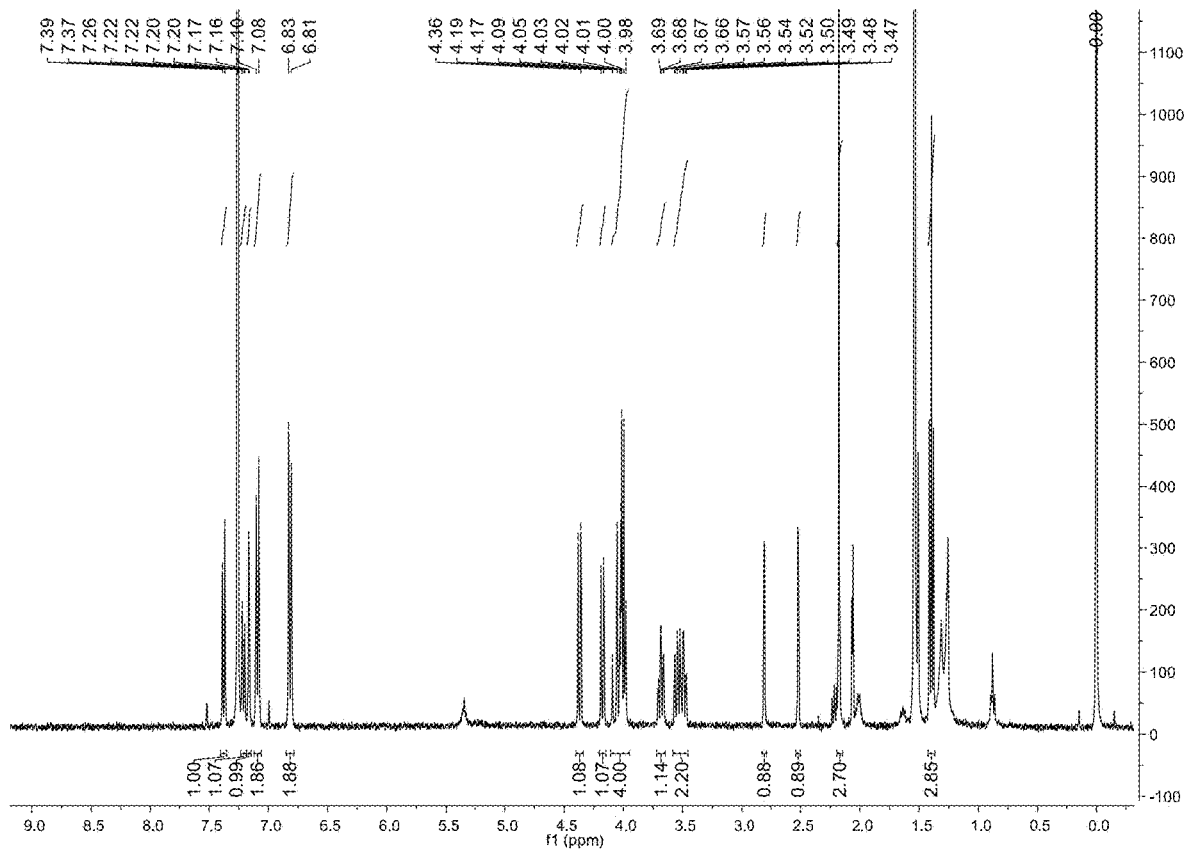
FIG. 16 shows a $^1$H NMR spectrum of crystalline Form V in example 15.

The solid obtained in example 15 conformed to Form V. The XRPD data were listed in Table 15, and the XRPD pattern was substantially as depicted in FIG. 13. The DSC curve was displayed in FIG. 14. The TGA curve was displayed in FIG. 15. The $^1$H NMR spectrum was displayed in FIG. 16.

TABLE 15

| 2theta (°) | d spacing | Intensity % |
|---|---|---|
| 5.42 | 16.30 | 100.00 |
| 6.54 | 13.52 | 28.05 |
| 6.83 | 12.95 | 11.09 |
| 7.60 | 11.63 | 4.48 |
| 8.12 | 10.89 | 3.11 |
| 9.19 | 9.62 | 7.06 |
| 9.90 | 8.93 | 76.05 |
| 10.48 | 8.44 | 17.21 |
| 12.24 | 7.23 | 7.96 |
| 12.80 | 6.92 | 35.18 |
| 13.11 | 6.75 | 6.18 |
| 13.63 | 6.50 | 17.96 |
| 15.12 | 5.86 | 27.13 |
| 15.47 | 5.73 | 7.98 |
| 15.64 | 5.67 | 6.59 |
| 15.93 | 5.56 | 14.04 |
| 17.60 | 5.04 | 8.76 |
| 18.18 | 4.88 | 13.48 |
| 19.74 | 4.50 | 38.20 |
| 20.42 | 4.35 | 11.13 |
| 21.88 | 4.06 | 9.62 |
| 22.30 | 3.99 | 3.88 |
| 23.65 | 3.76 | 9.75 |
| 24.19 | 3.68 | 7.87 |
| 25.07 | 3.55 | 4.58 |
| 27.47 | 3.25 | 6.05 |
| 29.45 | 3.03 | 5.02 |
| 30.78 | 2.91 | 0.93 |
| 31.69 | 2.82 | 1.11 |

EXAMPLE 16 PREPARATION OF FORM V OF SOTAGLIFLOZIN 101.8 mg of Sotagliflozin was added into a 20-mL glass vial followed by adding 10 mL of $MeOH/H_2O$ (2:3, v/v) to form a clear solution at 50° C. The clear solution was stirred at 5° C. for 24 hours to obtain a white solid.

Figure 38:
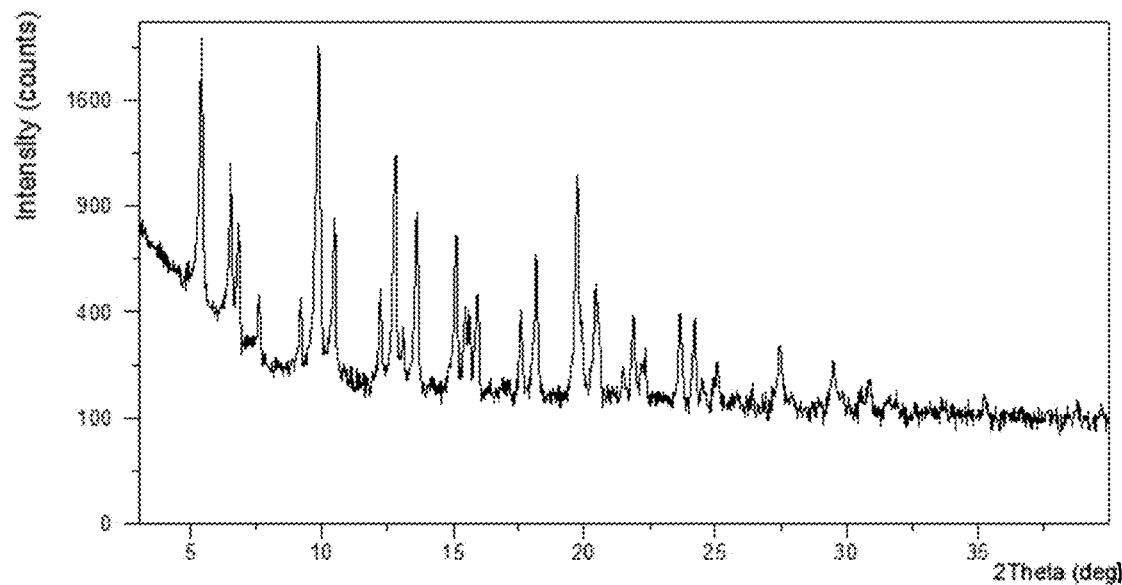
FIG. 38 shows an X-ray Powder Diffraction pattern of crystalline Form V in example 16.

The solid obtained in example 16 conformed to Form V. The XRPD data were listed in Table 16, and the XRPD pattern was substantially as depicted in FIG. 38.

TABLE 16

| 2theta (°) | d spacing | Intensity % |
|---|---|---|
| 5.42 | 16.30 | 93.32 |
| 6.53 | 13.54 | 41.77 |
| 6.83 | 12.95 | 23.87 |
| 7.61 | 11.62 | 10.71 |
| 9.18 | 9.63 | 12.99 |
| 9.90 | 8.93 | 100.00 |
| 10.48 | 8.44 | 35.35 |
| 12.25 | 7.23 | 16.13 |
| 12.80 | 6.92 | 57.47 |
| 13.12 | 6.75 | 9.19 |
| 13.62 | 6.50 | 39.72 |
| 15.13 | 5.86 | 31.65 |
| 15.45 | 5.73 | 12.61 |
| 15.64 | 5.67 | 12.42 |
| 15.94 | 5.56 | 17.52 |
| 17.59 | 5.04 | 13.03 |
| 18.18 | 4.88 | 27.23 |
| 19.74 | 4.50 | 51.29 |
| 20.43 | 4.35 | 19.73 |
| 21.90 | 4.06 | 12.93 |
| 22.29 | 3.99 | 6.02 |
| 23.67 | 3.76 | 14.82 |
| 24.21 | 3.68 | 13.74 |
| 25.08 | 3.55 | 5.95 |
| 27.48 | 3.25 | 8.99 |
| 29.52 | 3.03 | 5.95 |
| 30.88 | 2.90 | 3.78 |
| 35.25 | 2.55 | 1.96 |

EXAMPLE 17 PREPARATION OF FORM VI OF SOTAGLIFLOZIN 115.0 mg of Sotagliflozin (the existing crystalline Form 2) was added into a 5-mL glass vial followed by adding 3 mL of $H_2O$. The sample was stirred at 50° C. for seven days, then filtered and dried to obtain a white solid.

Figure 17:
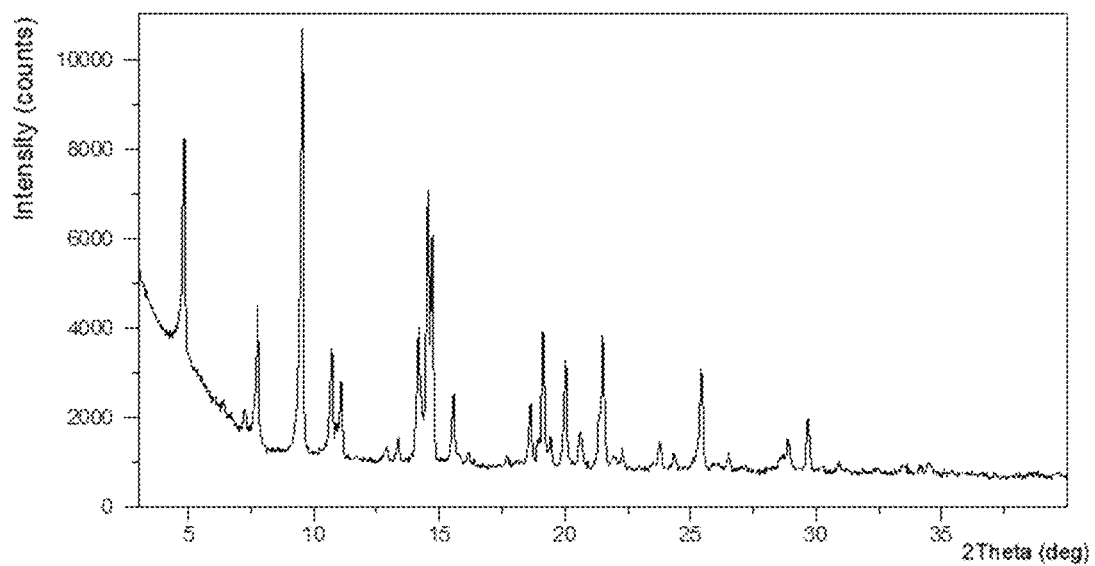
FIG. 17 shows an X-ray Powder Diffraction pattern of crystalline Form VI in example 17.
Figure 18:
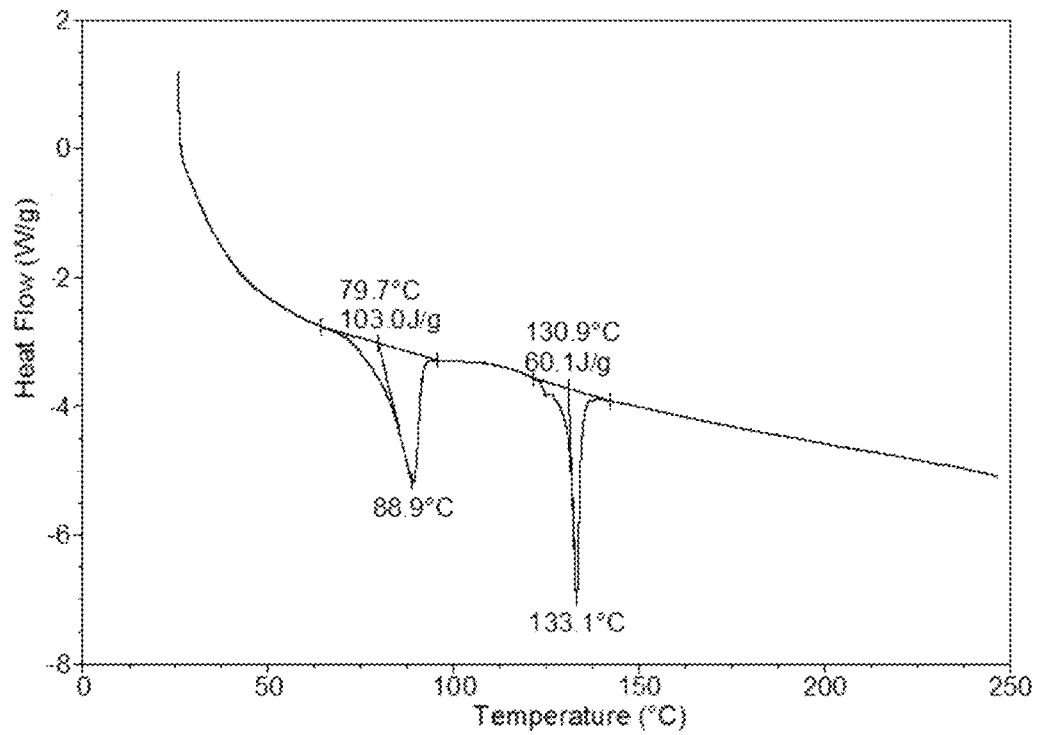
FIG. 18 shows a Differential Scanning calorimetry curve of crystalline Form VI in example 17.
Figure 19:
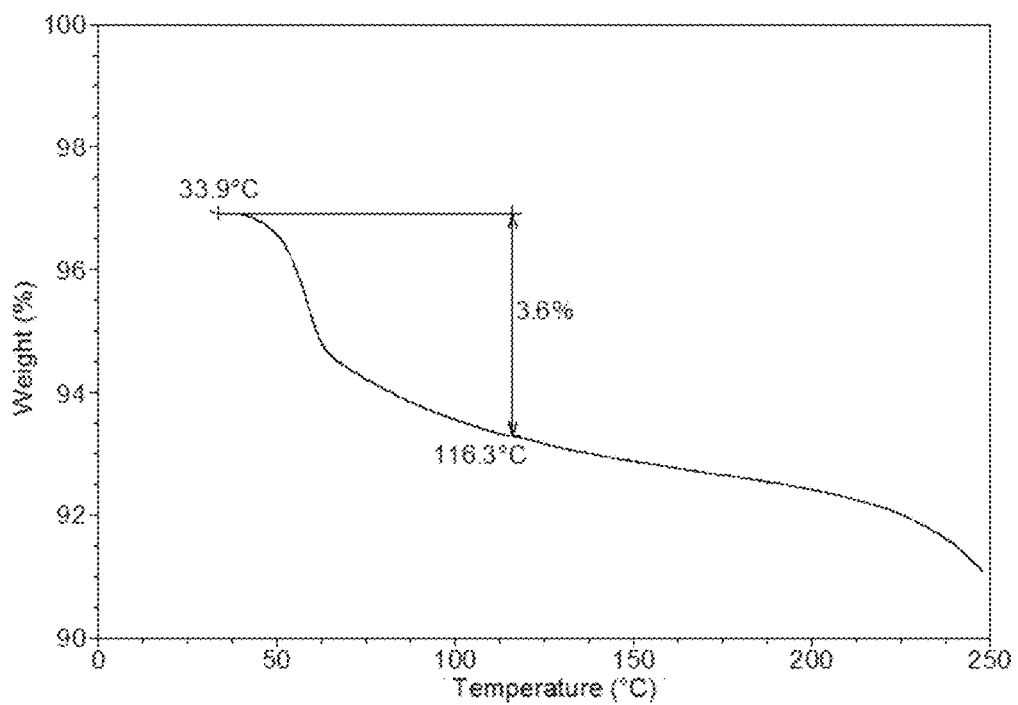
FIG. 19 shows a Thermal Gravimetric Analysis curve of crystalline Form VI in example 17.
Figure 20:
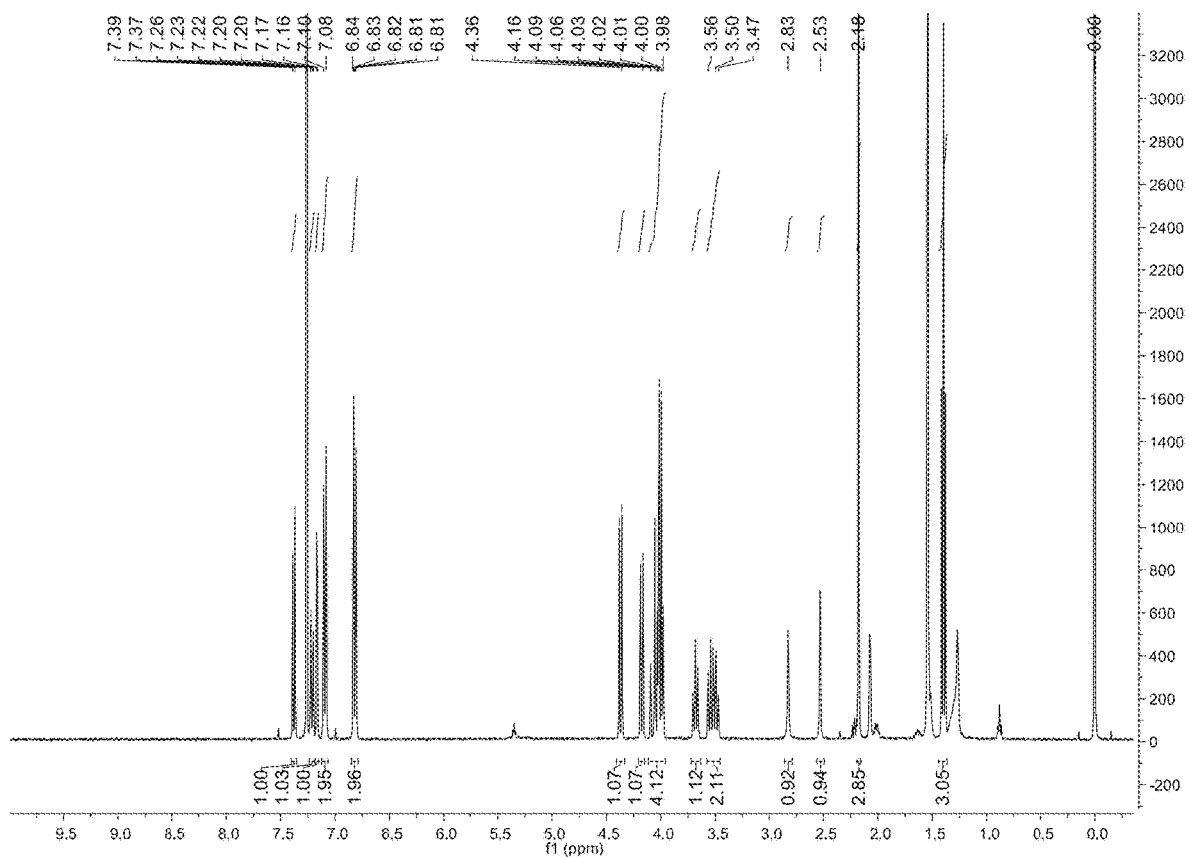
FIG. 20 shows a $^1$H NMR spectrum of crystalline Form VI in example 17.

The solid obtained in example 17 conformed to Form VI. The XRPD data were listed in Table 17, and the XRPD pattern was substantially as depicted in FIG. 17. The DSC curve was displayed in FIG. 18. The TGA curve was displayed in FIG. 19. The $^1H$ NMR spectrum was displayed in FIG. 20.

TABLE 17

| 2theta (°) | d spacing | Intensity % |
|---|---|---|
| 4.80 | 18.40 | 51.47 |
| 7.24 | 12.21 | 4.53 |
| 7.74 | 11.42 | 31.73 |
| 9.51 | 9.30 | 100.00 |
| 10.68 | 8.28 | 25.89 |
| 11.06 | 8.00 | 18.51 |
| 12.88 | 6.87 | 3.30 |
| 13.35 | 6.63 | 6.08 |
| 14.13 | 6.27 | 31.24 |
| 14.51 | 6.10 | 62.42 |
| 14.69 | 6.03 | 52.57 |
| 15.55 | 5.70 | 17.29 |
| 16.13 | 5.49 | 3.38 |
| 17.67 | 5.02 | 2.74 |
| 18.61 | 4.77 | 15.45 |
| 19.12 | 4.64 | 32.12 |
| 19.41 | 4.57 | 7.35 |
| 20.00 | 4.44 | 25.15 |
| 20.60 | 4.31 | 8.63 |
| 21.50 | 4.13 | 31.60 |
| 21.93 | 4.05 | 3.05 |
| 22.26 | 3.99 | 4.14 |
| 23.77 | 3.74 | 6.45 |
| 24.32 | 3.66 | 4.16 |
| 25.42 | 3.50 | 23.31 |
| 26.48 | 3.37 | 4.08 |
| 28.87 | 3.09 | 6.83 |
| 29.65 | 3.01 | 13.05 |
| 30.88 | 2.90 | 2.08 |
| 33.54 | 2.67 | 1.77 |
| 34.48 | 2.60 | 2.60 |
| 38.64 | 2.33 | 0.70 |

EXAMPLE 18 PREPARATION OF Form VI OF SOTAGLIFLOZIN 18.8 mg of Sotagliflozin (the existing crystalline Form 2) was added into a 1.5-mL glass vial followed by adding 0.8 mL of $H_2O$. The sample was stirred at 50° C. for three days, then filtered and dried to obtain a white solid.

Figure 39:
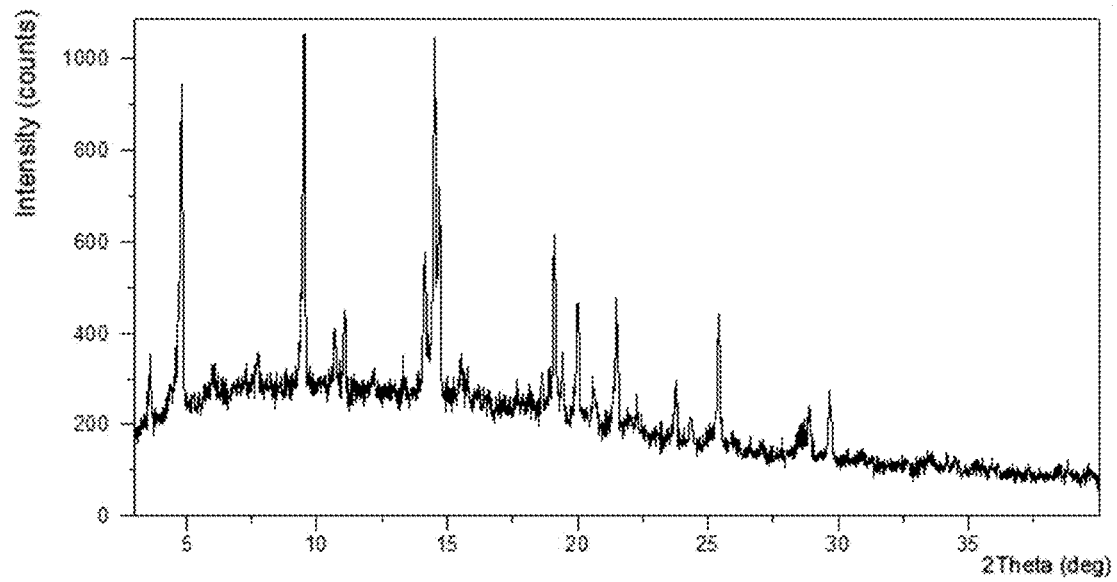
FIG. 39 shows an X-ray Powder Diffraction pattern of crystalline Form VI in example 18.

The solid obtained in example 18 conformed to Form VI. The XRPD data were listed in Table 18, and the XRPD pattern was substantially as depicted in FIG. 39.

TABLE 18

| 2theta (°) | d spacing | Intensity % |
|---|---|---|
| 3.61 | 24.50 | 18.95 |
| 4.81 | 18.39 | 92.45 |
| 5.97 | 14.80 | 10.94 |
| 7.71 | 11.47 | 14.56 |
| 9.51 | 9.30 | 100.00 |
| 10.66 | 8.30 | 18.48 |
| 11.05 | 8.00 | 23.13 |
| 14.14 | 6.27 | 38.35 |
| 14.51 | 6.11 | 94.71 |
| 14.70 | 6.03 | 58.36 |
| 15.55 | 5.70 | 10.64 |
| 19.11 | 4.64 | 46.22 |
| 19.42 | 4.57 | 12.30 |
| 20.00 | 4.44 | 30.50 |
| 20.59 | 4.31 | 8.40 |
| 21.50 | 4.13 | 30.51 |
| 23.75 | 3.75 | 12.87 |
| 24.33 | 3.66 | 6.56 |
| 25.41 | 3.51 | 34.58 |
| 28.89 | 3.09 | 11.62 |
| 29.64 | 3.01 | 18.86 |
| 38.58 | 2.33 | 1.20 |

EXAMPLE 19 PREPARATION OF FORM VII OF SOTAGLIFLOZIN 5.6 mg of Sotagliflozin (crystalline Form II of the present disclosure) was heated to 90° C. at a heating rate of 10° C./min by programmed temperature controlling, and then kept at 90° C. for 0.5 min to obtain a white solid.

Figure 21:
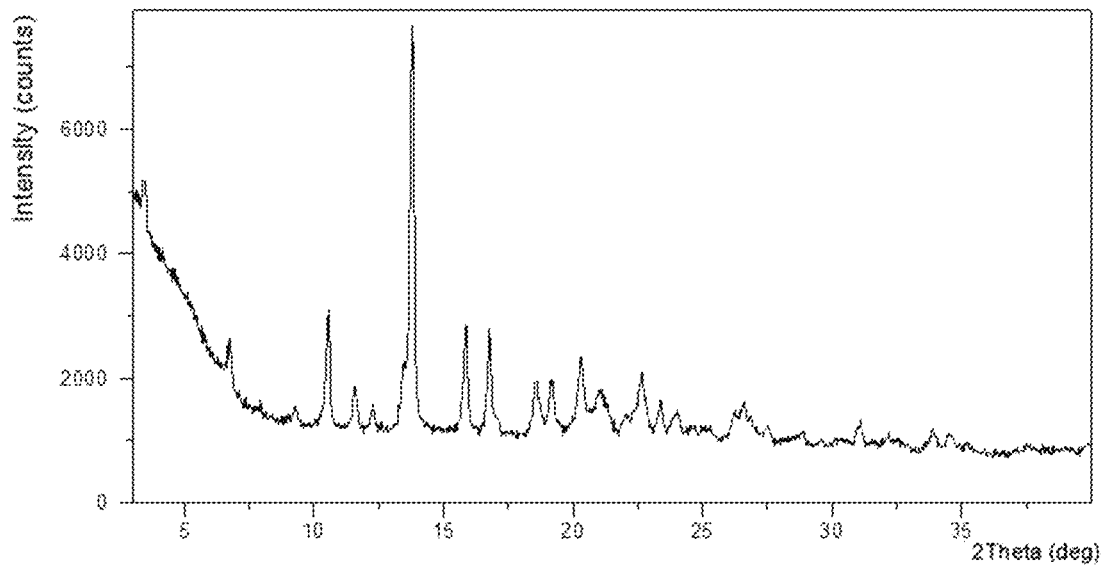
FIG. 21 shows an X-ray Powder Diffraction pattern of crystalline Form VII in example 19.
Figure 22:
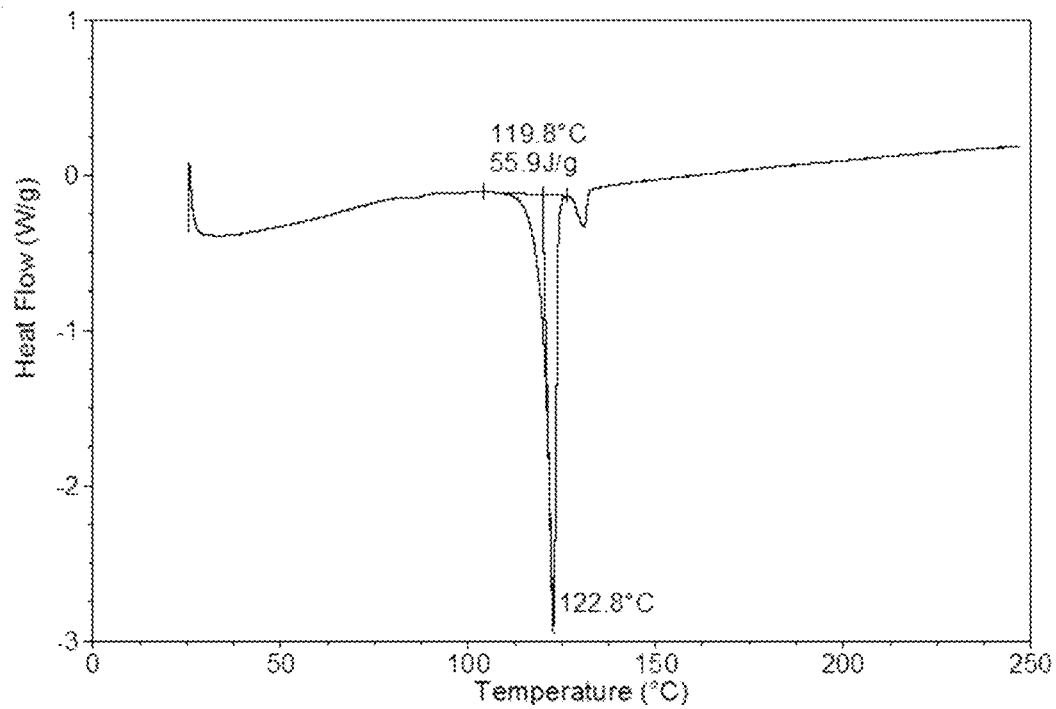
FIG. 22 shows a Differential Scanning calorimetry curve of crystalline Form VII in example 19.
Figure 23:
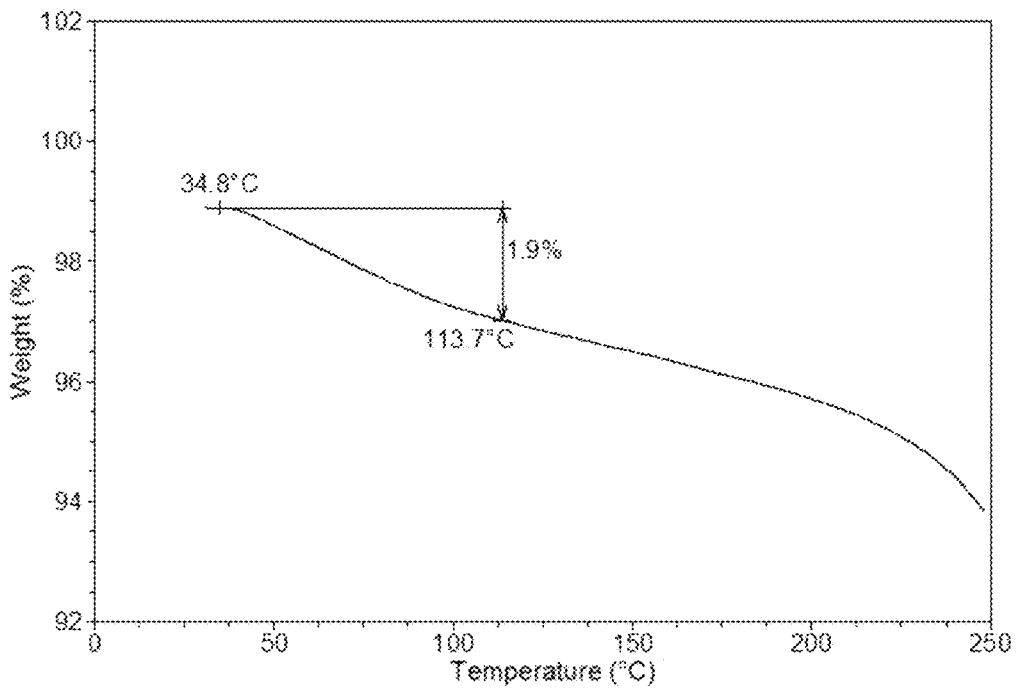
FIG. 23 shows a Thermal Gravimetric Analysis curve of crystalline Form VII in example 19.
Figure 24:
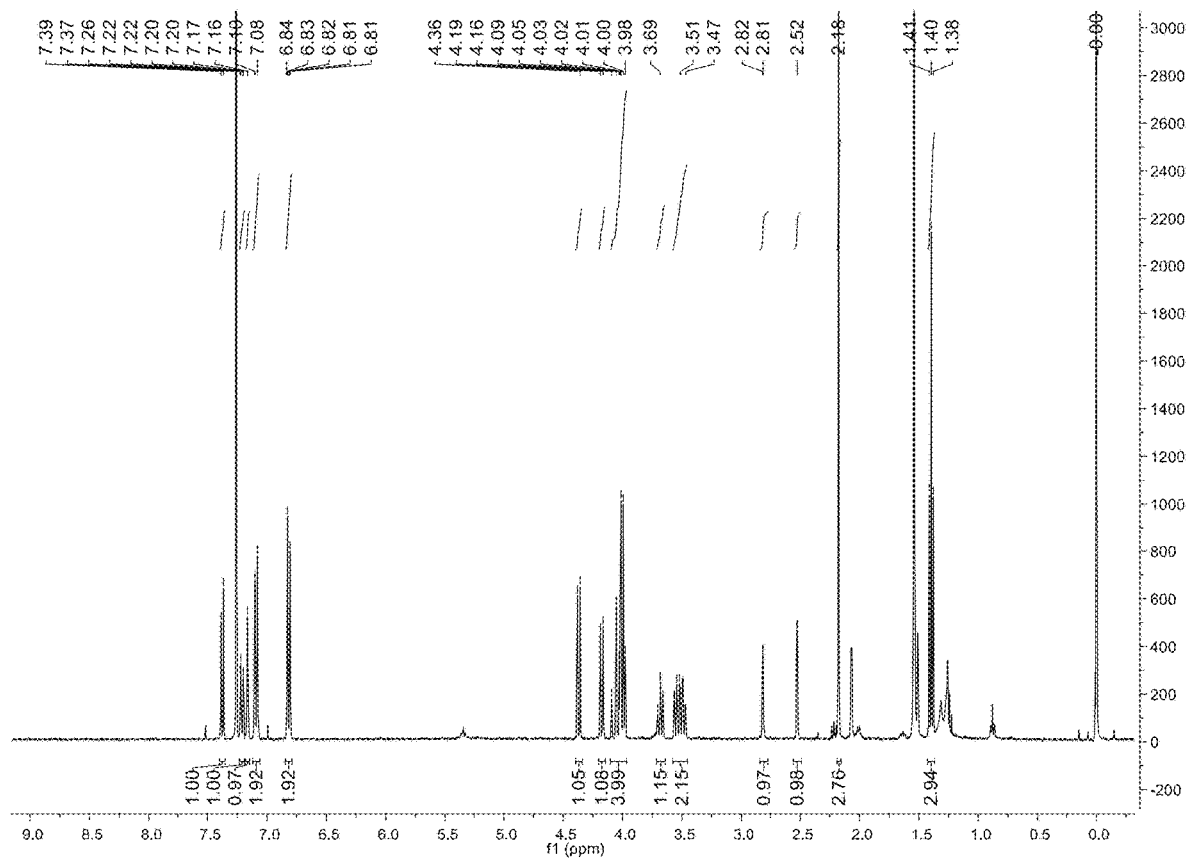
FIG. 24 shows a $^1$H NMR spectrum of crystalline Form VII in example 19.

The solid obtained in example 19 conformed to Form VII. The XRPD data were listed in Table 19, and the XRPD pattern was substantially as depicted in FIG. 21. The DSC curve was displayed in FIG. 22. The TGA curve was displayed in FIG. 23. The $^1H$ NMR spectrum was displayed in FIG. 24.

TABLE 19

| 2theta (°) | d spacing | Intensity % |
|---|---|---|
| 3.43 | 25.76 | 28.08 |
| 6.74 | 13.12 | 10.21 |
| 9.25 | 9.56 | 3.52 |
| 10.52 | 8.41 | 28.05 |
| 11.55 | 7.66 | 9.82 |
| 12.25 | 7.23 | 5.05 |
| 13.41 | 6.60 | 15.73 |
| 13.77 | 6.43 | 100.00 |
| 15.84 | 5.60 | 25.97 |
| 16.76 | 5.29 | 24.87 |
| 18.55 | 4.78 | 13.04 |
| 19.14 | 4.64 | 13.51 |
| 20.29 | 4.38 | 19.00 |
| 20.98 | 4.23 | 10.62 |
| 22.01 | 4.04 | 5.70 |
| 22.62 | 3.93 | 15.97 |
| 23.36 | 3.81 | 9.77 |
| 24.00 | 3.71 | 6.79 |
| 25.18 | 3.54 | 2.98 |
| 26.19 | 3.40 | 6.94 |
| 26.56 | 3.36 | 9.66 |
| 27.50 | 3.24 | 4.22 |
| 28.79 | 3.10 | 2.89 |
| 31.04 | 2.88 | 5.03 |
| 32.37 | 2.77 | 2.28 |
| 33.87 | 2.65 | 5.02 |
| 34.53 | 2.60 | 4.13 |
| 37.52 | 2.40 | 1.20 |

EXAMPLE 20 PREPARATION OF FORM VIII OF SOTAGLIFLOZIN 1.7 mg of Sotagliflozin (crystalline Form V of the present disclosure) was heated to 65° C. at a heating rate of 10° C./min by programmed temperature controlling, and then kept at 65° C. for 2 min to obtain a white solid.

Figure 25:
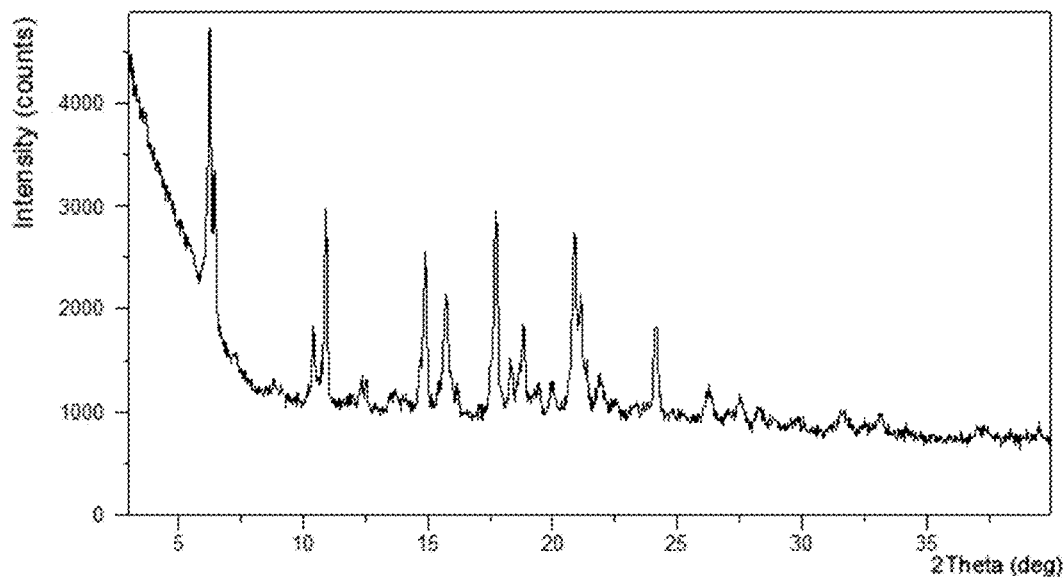
FIG. 25 shows an X-ray Powder Diffraction pattern of crystalline Form VIII in example 20.
Figure 26:
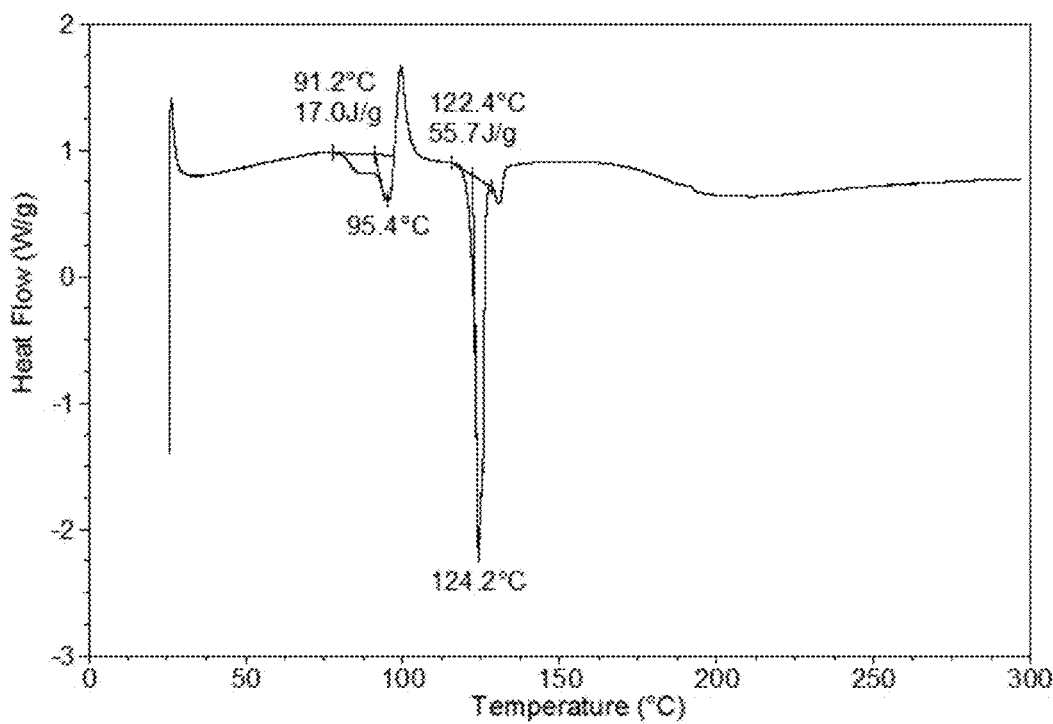
FIG. 26 shows a Differential Scanning calorimetry curve of crystalline Form VIII in example 20.

The solid obtained in example 20 conformed to Form VIII. The XRPD data were listed in Table 20, and the XRPD pattern was substantially as depicted in FIG. 25. The DSC curve was displayed in FIG. 26.

TABLE 20

| 2theta (°) | d spacing | Intensity % |
|---|---|---|
| 6.23 | 14.19 | 100.00 |
| 6.44 | 13.72 | 52.98 |
| 8.91 | 9.93 | 2.27 |
| 10.37 | 8.53 | 27.84 |
| 10.89 | 8.12 | 70.03 |
| 12.50 | 7.08 | 9.74 |
| 13.68 | 6.47 | 6.05 |
| 14.88 | 5.95 | 54.69 |
| 15.74 | 5.63 | 41.14 |
| 17.71 | 5.01 | 72.38 |
| 18.32 | 4.84 | 18.25 |
| 18.82 | 4.72 | 33.91 |
| 19.43 | 4.57 | 10.41 |
| 19.92 | 4.46 | 12.53 |
| 20.86 | 4.26 | 66.09 |
| 21.12 | 4.21 | 42.29 |
| 21.85 | 4.07 | 15.63 |
| 24.13 | 3.69 | 34.81 |
| 26.26 | 3.39 | 12.55 |
| 27.52 | 3.24 | 10.01 |
| 28.23 | 3.16 | 7.13 |
| 29.87 | 2.99 | 3.93 |
| 31.60 | 2.83 | 7.07 |
| 33.16 | 2.70 | 7.22 |
| 37.17 | 2.42 | 3.12 |

EXAMPLE 21 STABILITY STUDY

The mixture of existing crystalline Form 2 disclosed in CN102112483A, Form I and Form II was stirred in several solvent systems with different water activity ($a_w$). After stirring for 70 hours, residual solids were analyzed by XRPD, and the results were listed in Table 21.

TABLE 21

| Solvent system | $a_w$ | Initial form | Final form |
|---|---|---|---|
| H$_2$O/IPA = 6:94 | 0.5 | Form 2, Form I, Form II | Form II |
| H$_2$O/IPA = 11:89 | 0.7 | Form 2, Form I, Form II | Form II |
| H$_2$O/IPA = 15:85 | 0.8 | Form 2, Form I, Form II | Form II |
| H$_2$O/IPA = 23:77 | 0.9 | Form 2, Form I, Form II | Form II |
| H$_2$O/IPA = 35:65 | 0.95 | Form 2, Form I, Form II | Form II |
| H$_2$O | 1.0 | Form 2, Form I, Form II | Form I |

The results indicate that Form I and Form II were more stable than Form 2 in high water activity (high humidity, ≥50% RH) environment.

It should be noted that the solvent systems for different water activity ($a_w$) include but not limit to H$_2$O and IPA. The same conclusion could be drawn with this experiment in other solvent systems suitable for the preparation of different water activity ($a_w$).

EXAMPLE 22 HYGROSCOPICITY ASSESSMENT OF FORM I OF THE PRESENT INVENTION

Figure 40:
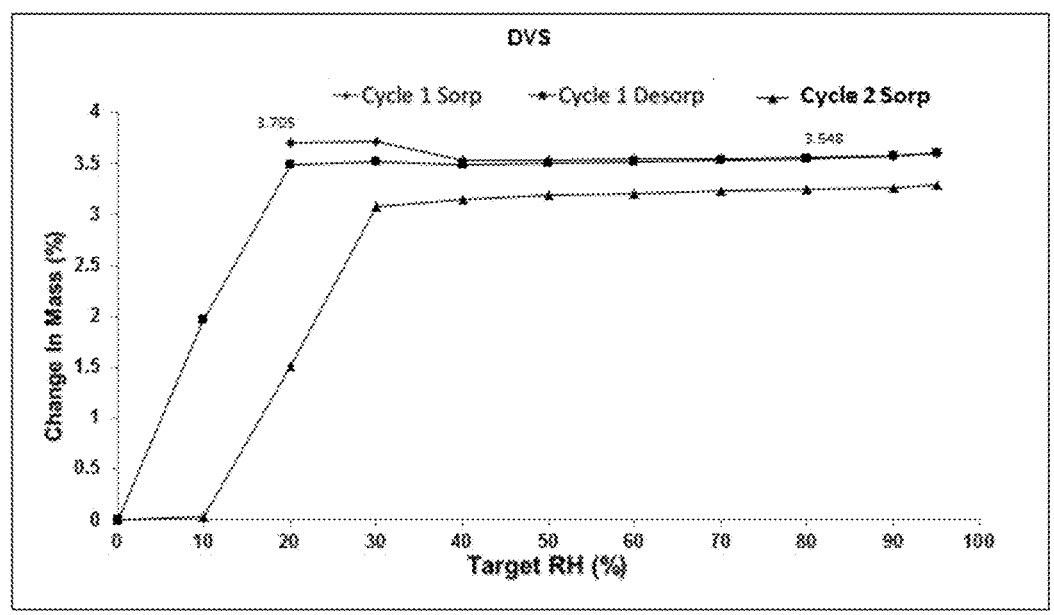
FIG. 40 shows a DVS plot of crystalline Form I in example 22.

Dynamic vapor sorption (DVS) was applied to test hygroscopicity of crystalline Form I with 13.8 mg of sample Form I at 25° C. The weight gains at each relative humidity were recorded in a cycle of 20%-95%-0%-95% RH. Crystalline Form I had a low hygroscopicity with a 3.55% weight gain under 80% RH. The result was listed in Table 22 and the DVS plot was shown in FIG. 40. The XRPD pattern of Form I was substantially unchanged following the DVS test.

TABLE 22

| | Relative Humidity (RH) | |
|---|---|---|
| Weight gain (%) | Weight gain under 80% RH | Form change before and after DVS |
| Form I | 3.55% | No form change |

EXAMPLE 23 HYGROSCOPICITY ASSESSMENT OF FORM II OF THE PRESENT INVENTION

Figure 41:
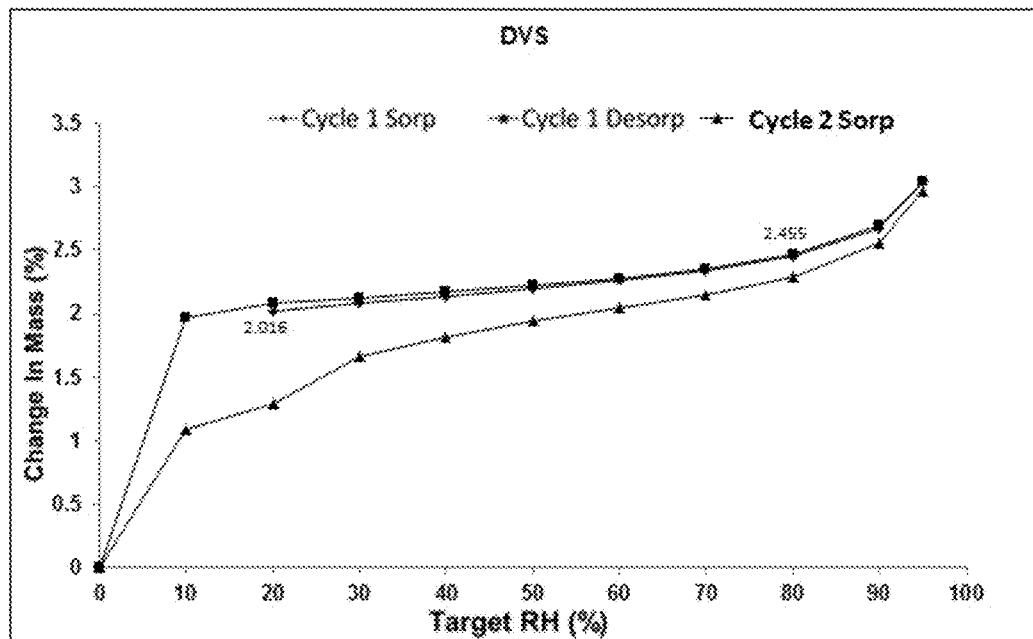
FIG. 41 shows a DVS plot of crystalline Form II in example 23.

Dynamic vapor sorption (DVS) was applied to test hygroscopicity of Form II with 10.4 mg of sample Form II at 25° C. The weight gains at each relative humidity were recorded in a cycle of 20%-95%-0%-95% RH. Form II had a low hygroscopicity with a 2.46% weight gain under 80% RH. The result was listed in Table 23 and the DVS plot was shown in FIG. 41. The XRPD pattern of Form II was substantially unchanged following the DVS test.

TABLE 23

| | Relative Humidity (RH) | |
|---|---|---|
| Weight gain (%) | Weight gain under 80% RH | Form change before and after DVS |
| Form II | 2.46% | No form change |

EXAMPLE 24 HYGROSCOPICITY ASSESSMENT OF FORM III OF THE PRESENT INVENTION

Figure 42:
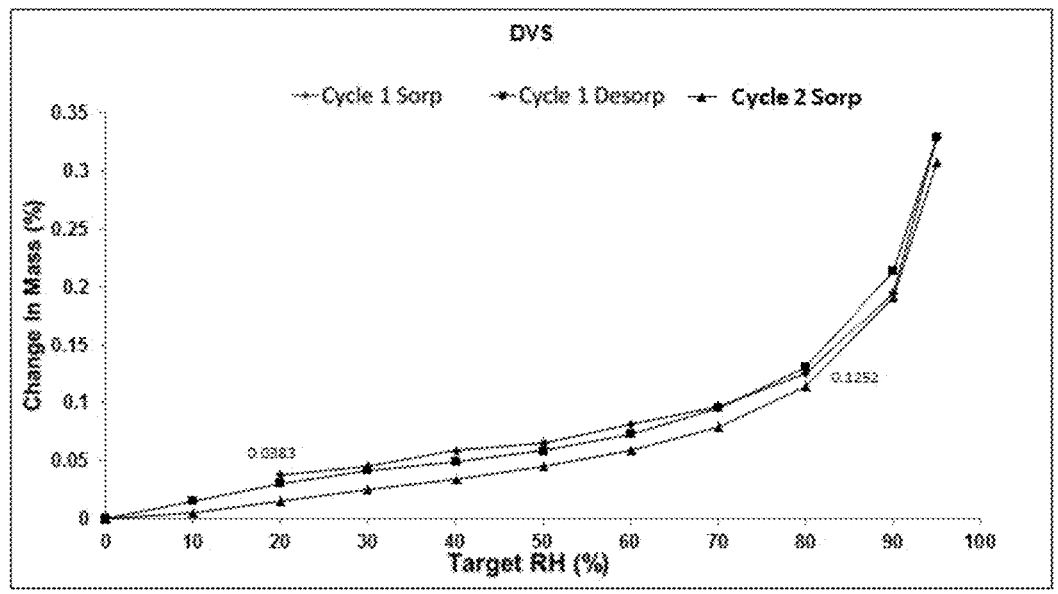
FIG. 42 shows a DVS plot of crystalline Form III in example 24.

Dynamic vapor sorption (DVS) was applied to test hygroscopicity of Form III with 9.1 mg of sample Form III at 25° C. The weight gains at each relative humidity were recorded in a cycle of 20%-95%-0%-95% RH. Form III had a low hygroscopicity with a 0.13% weight gain under 80% RH. The result was listed in Table 24 and the DVS plot was shown in FIG. 42. The XRPD pattern of Form III was substantially unchanged following the DVS test.

TABLE 24

| | Relative Humidity (RH) | |
|---|---|---|
| Weight gain (%) | Weight gain under 80% RH | Form change before and after DVS |
| Form III | 0.13% | No form change |

EXAMPLE 25 HYGROSCOPICITY ASSESSMENT OF FORM VI OF THE PRESENT INVENTION

Figure 43:
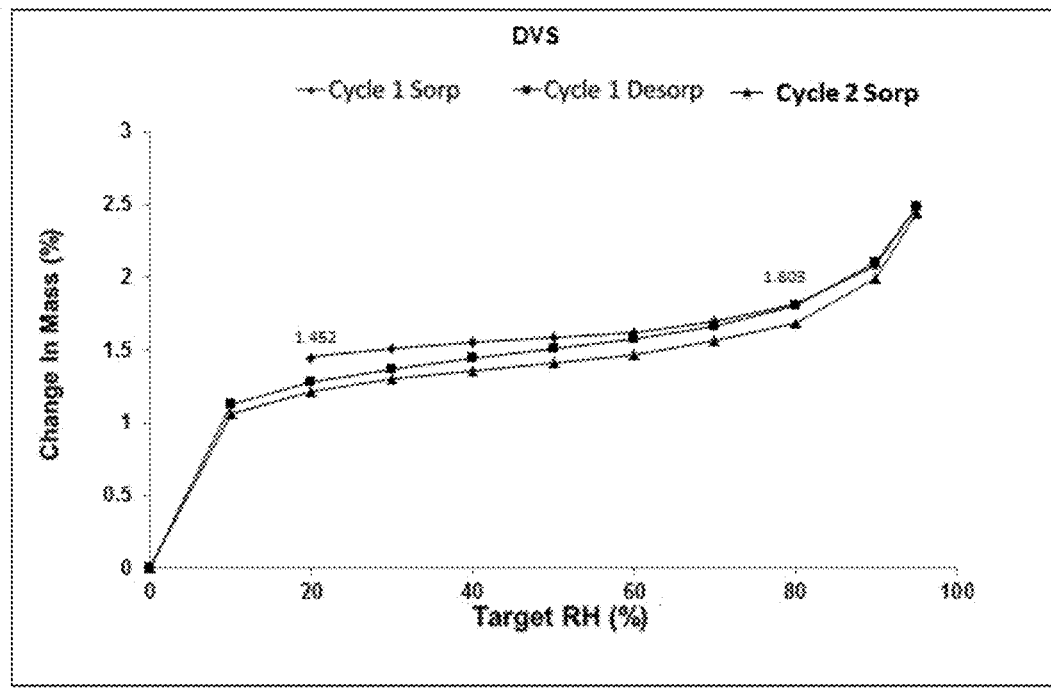
FIG. 43 shows a DVS plot of crystalline Form VI in example 25.
Figure 44:
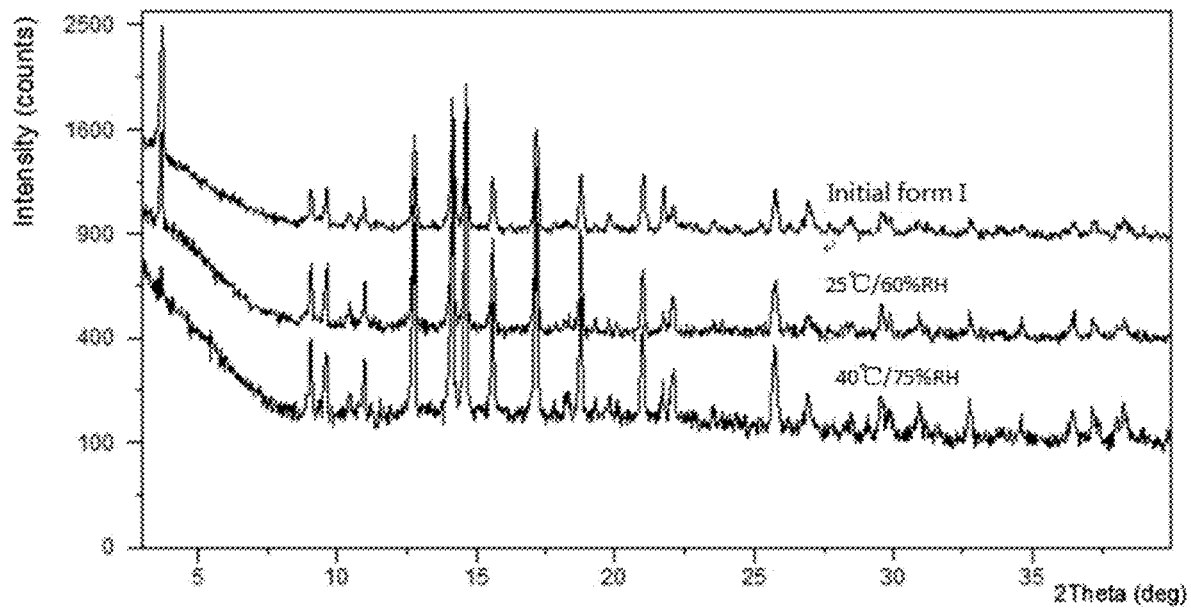
FIG. 44 shows XRPD patterns overlay of crystalline Form I before and after storage at 25° C./60% RH and 40° C./75% RH for 3 months.
Figure 45:
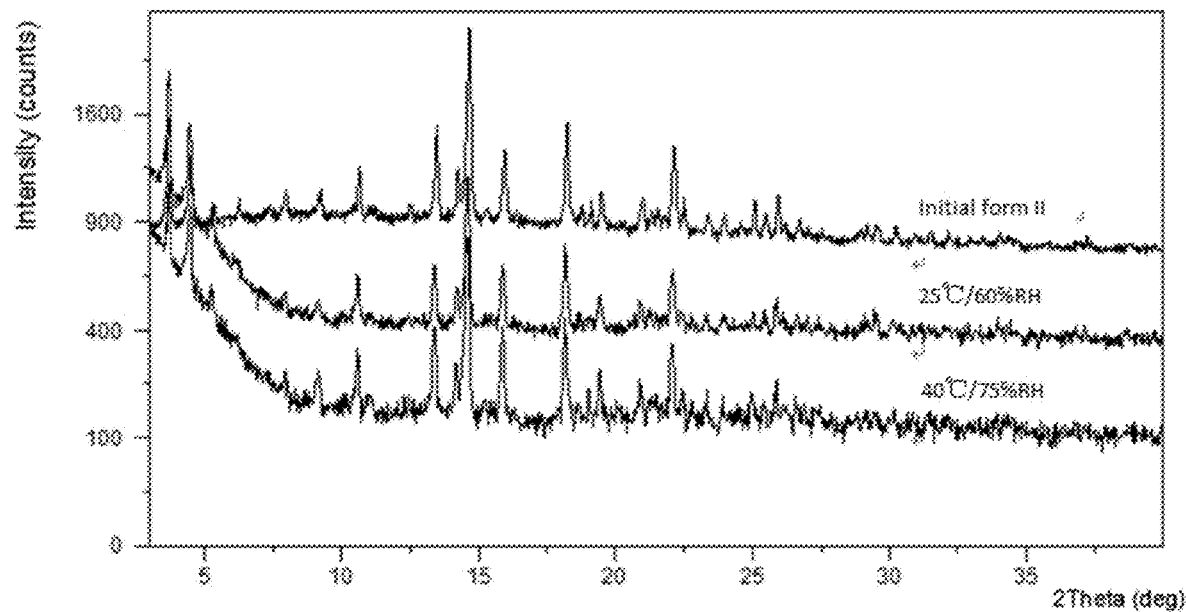
FIG. 45 shows XRPD patterns overlay of crystalline Form II before and after storage at 25° C./60% RH and 40° C./75% RH for 3 months.
Figure 46:
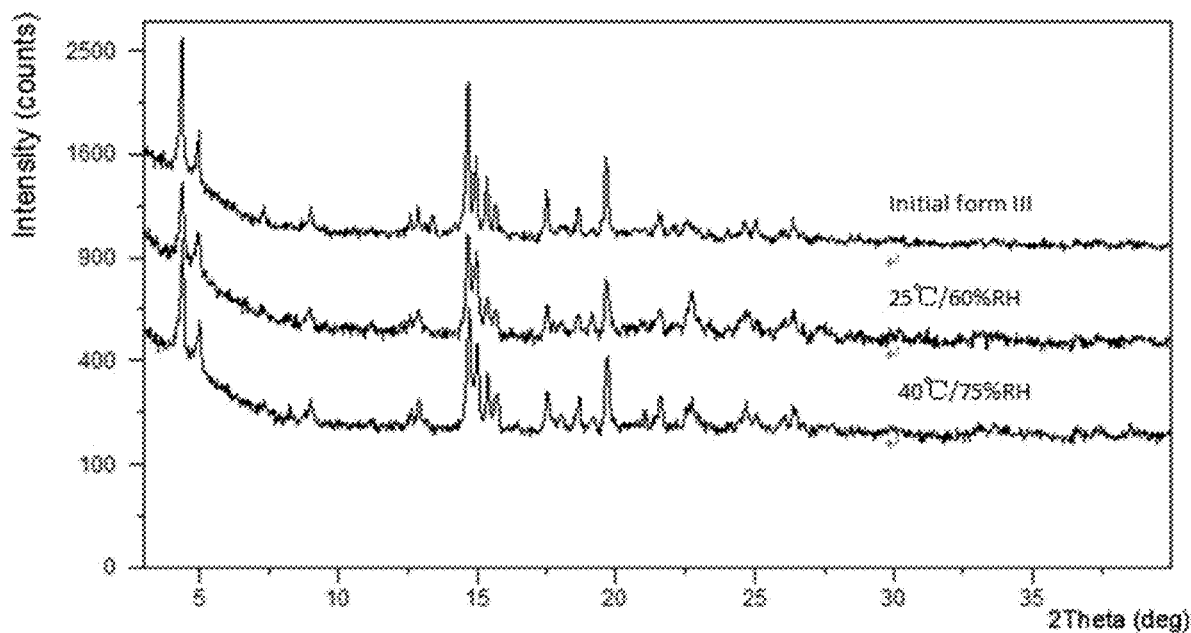
FIG. 46 shows XRPD patterns overlay of crystalline Form III before and after storage at 25° C./60% RH and 40° C./75% RH for 3 months.
Figure 47:
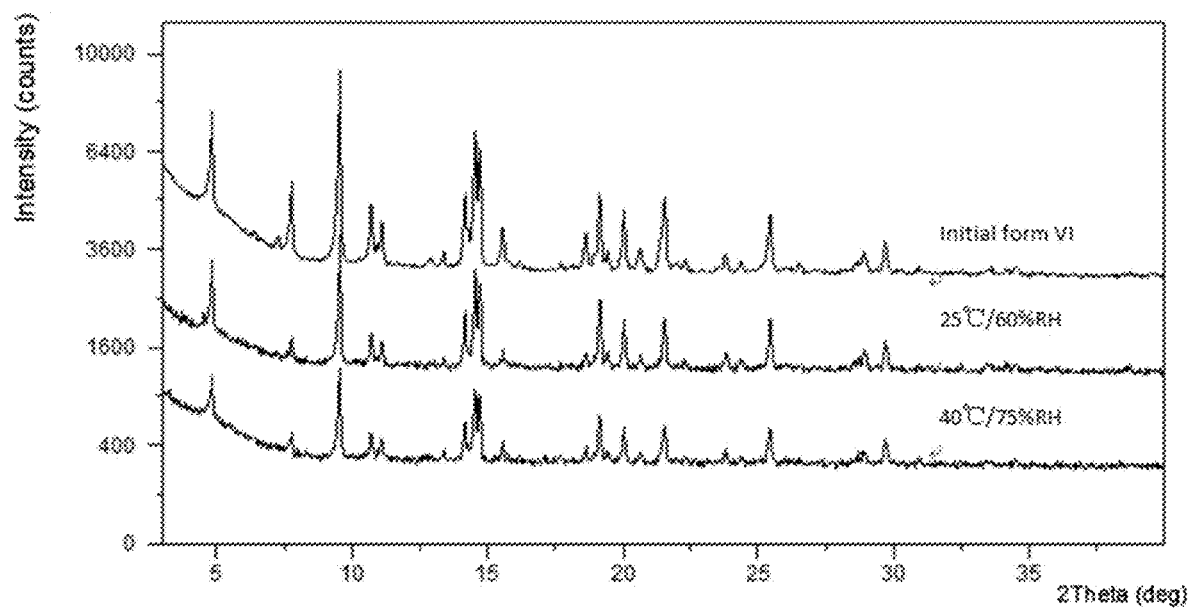
FIG. 47 shows XRPD patterns overlay of crystalline Form VI before and after storage at 25° C./60% RH and 40° C./75% RH for 3 months.

Dynamic vapor sorption (DVS) was applied to test hygroscopicity of Form VI with 4.5 mg of sample Form VI at 25° C. The weight gains at each relative humidity were recorded in a cycle of 20%-95%-0%-95% RH. Form VI had a low hygroscopicity with a 1.80% weight gain under 80% RH. The result was listed in Table 25 and the DVS plot was shown in FIG. 43. The XRPD pattern of Form VI was substantially unchanged following the DVS test.

TABLE 25

| | Relative Humidity (RH) | |
|---|---|---|
| Weight gain (%) | Weight gain under 80% RH | Form change before and after DVS |
| Form VI | 1.80% | No form change |

EXAMPLE 26 DYNAMIC SOLUBILITY

Saturated solutions of Form I, Form II, Form III, Form VII and the existing crystalline Form 2 in SGF (Simulated gastric fluids) were prepared. Saturated solutions of Form II, Form III, Form VII, Form VIII and the existing crystalline Form 2 in FaSSIF (Fasted state simulated intestinal fluids, pH=6.5) were prepared. After equilibrated for 1 hour, concentrations of the saturated solutions were measured by High Performance Liquid Chromatography (HPLC). The results were listed in Table 26 and Table 27. The results showed that the solubility of Form I, Form III and Form VII were 1.7 times, 2.2 times and 2.5 times as high as that of the existing crystalline Form 2 in SGF, respectively. The solubility of Form III, Form VII and Form VIII were 1.4 times, 1.5 times and 1.4 times as high as that of the existing crystalline Form 2 in FaSSIF, respectively.

TABLE 26

| Media:SGF | Solubility 1 hour (mg/mL) |
|---|---|
| Form I | 0.10 |
| Form II | 0.08 |
| Form III | 0.13 |
| Form VII | 0.15 |
| Form 2 | 0.06 |

TABLE 27

| Media:SGF | Solubility 1 hour (mg/mL) |
|---|---|
| Form II | 0.15 |
| Form III | 0.18 |
| Form VII | 0.20 |
| Form VIII | 0.18 |
| Form 2 | 0.13 |

EXAMPLE 27 STABILITY STUDY

Form I, Form II, Form III and Form VI were stored under different conditions of 25° C./60% RH and 40° C./75% RH for 3 months. XRPD was applied to detect the crystalline forms. The XRPD overlay of Form I, Form II, Form III and Form VI before and after stored under above two conditions were shown in FIG. 44, FIG. 45, FIG. 46 and FIG. 47, respectively. And the results were shown in Table 28. The results showed that Form I, Form II, Form III and Form VI had good stability under 25° C./60% RH and 40° C./75% RH for 3 months.

TABLE 28

| Initial Form | Conditions | Storage time | Solid Form after storage |
|---|---|---|---|
| Form I (the top pattern in FIG. 44) | 25° C./60% RH | 3 months | Form I (the middle pattern in FIG. 44) |
| | 40° C./75% RH | 3 months | Form I (the bottom pattern in FIG. 44) |
| Form II (the top pattern in FIG. 45) | 25° C./60% RH | 3 months | Form II (the middle pattern in FIG. 45) |
| | 40° C./75% RH | 3 months | Form II (the bottom pattern in FIG. 45) |
| Form III (the top pattern in FIG. 46) | 25° C./60% RH | 3 months | Form III (the middle pattern in FIG. 46) |
| | 40° C./75% RH | 3 months | Form III (the bottom pattern in FIG. 46) |
| Form VI (the top pattern in FIG. 47) | 25° C./60% RH | 3 months | Form VI (the middle pattern in FIG. 47) |
| | 40° C./75% RH | 3 months | Form VI (the bottom pattern in FIG. 47) |

EXAMPLE 28 MORPHOLOGY ASSESSMENT

Figure 48:
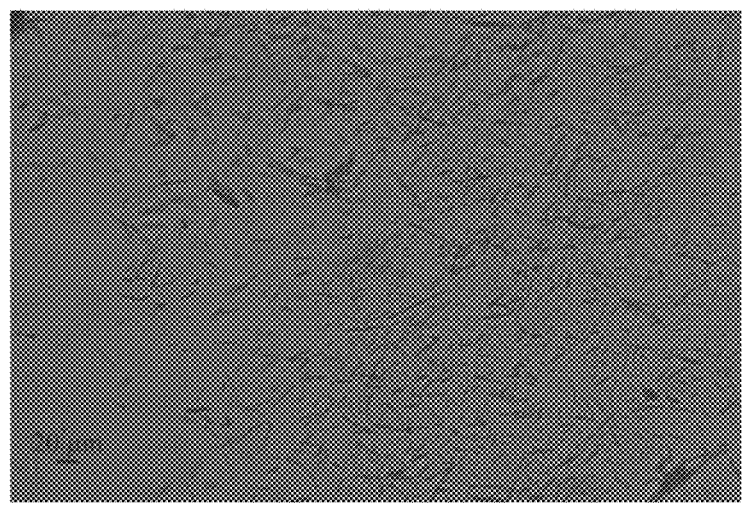
FIG. 48 shows a PLM picture of the existing crystalline Form 2.
Figure 49:
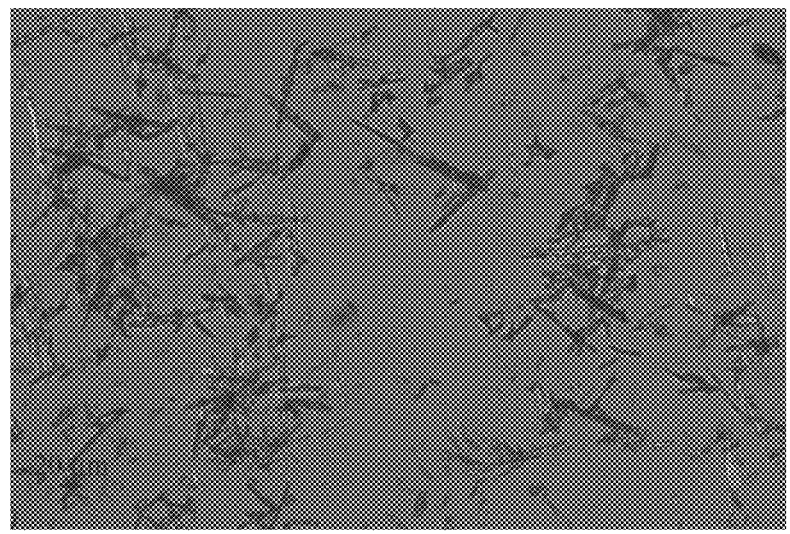
FIG. 49 shows a PLM picture of the crystalline Form I in the present disclosure.
Figure 50:
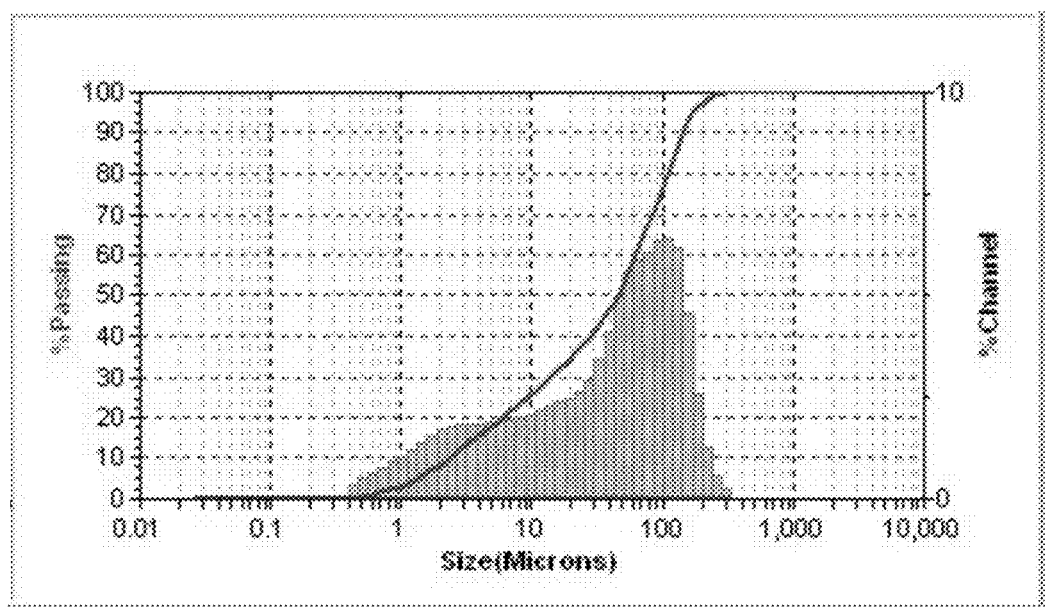
FIG. 50 shows a PSD diagram of the existing crystalline Form 2.
Figure 51:
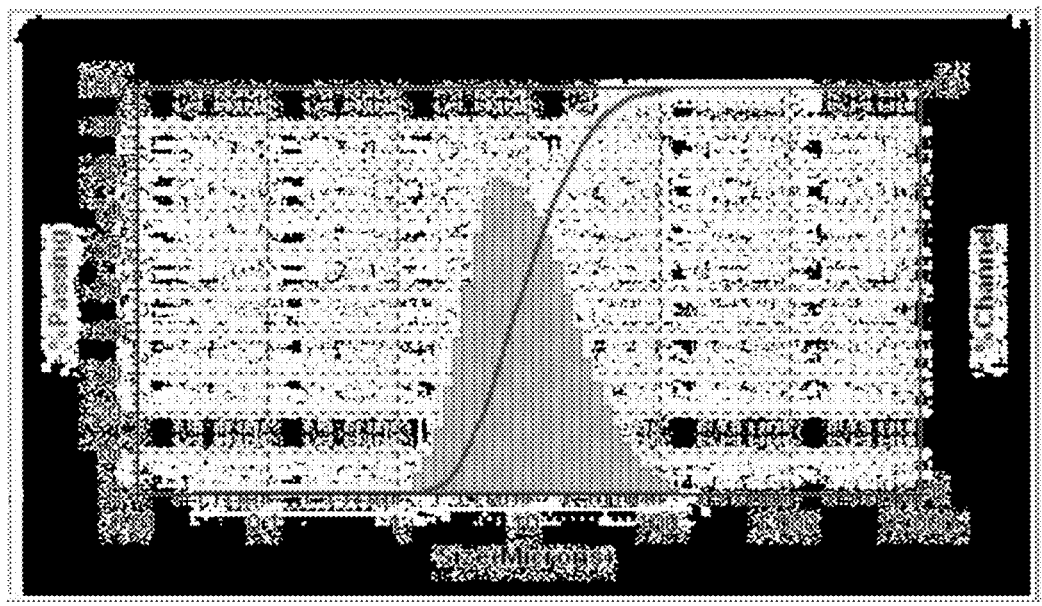
FIG. 51 shows a PSD diagram of the crystalline Form I in the present disclosure.
Figure 52:
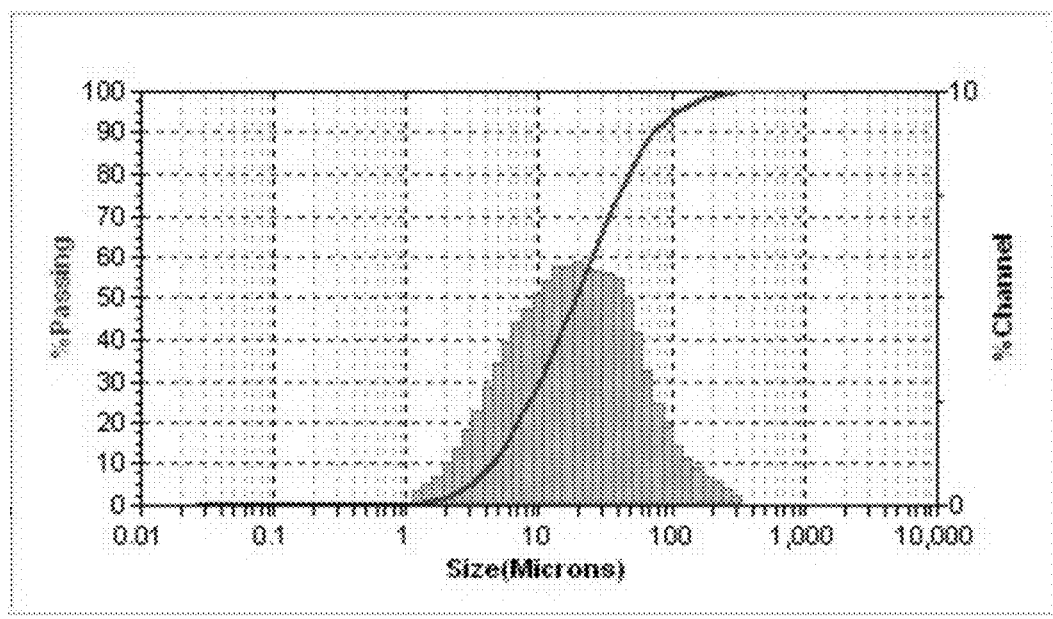
FIG. 52 shows a PSD diagram of the crystalline Form V in the present disclosure.

The existing crystalline Form 2 and Form I in the present disclosure were tested by polarized light microscopy. The PLM results of the Form 2 and Form I were shown in FIG. 48 and FIG. 49, respectively.

Figure 56:
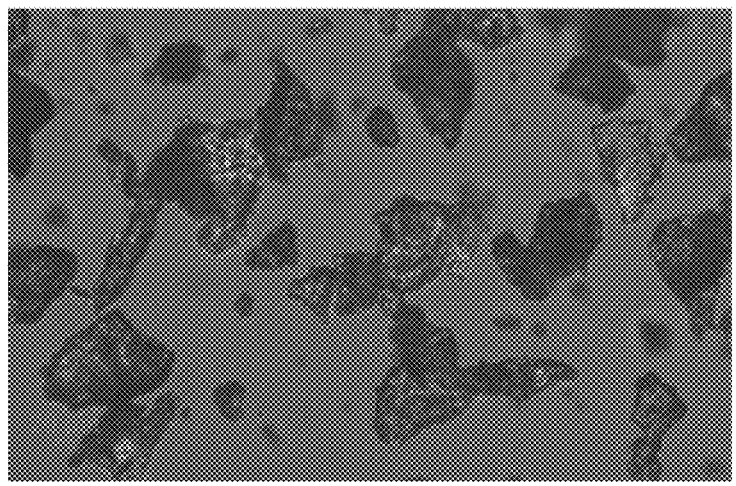
FIG. 56 shows a PLM picture of the crystalline Form VII in the present disclosure.
Figure 57:
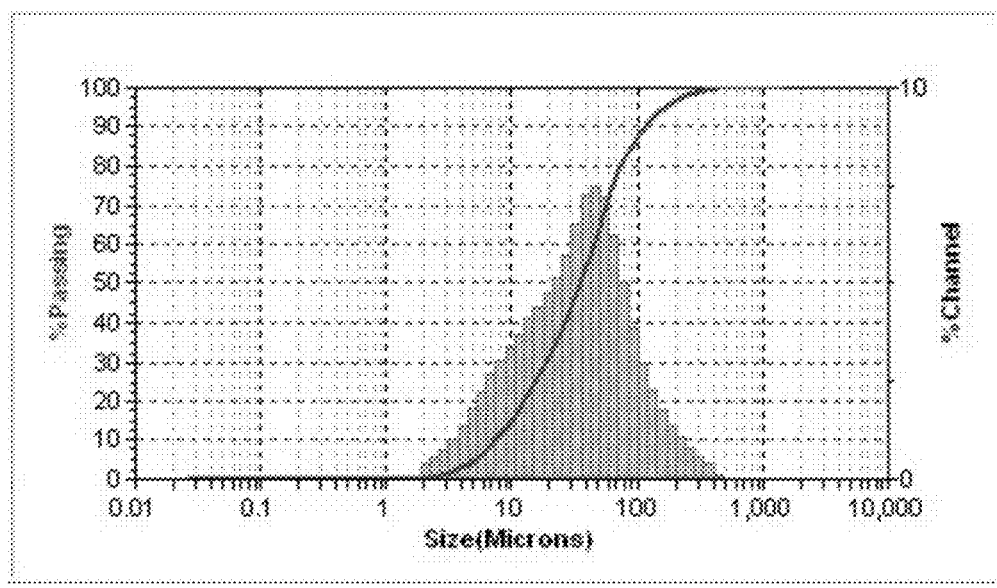
FIG. 57 shows a PSD diagram of the crystalline Form VIII in the present disclosure.

The results showed that existing crystalline Form 2 had a needle-like shape, while Form I in the present disclosure had a rod-like shape with uniform particle size distribution. The uniform particle size distribution was beneficial to the post-treatment of drug development and improved quality control. As depicted in FIG. 56, Form VII had an irregular massive shape with uniform particle size distribution. Compared with the needle-like crystalline Form 2, the massive crystal had better fluidity, which cloud significantly improve the filtration efficiency of API and facilitate the drug's dispersion in drug development.

EXAMPLE 29 PARTICLE SIZE DISTRIBUTION ASSESSMENT

Certain amount of Form I, Form V, Form VIII and existing crystalline Form 2 were taken for particle size distribution test, and the results were shown in Table 29.

TABLE 29

| Solid form | MV (μm) | SD | D10 (μm) | D50 (μm) | D90 (μm) |
|---|---|---|---|---|---|
| Form 2 | 60.43 | 59.06 | 2.32 | 45.00 | 144.4 |
| Form I | 14.48 | 9.76 | 3.34 | 8.97 | 31.63 |
| Form V | 32.70 | 24.46 | 4.38 | 18.81 | 72.98 |
| Form VIII | 51.93 | 37.50 | 7.30 | 36.60 | 112.4 |

The particle size distribution diagram of the existing crystalline Form 2, Form I, Form V and Form VIII were shown in FIG. 50, FIG. 51, FIG. 52 and FIG. 57, respectively.

The results showed that the particle size distribution of existing crystalline Form 2 was wide and bimodal, which supposed to be caused by agglomeration. The nonuniform particle size distribution and particle agglomeration had a very negative impact on the content uniformity of drug product, thereby having effects on dissolution, absorption of drug substance, and may causing variation of absorption or dissolution profile between batches. Inversely, the particle size distribution of Form I, Form V and Form VIII were narrow and normal. The uniform particle size distribution was beneficial to the content uniformity of drug product, which could also simplify the process and have a positive impact on drug development.

EXAMPLE 30 MECHANICAL STABILITY ASSESSMENT

Figure 53:
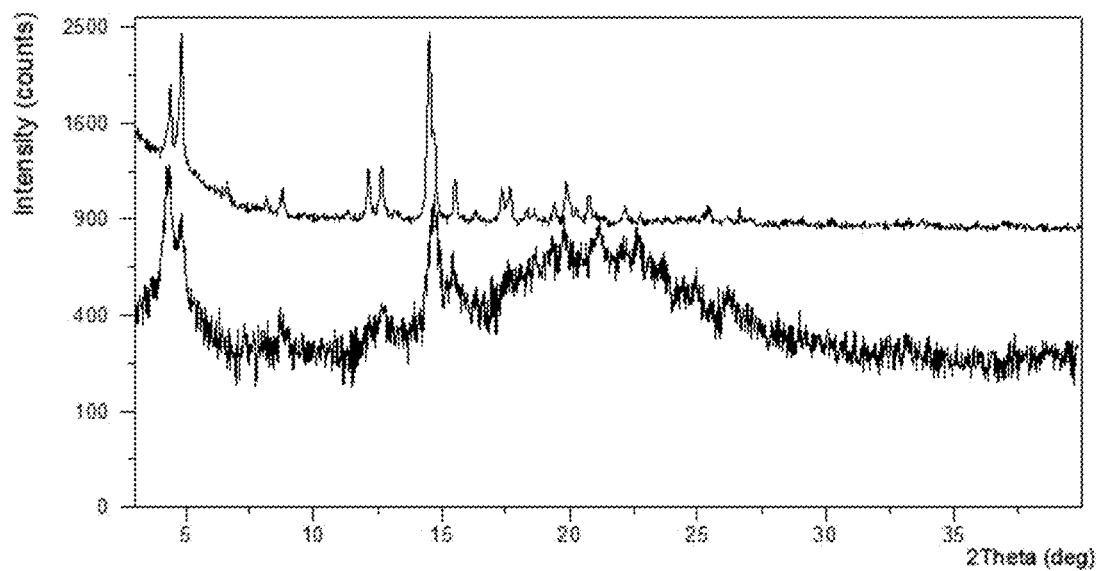
FIG. 53 shows XRPD patterns overlay of the existing crystalline Form 2 before and after grinding.
Figure 54:
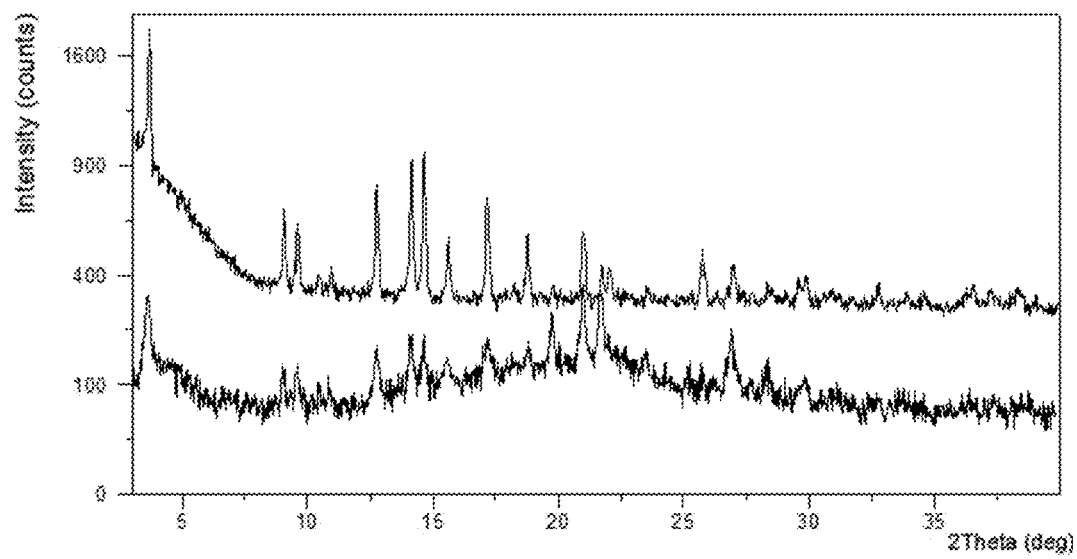
FIG. 54 shows XRPD patterns overlay of the crystalline Form I in the present disclosure before and after grinding.
Figure 55:
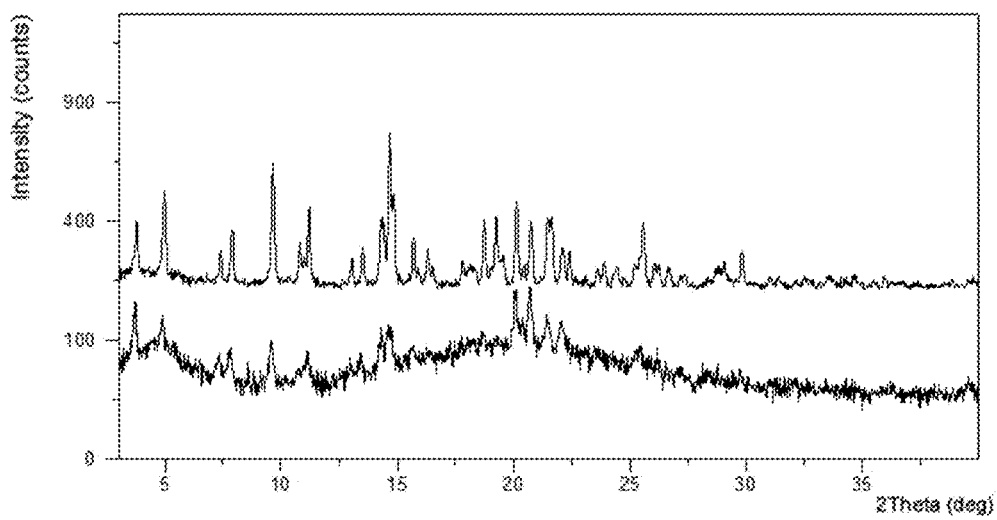
FIG. 55 shows XRPD patterns overlay of the crystalline Form VI in the present disclosure before and after grinding.

Solid sample of Form I, Form VI and the existing crystalline Form 2 were ground manually for 5 minutes in mortar. XRPD was applied to detect the crystalline form. The XRPD overlay of Form I, Form VI and the existing crystalline Form 2 before and after grinding were listed from FIGS. 53 to 55 (The XRPD pattern before grinding was showed on the top in the pattern, and the XRPD pattern after grinding was showed on the bottom in the pattern), respectively. The results were shown in Table 30.

TABLE 30

| Initial form | Final form | Crystallinity |
|---|---|---|
| Form I | Form I | Decreased (Slightly amorphous) |
| Form VI | Form VI | Decreased (Slightly amorphous) |
| Form 2 | Form 2 | Decreased (Mainly amorphous) |

The results showed that no crystalline form change of Form I and Form VI were observed under certain mechanical stress. Physical and chemical properties of Form I and Form VI could remain unchanged with only slightly decreased crystallinity and little amount of amorphous appeared. Inversely, the existing crystalline Form 2 had poor mechanical stability with significantly decreased crystallinity and large amount of amorphous appeared. Form I and Form VI are more suitable for drug preparation, storage and crystallization process because they had better mechanical stability than that of the existing crystalline Form 2.

EXAMPLE 31 HYGROSCOPICITY ASSESSMENT OF FORM VII OF THE PRESENT INVENTION

Figure 58:
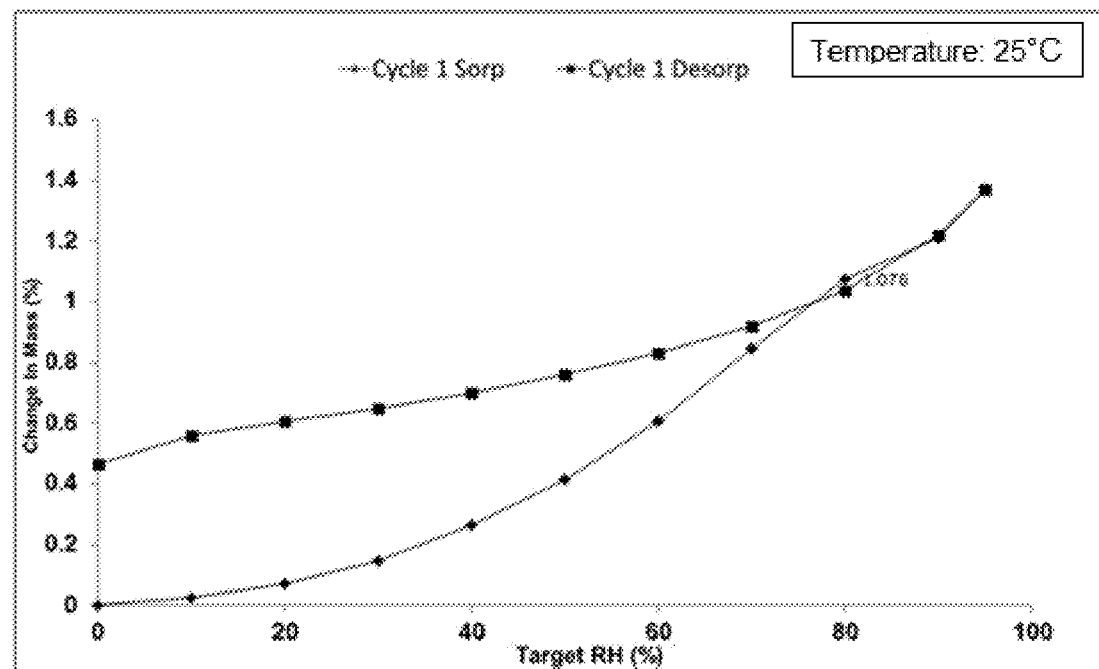
FIG. 58 shows a DVS plot of crystalline Form VII in example 31.

Dynamic vapor sorption (DVS) was applied to test hygroscopicity of Form VII with 11.5 mg of sample Form VII at 25° C. The weight gains at each relative humidity were recorded in a cycle of 0%-95%-0% RH. Form VII had a low hygroscopicity with a 1.08% weight gain under 80% RH. The result was listed in Table 31 and the DVS plot was shown in FIG. 58. The XRPD pattern of Form VII was substantially unchanged following the DVS test.

TABLE 31

| | Relative Humidity (RH) | |
|---|---|---|
| Weight gain (%) | Weight gain under 80% RH | Form change before and after DVS |
| Form VII | 1.08% | No form change |

EXAMPLE 32 HYGROSCOPICITY ASSESSMENT OF FORM VIII OF THE PRESENT INVENTION

Figure 59:
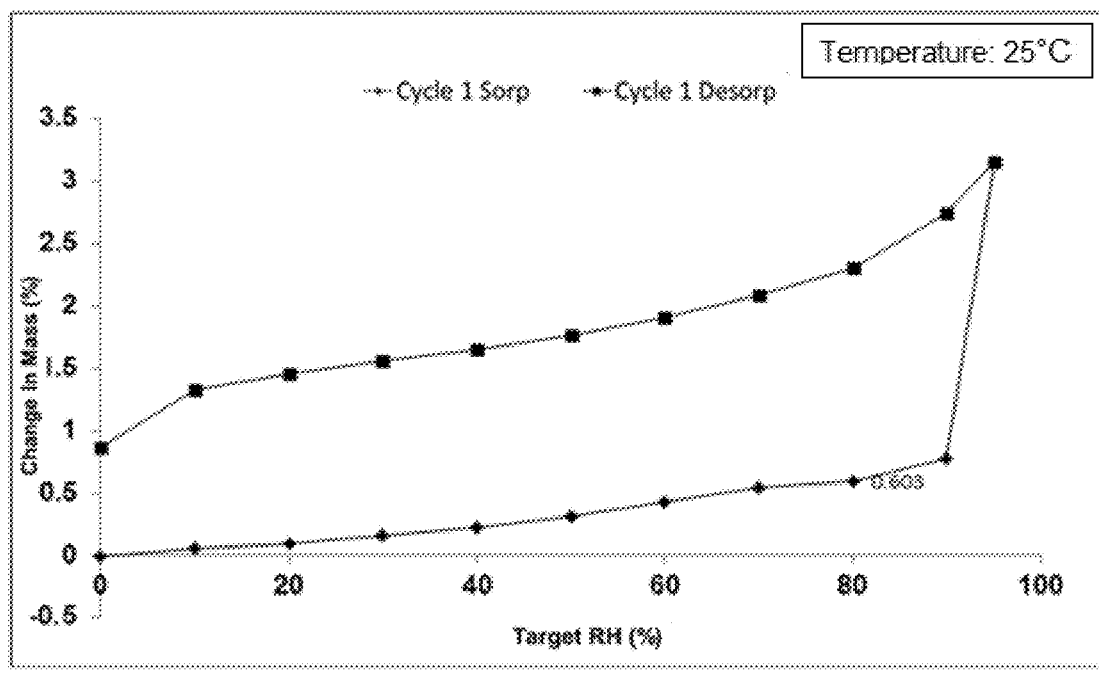
FIG. 59 shows a DVS plot of crystalline Form VIII in example 32.

Dynamic vapor sorption (DVS) was applied to test hygroscopicity of Form VIII with 10.6 mg of sample Form VIII at 25° C. The weight gains at each relative humidity were recorded in a cycle of 0%-95%-0% RH. Form VIII had a low hygroscopicity with a 0.60% weight gain under 80% RH. The result was listed in Table 32 and the DVS plot was shown in FIG. 59. The XRPD pattern of Form VIII was substantially unchanged following the DVS test.

TABLE 32

| | Relative Humidity (RH) | |
|---|---|---|
| Weight gain (%) | Weight gain under 80% RH | Form change before and after DVS |
| Form VIII | 0.60% | No form change |

Those skilled in the art will understand that, under the teachings of this specification, it can make some modifications or variations of the present disclosure. Such modifications and variations are also in the scope of claims defined in the present disclosure.

What is claimed is:

1. A crystalline Form I of Sotagliflozin, wherein the X-ray powder diffraction pattern shows characteristic peaks at 2theta values of 3.6°±0.2°, 12.7°±0.2° and 14.1°±0.2° using CuKα radiation.

2. The crystalline Form I according to claim 1, wherein the X-ray powder diffraction pattern shows one or two or three characteristic peaks at 2theta values of 15.6°±0.2°, 17.1°±0.2° and 18.7°±0.2° using CuKα radiation.

3. The crystalline Form I according to claim 1, wherein the X-ray powder diffraction pattern shows one or two or three characteristic peaks at 2theta values of 9.0°±0.2°, 21.0°±0.2° and 25.7°±0.2° using CuKα radiation.

4. A process for preparing crystalline Form I of Sotagliflozin according to claim 1, wherein the process comprises:
   1) Dissolving a solid of Sotagliflozin into an alcohol, ketone or cyclic ether to obtain a solution, adding water slowly and dropwise into the solution or adding the solution dropwise into water to obtain a solid precipitation, then stirring the mixture at room temperature for 1-72 hours, filtering and drying to obtain a white solid; or
   2) Adding a solid of Sotagliflozin into water to prepare a suspension, stirring at room temperature for 5-15 days, filtering and drying to obtain a white solid.

5. A pharmaceutical composition, comprising a therapeutically effective amount of crystalline Form I according to claim 1 and pharmaceutically acceptable carriers, diluents or excipients.

* * * * *